(12) United States Patent
Klosin et al.

(10) Patent No.: US 9,029,487 B2
(45) Date of Patent: *May 12, 2015

(54) PROCESS FOR POLYMERIZING A POLYMERIZABLE OLEFIN AND CATALYST THEREFOR

(75) Inventors: Jerzy Klosin, Midland, MI (US); Pulikkottil J. Thomas, Midland, MI (US); Carl N. Iverson, Houston, TX (US); Nermeen W. Aboelella, Pearland, TX (US); Kevin A. Frazier, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.
This patent is subject to a terminal disclaimer.

(21) Appl. No.: 13/814,634

(22) PCT Filed: Aug. 24, 2011

(86) PCT No.: PCT/US2011/048927
§ 371 (c)(1),
(2), (4) Date: Feb. 6, 2013

(87) PCT Pub. No.: WO2012/027448
PCT Pub. Date: Mar. 1, 2012

(65) Prior Publication Data
US 2013/0144018 A1    Jun. 6, 2013

Related U.S. Application Data

(60) Provisional application No. 61/376,717, filed on Aug. 25, 2010.

(51) Int. Cl.
*C08F 4/76* (2006.01)
*C08F 4/659* (2006.01)
(Continued)

(52) U.S. Cl.
CPC .......... *C08F 4/65912* (2013.01); *C07D 209/82* (2013.01); *C07F 7/00* (2013.01); *C08F 210/16* (2013.01); *C08F 210/18* (2013.01); *C08F 4/659* (2013.01)

(58) Field of Classification Search
CPC .................... C08F 4/64193; C08F 4/62193
USPC .......................... 526/172, 161, 348
See application file for complete search history.

(56) References Cited

U.S. PATENT DOCUMENTS 3,914,342 A    10/1975 Mitchell
6,268,444 B1    7/2001 Klosin et al.
(Continued)

FOREIGN PATENT DOCUMENTS

WO    03/040195        5/2003
WO    03/051935 A1    6/2003
(Continued)

OTHER PUBLICATIONS

PCT/US2011/048927, International Search Report, Mar. 11, 2011.
(Continued)

*Primary Examiner* — Rip A Lee

(57) ABSTRACT

The present invention generally relates to a process that copolymerizes two or more polymerizable olefins, and to cataclyst comprising a metal-ligand complex (precatalyst). The present invention also generally relates to ligands useful for preparing the metal-ligand complex.

2 Claims, 12 Drawing Sheets

(51) Int. Cl.
*C07D 209/82* (2006.01)
*C07F 7/00* (2006.01)
*C08F 210/16* (2006.01)
*C08F 210/18* (2006.01)

(56) References Cited

U.S. PATENT DOCUMENTS

| | | | |
|---|---|---|---|
| 6,841,502 B2 * | 1/2005 | Boussie et al. | 502/125 |
| 6,924,342 B2 | 8/2005 | Stevens et al. | |
| 6,953,764 B2 | 10/2005 | Frazier et al. | |
| 7,060,848 B2 * | 6/2006 | Boussie et al. | 556/54 |
| 7,241,714 B2 | 7/2007 | Boussie et al. | |
| 7,355,089 B2 | 4/2008 | Chang et al. | |
| 8,609,794 B2 * | 12/2013 | Klosin et al. | 526/172 |
| 2003/0004286 A1 | 1/2003 | Klosin et al. | |
| 2003/0204017 A1 | 10/2003 | Stevens et al. | |
| 2004/0010103 A1 | 1/2004 | Boussie et al. | |
| 2004/0014950 A1 | 1/2004 | Boussie et al. | |
| 2006/0025548 A1 | 2/2006 | Boussie et al. | |
| 2006/0199930 A1 | 9/2006 | Li Pi Shan et al. | |
| 2007/0167315 A1 | 7/2007 | Arriola et al. | |
| 2007/0167578 A1 | 7/2007 | Arriola et al. | |
| 2008/0311812 A1 | 12/2008 | Arriola et al. | |

FOREIGN PATENT DOCUMENTS

| | | |
|---|---|---|
| WO | 03091262 A1 | 11/2003 |
| WO | 04/24740 A1 | 3/2004 |
| WO | 2008033197 A2 | 3/2008 |
| WO | 2009012215 A1 | 1/2009 |

OTHER PUBLICATIONS

PCT/US2011/048927, International Preliminary Report on Patentability, Feb. 26, 2013.
PCT/US2011/048927, Written Opinion of the International Searching Authority, Feb. 26, 2013.

* cited by examiner

PROCESS FOR POLYMERIZING A POLYMERIZABLE OLEFIN AND CATALYST THEREFOR

CROSS-REFERENCE TO RELATED APPLICATIONS

This application is a non-provisional application claiming priority from the U.S. Provisional Patent Application No. 61/376,717 filed on Aug. 25, 2010, entitled "PROCESS FOR POLYMERIZING A POLYMERIZABLE OLEFIN AND CATALYST THEREFOR," the teachings of which are incorporated by reference herein, as if reproduced in full hereinbelow.

BACKGROUND OF THE INVENTION

1. Field of the Invention

The present invention generally relates to a process that copolymerizes two or more polymerizable olefins, and to a metal-ligand complex (precatalyst) and catalyst useful in such process, and to related compositions of matter, and to copolymers prepared thereby. The present invention also generally relates to ligands and intermediates useful for preparing the metal-ligand complex and to processes of their preparation. Other related inventions are described herein.

2. Description of Related Art

Polyolefins are widely used in industry. They are desirable for making, for example, containers, tubing, films and sheets for packaging, and synthetic lubricants. Examples of types of polyolefins are polyethylene polymers, poly(ethylene alpha-olefin) copolymers, and mixtures or blends of such polyolefins. Examples of commercially available polyethylene-containing polyolefins (includes mixtures or blends) are those that are commercially available from The Dow Chemical Company under the trade names DOWLEX, ATTANE, AFFINITY, ELITE, Unipol DFDA-7441 polymer, or Tuflin HS-7028; those that are available from Exxon Chemical Corporation under the trade names EXCEED and EXACT; those that are available from Mitsui Petrochemical Industries under the trade name TAFMER; those that are available from Equistar, Inc. under the trade name Petrothene GA501020 polymer; and those that are available from Nova Chemicals Corporation under the trade name Novapol TF-0 I 19-FP.

The polyolefins are prepared by a catalyzed reaction. Especially desirable would be precatalysts and catalysts that would be soluble in alkane or cycloalkane solvents so that the solutions could be used in the catalyzed reaction for preparing polyolefins acceptable for use in the food packing industry. This is there are concerns in the art about detrimental health and environmental affects of other solvents such as aromatic hydrocarbons and halogenated solvents. It has been difficult, however, to discover such a (pre)catalyst that would have activity at high reaction temperature, high comonomer incorporation into ethylene/(alpha-olefin copolymers (e.g., poly(ethylene-co-1-octene)copolymers) and solubility in alkane or cycloalkane solvents.

U.S. Pat. No. 7,241,714 B2 mentions, among other things, ligands, compositions, metal-ligand complexes and arrays with substituted bridged bis-aromatic groups that are useful for preparing ethylene/olefin copolymers. The patent also mentions methods of making and using the same in the catalysis of transformations such as the polymerization of monomers into polymers. Unfortunately, these bis(phenyl phenol)-type ligands, compositions, metal-ligand complexes and arrays do not combine high temperature activity and high comonomer incorporation and, preferably, alkane or cycloalkane solubility in one catalyst.

Chemical industry desires improved processes and catalysts for copolymerizing two or more polymerizable olefins, and improved polyolefins prepared thereby.

BRIEF SUMMARY OF THE INVENTION

The inventors have discovered that a valuable olefin copolymerization catalyst comprises a bis(phenyl phenol) ligand substituted with two ring-containing functional groups and also having a beneficial configuration of other substituents, as described later. The inventors have discovered that such catalysts are advantageously active at high reaction temperatures (e.g., greater than 150 degrees Celsius), deliver, high comonomer incorporation into ethylene/(alpha-olefin copolymers (e.g., poly(ethylene-co-1-octene)copolymers), and are soluble in alkane or cycloalkane solvents, preferably including solubility in such solvents at room temperature. Solubility of such catalysts in alkane or cycloalkane solvents (as opposed to using, for example, an aromatic hydrocarbon solvent such as toluene) at room temperature is useful for preparing a solution of such a precatalyst and catalyst at room temperature. The room temperature (pre)catalyst solution can be added to a reactor for catalyzing copolymerization of the olefins. The (pre)catalyst solution and its use also afford new chemical compatibility (e.g., ability to conduct types of olefin copolymerization reactions, or preliminary or subsequent reactions, in alkane solvents that would be incompatible or less effective if conducted in aromatic hydrocarbons or halogenated solvents. Another advantage of using the alkane or cycloalkane solvent instead of the aromatic hydrocarbons or halogenated solvents is lowering solvent costs (e.g., supply, recovery, or disposal costs) and decreasing or eliminating detrimental health and environmental impact (e.g., in terms of solvent production, negative effects of solvent residues thereof in products prepared therein, and solvent waste disposal). The present invention also generally relates to ligands and intermediates useful for preparing the metal-ligand complex and to processes of their preparation. Other related inventions are described herein. The invention process is especially useful for preparing polyolefins, including polyolefin mixtures or blends and polyolefin copolymers, including poly(ethylene alpha-olefin) copolymers.

In a first embodiment, the present invention is a process for copolymerizing polymerizable olefins (e.g., olefin monomer or olefin oligomer and olefin comonomer), the process comprising contacting together ethylene, a $(C_3-C_{40})$olefin comonomer, a first aprotic solvent, and a catalytic amount of a catalyst, wherein the catalyst is prepared before the contacting step as a solution in a second aprotic solvent and wherein the catalyst comprises a mixture or reaction product of ingredients (a) and (b), wherein ingredient (a) comprises a metal-ligand complex (also referred to herein as a precatalyst) and ingredient (b) comprises at least one activating co-catalyst (also referred to herein as an activator); (ethylene is also referred to herein as ingredient (c); and the $(C_3-C_{40})$olefin comonomer as ingredient (d));

the metal-ligand complex of ingredient (a) being at least one metal-ligand complex of formula (I):

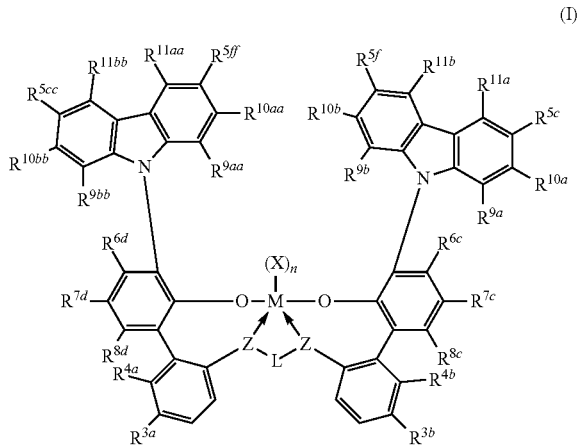

wherein:

M is a metal of any one of Groups 3 to 6 of the Periodic Table of the Elements (e.g., Group 4), the metal M being in a formal oxidation state of +2, +3, +4, +5, or +6;

n is an integer of from 0 to 5, wherein when n is 0, X is absent (i.e., $(X)_n$ is absent);

Each X independently is a monodentate ligand that is neutral, monoanionic, or dianionic; or two X are taken together to form a bidentate ligand that is neutral, monoanionic, or dianionic;

X and n are chosen in such a way that the metal-ligand complex of formula (I) is, overall, neutral;

Each Z independently is O, S, $N(C_1-C_{40})$hydrocarbyl, or $P(C_1-C_{40})$hydrocarbyl;

L is $(C_1-C_{40})$hydrocarbylene or $(C_1-C_{40})$heterohydrocarbylene, wherein the $(C_1-C_{40})$hydrocarbylene has a portion that comprises a 1-carbon atom to 18-carbon atom linker backbone, preferably a 1-carbon atom to 12 carbon atom linker, linking the Z atoms in formula (I) (to which Z atoms L is bonded) and the $(C_1-C_{40})$heterohydrocarbylene has a portion that comprises a 1-atom to 18-atom linker backbone, preferably a 1-carbon atom to 12 carbon atom linker, linking the Z atoms in formula (I), wherein each of the from 1 to 18 atoms of the 1-atom to 18-atom linker backbone of the $(C_1-C_{40})$heterohydrocarbylene independently is a carbon atom or heteroatom, wherein each heteroatom independently is O, S, S(O), $S(O)_2$, $Si(R^C)_2$, $P(R^P)$, or $N(R^N)$, wherein independently each $R^C$ independently is substituted or unsubstituted $(C_1-C_{18})$hydrocarbyl; $C_1-C_{18}$)heterohydrocarbyl; each $R^P$ independently is substituted or unsubstituted $(C_1-C_{18})$hydrocarbyl; $C_1-C_{18}$)heterohydrocarbyl; and each $R^N$ independently is substituted or unsubstituted $(C_1-C_{18})$hydrocarbyl; $C_1-C_{18}$)heterohydrocarbyl or absent (e.g., when the N to which $R^N$ is bonded as =N=);

Each of $R^{3a}$, $R^{4a}$, $R^{3b}$ and $R^{4b}$ independently is a hydrogen atom $(C_1-C_{40})$hydrocarbyl; $(C_1-C_{40})$heterohydrocarbyl; -; $Si(R^C)_3$; $O(R^C)$; $S(R^C)$; $N(R^N)_2$; $P(R^P)_2$ or halogen atom;

At least one of $R^{6c}$, $R^{7c}$, and $R^{8c}$ and at least one of $R^{6d}$, $R^{7d}$, and $R^{8d}$ independently is a $(C_2-C_{40})$hydrocarbyl; $Si(R^C)_3$ and each of the others of $R^{6c}$, $R^{7c}$, $R^{8c}$, $R^{6d}$, $R^{7d}$, and $R^{8d}$ independently is a hydrogen atom; $(C_1-C_{40})$hydrocarbyl; $(C_1-C_{40})$heterohydrocarbyl; -; $Si(R^C)_3$; $O(R^C)$; $S(R^C)$; $N(R^N)_2$; $P(R^P)_2$ or halogen atom Optionally two or more R groups (from $R^{2a}$ to $R^{8d}$) can combine together into ring structures, with such ring ring structures having from 3 to 50 atoms in the ring not couning hydrogen atoms.

At least one of $R^{5c}$ and $R^{5f}$ independently is a $(C_1-C_{40})$ hydrocarbyl; $(C_1-C_{40})$heterohydrocarbyl; -; $Si(R^C)_3$; $O(R^C)$; $S(R^C)$; $N(R^N)_2$; $P(R^P)_2$ or halogen atom; and the other of $R^{5c}$ and $R^{5f}$ independently is a hydrogen atom; $(C_1-C_{40})$hydrocarbyl; $(C_1-C_{40})$heterohydrocarbyl; -; $Si(R^C)_3$; $O(R^C)$; $S(R^C)$; $N(R^N)_2$; $P(R^P)_2$ or halogen atom At least one of $R^{5cc}$ and $R^{5ff}$ independently is a $(C_1-C_{40})$ hydrocarbyl; $(C_1-C_{40})$heterohydrocarbyl; $Si(R^C)_3$; $O(R^C)$; $S(R^C)$; $N(R^N)_2$; $P(R^P)_2$ or halogen atom; and the other of $R^{5cc}$ and $R^{5ff}$ independently is a hydrogen atom; $(C_1-C_{40})$hydrocarbyl; $(C_1-C_{40})$heterohydrocarbyl; -; $Si(R^C)_3$; $O(R^C)$; $S(R^C)$; $N(R^N)_2$; $P(R^P)_2$ or halogen atom Each of $R^{9a}$, $R^{10a}$, $R^{11a}$, $R^{9b}$, $R^{10b}$, $R^{11b}$, $R^{9aa}$, $R^{10aa}$, $R^{11aa}$, $R^{9bb}$, $R^{10bb}$ and $R^{11bb}$ independently is a hydrogen atom $(C_1-C_{40})$hydrocarbyl; $(C_1-C_{40})$heterohydrocarbyl; -; $Si(R^C)_3$; $O(R^C)$; $S(R^C)$; $N(R^N)_2$; $P(R^P)_2$ or halogen atom;

Optionally two or more carbazole R groups (e.g. $R^{9a}$, $R^{10a}$, $R^{5a}R^{1a}$, $R^{9b}$, $R^{10b}$, $R^{5f}R^{11b}$) can combine together into ring structures, with such ring ring structures having from 3 to 50 atoms in the ring not couning hydrogen atoms.

Each of the aforementioned hydrocarbyl (e.g., $R^C$, $R^N$, $R^P$, $(C_1-C_{40})$hydrocarbyl), heterohydrocarbyl (e.g., $(C_1-C_{40})$heterohydrocarbyl), hydrocarbylene (e.g., $(C_1-C_{40})$hydrocarbylene), and heterohydrocarbylene (e.g., $(C_1-C_{40})$heterohydrocarbylene) groups independently is unsubstituted or substituted with at least one substituent $R^S$ (up to and including persubstitution by $R^S$);

The sum of carbon atoms in $R^{5c}+R^{5f}+R^{7c}$ is greater than 5 carbon atoms or the sum of carbon atoms in $R^{5cc}+R^{5ff}+R^{7d}$ is greater than 5 carbon atoms; and Each $R^S$ independently is a halogen atom, polyfluoro substitution (that is one of the at least one substituent $R^S$ stands for at least two fluoro substituents, which formally replace at least two hydrogen atoms of an unsubstituted version of the substituted group), perfluoro substitution (that is the one $R^S$ stands for as many fluoro substituents as hydrogen atoms of an unsubstituted version of the substituted group that is substituted thereby), unsubstituted $(C_1-C_{18})$alkyl, $F_3C$—, $FCH_2O$—, $F_2HCO$—, $F_3CO$—, $R_3Si$—, RO—, RS—, RS(O)—, $RS(O)_2$—, $R_2P$—, $R_2N$—, $R_2C=N$—, NC—, RC(O)O—, ROC(O)—, RC(O)N(R)—, or $R_2NC(O)$—, or two of the $R^S$ are taken together to form an unsubstituted $(C_1-C_{18})$alkylene, wherein each R independently is an unsubstituted $(C_1-C_{18})$alkyl; and Wherein the ratio of total number of moles of the at least one metal-ligand complex of formula (I) to total number of moles of the at least one activating co-catalyst is from 1:10,000 to 100:1;

Wherein the contacting is performed under olefin polymerizing conditions (described later) that include a reaction temperature of from 30 degrees Celsius to 300 degrees Celsius and prepares a polyolefin copolymer comprising repeat units comprising residuals of ethylene and the $(C_3-C_{40})$olefin comonomer; and Wherein the process forms reactive chains (in situ) and is characterizable by a reaction rate constant $k_{11}$ for adding the ethylene (a monomer) to a first reactive chain end comprising an ethylene residual; a reaction rate constant $k_{12}$ for adding the $(C_3-C_{40})$olefin comonomer to a second reactive chain end comprising an ethylene residual; and a reactivity ratio $r_1$ equal to $k_{11}$ divided by $k_{12}$ of less than 20 (i.e., $r_1=k_{11}/k_{12}<20$). The term "polyolefin copolymer" means a molecule containing at least two different repeat units, wherein one of the at least two different repeat units is derived from ethylene and another from the ($C_3$-$C_{40}$)olefin comonomer. The first and second aprotic solvents can be the same or different. Preferably, each of the first and second aprotic solvents independently is a ($C_2$-$C_{40}$)alkane, ($C_3$-$C_{40}$)cycloalkane, or mixture of two or more thereof.

In a second embodiment the present invention is the catalyst comprising or prepared from the at least one metal-ligand complex of formula (I) and at least one activating co-catalyst, or a reaction product thereof (i.e., a product of a reaction of the at least one of the at least one metal-ligand complex of formula (I) with the at least one of the at least one activating co-catalyst), wherein the ratio of total number of moles of the at least one metal-ligand complex of formula (I) to total number of moles of the at least one activating co-catalyst is from 1:10,000 to 100:1. The invention also contemplates employing the invention catalyst to polymerize one polymerizable olefin (e.g., just ethylene or just a ($C_3$-$C_{40}$)olefin comonomer) to prepare a homopolymer therefrom.

The present invention also contemplates a catalyst system (i.e., a catalyst composition) comprising the aforementioned ingredients (a) and (b) and at least one additional ingredient as described later.

In another embodiment the present invention is the metal-ligand complex of formula (I).

In still another embodiment the present invention is a ligand of formula (Q):

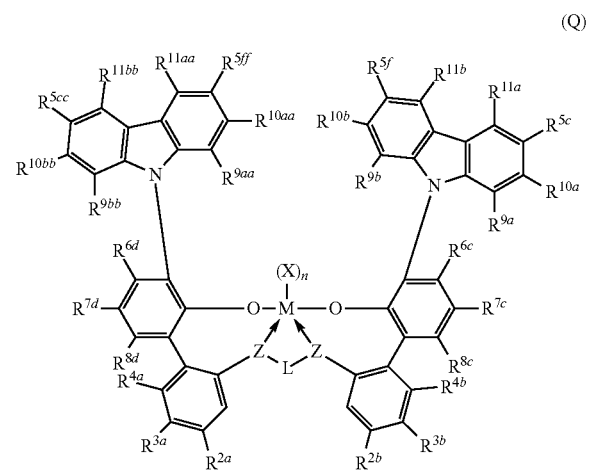

(Q)

or a Group 1 or 2 metal salt thereof, wherein the Group 1 or 2 metal of the Group 1 or 2 metal salt is a cation of any one of the metals of Groups 1 and 2 of the Periodic Table of the Elements; and L, Z, $R^{3a}$, $R^{4a}$, $R^{3b}$, $R^{4b}$, $R^{5c}$, $R^{5f}$, $R^{5cc}$, $R^{5ff}$, $R^{6c}$, $R^{7c}$, $R^{8c}$, $R^{6d}$, $R^{7d}$, $R^{8d}$, $R^{9a}$, $R^{10a}$, $R^{11a}$, $R^{9b}$, $R^{10b}$, $R^{11b}$, $R^{9aa}$, $R^{10aa}$, $R^{11aa}$, $R^{9bb}$, $R^{10bb}$ and $R^{11bb}$ are as defined previously.

The ligand of formula (Q) is useful for preparing the metal-ligand complex of formula (I). The invention also contemplates a process for preparing the metal-ligand complex of formula (I) from the ligand of formula (Q), or the Group 1 or 2 metal salt thereof, and a source of M. The invention also contemplates a process for preparing the ligand of formula (Q) or the Group 1 or 2 metal salt thereof from at least one primary intermediate as described later herein. The invention also contemplates intermediates in the preparation thereof. The processes are as described later herein.

The metal-ligand complex of formula (I) is useful in the process for preparing the invention catalyst. The invention also contemplates a process for preparing the invention catalyst from the metal-ligand complex of formula (I) and the at least one activating co-catalyst. The process is described later herein.

The invention metal-ligand complex of formula (I) and invention catalyst comprising or derived therefrom with the at least one activating co-catalyst, is useful in the invention process to prepare the polyolefin copolymer (i.e., an olefin copolymer). At least some embodiments of the invention independently are characterizable by at least one improved activity of the invention catalyst, at least one improved property of the invention polyolefin copolymer prepared thereby, an improved yield of the polyolefin copolymer in the invention process, solubility or improved solubility of the invention precatalyst or catalyst in the preferred ($C_2$-$C_{40}$)alkane or ($C_3$-$C_{40}$)cycloalkane solvent, or a combination thereof. For example, at least some embodiments of the invention are characterizable by the at least one improved activity of the invention catalyst. Also, the invention precatalyst and catalyst are believed to be soluble in the ($C_2$-$C_{40}$)alkane or ($C_3$-$C_{40}$) cycloalkane solvent as described later.

Without being bound by theory, the inventors discovered the bis(phenyl phenol) ligand having a combination of substituents that includes two carbazolyl substituents that further contain at least one, preferably two substituents in the 3- or 6-position(s) of each carbazolyl; and also the bis(phenyl phenol) ligand having an alkane/cycloalkane solubilizing group at $R^{6c}$, $R^{7c}$, or $R^{8c}$ and another alkane/cycloalkane solubilizing group at $R^{6d}$, $R^{7d}$, or $R^{8d}$ described above in the metal-ligand complex of formula (I), and lacking substituents between Z and $R^{3a}$ and Z and $R^{3b}$ on the phenyl ether rings of the bis(phenyl phenol) ligand. They discovered that this combination leads to the invention precatalysts and catalysts derived therefrom that are characterizable as advantageously having the desired combination of features, namely increased catalytic activity in the invention process at a high reaction temperature (e.g., 130 degrees Celsius (° C.) or greater), and a high degree of ($C_3$-$C_{40}$)olefin comonomer incorporation, and, preferably solubility in the ($C_2$-$C_{40}$)alkane or ($C_3$-$C_{40}$) cycloalkane solvent. As will be seen later with comparative examples, placing any substituent group on the phenyl ether rings between $R^{3a}$ and Z or between $R^{3b}$ and Z, is detrimental and eliminates the combination of features by causing comonomer incorporation to undesirably decrease (i.e., causes $r_1$ to undesirably increase to $r_1$>30, even $r_1$>40, or $r_1$>50). Thus, the invention discovered that the alkane/cycloalkane solubilizing groups afford the desired high comonomer incorporation and solubility in alkane/cycloalkane solvents when those groups are located at $R^{6c}$, $R^{7c}$, or $R^{8c}$ and $R^{6d}$, $R^{7d}$, or $R^{8d}$, but not when such a group or any group is located between $R^{3a}$ and Z and/or between $R^{3b}$ and Z in formula (I).

Another advantage is that in some embodiments the invention process of the first embodiment functions as a process, preferably a continuous process, that is capable of preparing in some embodiments new polyolefins (e.g., new polyolefin polymer blends or mixtures or new polyolefin copolymers). Thus, the present invention also contemplates new polyolefins (e.g., polyolefin copolymers) prepared by the invention process.

The polyolefins, including polyolefin copolymers, prepared by the invention process are useful in numerous applications such as, for example, synthetic lubricants and, especially for the OBCs, elastic films for hygiene applications (e.g., for diaper covers); flexible molded goods for appliances, tools, consumer goods (e.g., toothbrush handles), sporting goods, building and construction components, automotive parts, and medical applications (e.g., medical devices); flexible gaskets and profiles for appliance (e.g., refrigerator door gaskets and profiles), building and construction, and automotive applications; adhesives for packaging (e.g., for use in manufacturing corrugated cardboard boxes), hygiene applications, tapes, and labels; and foams for sporting goods (e.g., foam mats), packaging, consumer goods, and automotive applications.

Additional embodiments are described in the remainder of the specification, including the claims.

BRIEF DESCRIPTION OF THE DRAWING(S)

Some embodiments of the present invention are described herein in relation to the accompanying drawing(s), which will at least assist in illustrating various features of the embodiments.

DETAILED DESCRIPTION OF THE INVENTION

Figure 1:
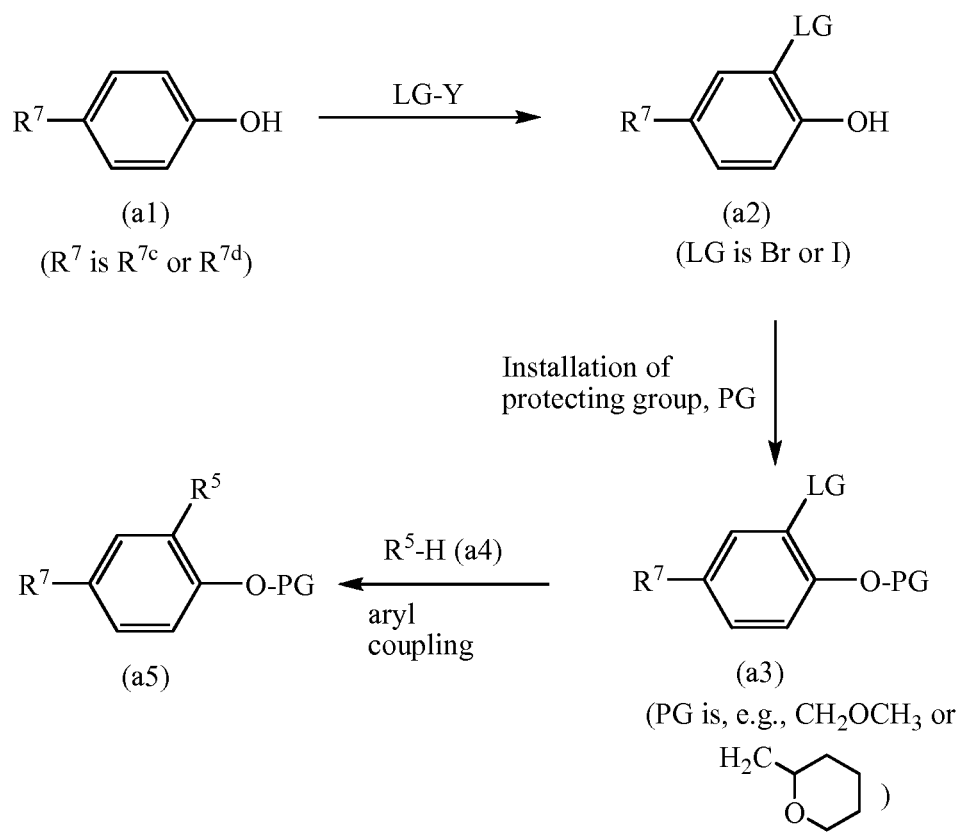
FIG. 1 shows an illustrative procedure for preparing a first primary intermediate useful in a convergent synthesis of the ligand of formula (Q).

The present invention generally relates to a process that copolymerizes two or more polymerizable olefins, and to a metal-ligand complex (precatalyst) and catalyst useful in such process, and to related compositions of matter and to copolymers prepared thereby. The present invention also generally relates to ligands and intermediates useful for preparing the metal-ligand complex and to processes of their preparation. Other related inventions are described herein The various embodiments of the present invention that are summarized previously are incorporated here by reference.

The invention process of the first embodiment is versatile. For example, in some embodiments the invention process employs three or more polymerizable olefins and such invention process prepares, and the polyolefin copolymer is, a polyolefin copolymer prepared by copolymerizing the three or more polymerizable olefins. In other examples of the versatility of the invention process of the first embodiment, in some embodiments the invention process further employs a molecular weight control agent (e.g., hydrogen gas) so as to prepare a molecular weight-controlled polyolefin (e.g., molecular weight-controlled polyolefin copolymer) as described later.

In some embodiments the invention process can be adapted as described later to further employ a combination of a chain shuttling agent (CSA) and a non-invention ethylene selective polymerization catalyst (i.e., non-invention ethylene selective catalyst) with a ($C_3$-$C_{40}$)olefin comonomer that is a ($C_3$-$C_{40}$)alpha-olefin. These embodiments preferably prepare the polyolefin copolymer as a poly(ethylene alpha-olefin), especially a poly(ethylene alpha-olefin) block copolymer, which has hard and soft segments. The soft segments are prepared by the invention catalyst and the hard segments by the non-invention ethylene selective polymerization catalyst. The hard segment is a polyethylene segment and is sometimes referred to herein as a polyethylene hard segment.

In some embodiments the invention process can be adapted as described later to prepare a polyolefin copolymer-containing blend or mixture.

The invention also contemplates embodiments of the catalyst system, wherein, for example, the at least one additional ingredient is ingredient (c) (i.e., ethylene); ingredient (d) (i.e., ($C_3$-$C_{40}$)olefin comonomer); a molecular weight control agent (e.g., a CSA) as an ingredient (e); a non-invention ethylene-selective polymerization catalyst as an ingredient (f); or a combination thereof. Ingredients (d), (e) and (f) are described later. In some embodiments the at least one additional ingredient comprises the ($C_2$-$C_{40}$)alkane or ($C_3$-$C_{40}$)cycloalkane solvent, wherein ingredients (a) and (b) are dissolved therein.

In other examples of the versatility of the invention process of the first embodiment, the polyolefin copolymer can be separated, if desired, from any remaining (unpolymerized) polymerizable olefin(s) by conventional means (e.g., filtering/washing the polyolefin copolymer material or stripping or evaporating of the polymerizable olefin(s). The invention process works with any mole ratio of the two or more polymerizable olefins.

Further the polyolefins prepared by the invention process typically contain vinyl groups. The invention also contemplates modified polymers prepared by functionalizing by known means such vinyl groups to give polar group functionalized derivatives thereof. If desired the polar group functionalized derivatives can be reacted with complimentary-reacting monomers or oligomers so as to form polar group functionalized copolymers. In some embodiments the functionalizing chemistry is incompatible with aromatic hydrocarbon solvents or halogenated solvents and is compatible with the ($C_2$-$C_{40}$)alkane or ($C_3$-$C_{40}$)cycloalkane solvent.

For purposes of United States patent practice and other patent practices allowing incorporation of subject matter by reference, the entire contents—unless otherwise indicated—of each U.S. patent, U.S. patent application, U.S. patent application publication, PCT international patent application and WO publication equivalent thereof, referenced in the instant Summary or Detailed Description of the Invention are hereby incorporated by reference. In an event where there is a conflict between what is written in the present specification and what is written in a patent, patent application, or patent application publication, or a portion thereof that is incorporated by reference, what is written in the present specification controls.

In the present application, any lower limit of a range of numbers, or any preferred lower limit of the range, may be combined with any upper limit of the range, or any preferred upper limit of the range, to define a preferred aspect or embodiment of the range. Each range of numbers includes all numbers, both rational and irrational numbers, subsumed within that range (e.g., the range from about 1 to about 5 includes, for example, 1, 1.5, 2, 2.75, 3, 3.80, 4, and 5).

Any headings herein are used only for convenience of the reader and do not limit, and should not be interpreted as limiting, the present invention.

Unless otherwise noted, the phrase "Periodic Table of the Elements" refers to the official periodic table, version dated Jun. 22, 2007, published by the International Union of Pure and Applied Chemistry (IUPAC). Also any references to a Group or Groups shall be to the Group or Groups reflected in this Periodic Table of the Elements.

Where the invention, or a portion thereof (e.g., element or step), is defined in the alternative by a Markush group having two or more members, the invention contemplates preferred embodiments too numerous to recite each one herein. For convenience, such preferred embodiments can be readily determined by: (i) selecting any single member from the Markush group, thereby limiting scope of the Markush group to the selected single member thereof; or (ii) deleting any single member from the Markush group, thereby limiting the Markush group to any one of the remaining member(s) thereof. In some embodiments the member that is selected or deleted is based on one of the Examples or other species of the present invention described herein.

Certain unsubstituted chemical groups or olefin monomers are described herein as having a maximum number of 40 carbon atoms (e.g., $(C_1-C_{40})$hydrocarbyl and $(C_1-C_{40})$heterohydrocarbyl). The forty carbon atom upper limit in such groups or olefins is a practical upper limit. Nevertheless in some embodiments the invention contemplates such unsubstituted chemical groups having a maximum number of carbon atoms that is higher than 40 (e.g., 60, 100, 1000, or greater than 1000).

The word "optionally" means "with or without." For example, "optionally, an additive" means with or without an additive.

In an event where there is a conflict between a compound name and its structure, the structure controls.

In an event where there is a conflict between a unit value that is recited without parentheses, e.g., 2 inches, and a corresponding unit value that is parenthetically recited, e.g., (5 centimeters), the unit value recited without parentheses controls.

As used herein, "a," "an," and "the," are used following an open-ended term such as comprising to mean "at least one." In any aspect or embodiment of the instant invention described herein, the term "about" in a phrase referring to a numerical value may be deleted from the phrase to give another aspect or embodiment of the instant invention. In the former aspects or embodiments employing the term "about," meaning of "about" can be construed from context of its use. Preferably "about" means from 90 percent to 100 percent of the numerical value, from 100 percent to 110 percent of the numerical value, or from 90 percent to 110 percent of the numerical value. In any aspect or embodiment of the instant invention described herein, the open-ended terms "comprising," "comprises," and the like (which are synonymous with "including," "having," and "characterized by") may be replaced by the respective partially closed phrases "consisting essentially of," "consists essentially of," and the like or the respective closed phrases "consisting of," "consists of," and the like to give another aspect or embodiment of the instant invention. The partially closed phrases such as "consisting essentially of" and the like limits scope of a claim to materials or steps recited therein and those that do not materially affect the basic and novel characteristic(s) of the claimed invention. The term "characterizable" is open-ended and means distinguishable.

In the present application, when referring to a preceding list of elements (e.g., ingredients), the phrases "mixture thereof," "combination thereof," and the like mean any two or more, including all, of the listed elements. The term "or" used in a listing of members, unless stated otherwise, refers to the listed members individually as well as in any combination, and supports additional embodiments reciting any one of the individual members (e.g., in an embodiment reciting the phrase "10 percent or more," the "or" supports another embodiment reciting "10 percent" and still another embodiment reciting "more than 10 percent."). The term "plurality" means two or more, wherein each plurality is independently selected unless indicated otherwise. The terms "first," "second," et cetera serve as a convenient means of distinguishing between two or more elements or limitations (e.g., a first chair and a second chair) and do not imply quantity or order unless specifically so indicated. The symbols "≤" and "≥" respectively mean less than or equal to and greater than or equal to. The symbols "<" and ">" respectively mean less than and greater than.

As used herein the term "poly(ethylene alpha-olefin) block copolymer" is used interchangeably herein with the terms "olefin block copolymer," "OBC," "ethylene/α-olefin block interpolymer," and "ethylene/α-olefin block copolymer". The terms "alpha-olefin" and "α-olefin" are used interchangeably herein. The term "ethylene" means ethene, i.e., $H_2C=CH_2$.

As mentioned before, the invention process employs at least one metal-ligand complex of formula (I), which is described herein using conventional chemical group terminology. When used to describe certain carbon atom-containing chemical groups (e.g., $(C_1-C_{40})$alkyl), the parenthetical expression $(C_1-C_{40})$ and like expressions can be generically represented by the form "$(C_x-C_y)$," which means that the unsubstituted version of the chemical group comprises from a number x carbon atoms to a number y carbon atoms, wherein each x and y independently is an integer as described for the chemical group. The $R^S$ substituted version of the chemical group can contain more than y carbon atoms depending on nature of $R^S$. Thus, for example, an unsubstituted $(C_1-C_{40})$alkyl contains from 1 to 40 carbon atoms (x=1 and y=40). When the chemical group is substituted by at least one carbon atom-containing $R^S$ substituent, the substituted $(C_x-C_y)$ chemical group may comprise more than y total carbon atoms; i.e., the total number of carbon atoms of the carbon atom-containing substituent(s)-substituted $(C_x-C_y)$ chemical group is equal to y plus the sum of the number of carbon atoms of each of the carbon atom-containing substituent(s). Any atom of a chemical group that is not specified herein is understood to be a hydrogen atom.

In some embodiments, each of the chemical groups (e.g., X, L, $R^{3a}$, etc.) of the metal-ligand complex of formula (I) is unsubstituted, that is, can be defined without use of a substituent $R^S$. In other embodiments, at least one of the chemical groups of the metal-ligand complex of formula (I) independently contain at least one substituent $R^S$. Preferably, accounting for all chemical groups, there are not more than a total of 20 $R^S$, more preferably not more than a total of 10 $R^S$, and still more preferably not more than a total of 5 $R^S$ in the metal-ligand complex of formula (I). Where the invention compound contains two or more substituents $R^S$, each $R^S$ independently is bonded to a same or different substituted chemical group. When two or more $R^S$ are bonded to a same chemical group, they independently are bonded to a same or different carbon atom or heteroatom, as the case may be, in the same chemical group up to and including persubstitution of the chemical group.

The term "persubstitution" means each hydrogen atom (H) bonded to a carbon atom or heteroatom of a corresponding unsubstituted compound or functional group, as the case may be, is replaced by a substituent (e.g., $R^S$). The term "polysubstitution" means each of at least two, but not all, hydrogen atoms (H) bonded to carbon atoms or heteroatoms of a corresponding unsubstituted compound or functional group, as the case may be, is replaced by a substituent (e.g., $R^S$). In some embodiments, at least one $R^S$ is polyfluoro substitution or perfluoro substitution. For present purposes "polyfluoro substitution" and "perfluoro substitution" each count as one $R^S$ substituent. The term "poly" as in "polyfluoro substitution" means that two or more H, but not all H, bonded to carbon atoms of a corresponding unsubstituted chemical group are replaced by a fluoro in the substituted chemical group. Preferably "poly" as used in polysubstitution and polyfluorosubstitution means two substituents (e.g., two fluorine atoms). The term "per" as in "perfluoro substitution" means each H bonded to carbon atoms of a corresponding unsubstituted chemical group is replaced by a fluoro in the substituted chemical group. In some embodiments each $R^S$ independently is selected from a group consisting of a halogen atom and any one of polyfluoro substitution, unsubstituted $(C_1-C_{18})$alkyl, $F_3C$—, $FCH_2O$—, $F_2HCO$—, $F_3CO$—, $R_3Si$—, $RO$—, $RS$—, $RS(O)$—, $RS(O)_2$—, $R_2P$—, $R_2N$—, $R_2C=N$—, $NC$—, $RC(O)O$—, $ROC(O)$—, $RC(O)N(R)$—, and $R_2NC(O)$—, wherein each R independently is an unsubstituted $(C_1-C_{18})$alkyl. In some embodiments each $R^S$ independently is selected from a group consisting of a halogen atom, unsubstituted $(C_1-C_{18})$alkyl, and any one of polyfluoro substitution, $F_3C$—, $FCH_2O$—, $F_2HCO$—, $F_3CO$—, $R_3Si$—, $RO$—, $RS$—, $RS(O)$—, $RS(O)_2$—, $R_2P$—, $R_2N$—, $R_2C=N$—, $NC$—, $RC(O)O$—, $ROC(O)$—, $RC(O)N(R)$—, and $R_2NC(O)$—. In some embodiments each $R^S$ independently is selected from a group consisting of an unsubstituted $(C_1-C_{18})$alkyl and any one of $F_3C$—, $FCH_2O$—, $F_2HCO$—, $F_3CO$—, $R_3Si$—, $RO$—, $RS$—, $RS(O)$—, $RS(O)_2$—, $R_2P$—, $R_2N$—, $R_2C=N$—, $NC$—, $RC(O)O$—, $ROC(O)$—, $RC(O)N(R)$—, and $R_2NC(O)$—. In some embodiments two $R^S$ are taken together to form an unsubstituted $(C_1-C_{18})$alkylene. Still more preferably substitutents $R^S$ independently are unsubstituted $(C_1-C_{18})$alkyl, F, unsubstituted $(C_1-C_{18})$alkylene, or a combination thereof; and even more preferably unsubstituted $(C_1-C_8)$alkyl or unsubstituted $(C_1-C_8)$alkylene. The $(C_1-C_{18})$alkylene and $(C_1-C_8)$alkylene substituents are especially useful for forming substituted chemical groups that are bicyclic or tricyclic analogs, as the case may be, of corresponding monocyclic or bicyclic unsubstituted chemical groups.

As used herein, the term "$(C_1-C_{40})$hydrocarbyl" means a hydrocarbon radical of from 1 to carbon atoms and the term "$(C_1-C_{40})$hydrocarbylene" means a hydrocarbon diradical of from 1 to 40 carbon atoms, wherein each hydrocarbon radical and diradical independently is aromatic (6 carbon atoms or more) or non-aromatic, saturated or unsaturated, straight chain or branched chain, cyclic (including mono- and polycyclic, fused and non-fused polycyclic, including bicyclic; 3 carbon atoms or more) or acyclic, or a combination of two or more thereof; and each hydrocarbon radical and diradical independently is the same as or different from another hydrocarbon radical and diradical, respectively, and independently is unsubstituted or substituted by at least one $R^S$. The radicals of the diradical can be on same or different type of carbon atoms (e.g., both on saturated acyclic carbon atoms or one on an acyclic carbon atom and one on aromatic carbon atom). Other hydrocarbyl and hydrocarbylene groups (e.g., $(C_2-C_{12})$hydrocarbylene)) are defined in an analogous manner.

Preferably, a $(C_1-C_{40})$hydrocarbyl independently is an unsubstituted or substituted $(C_1-C_{40})$alkyl, $(C_3-C_{40})$cycloalkyl, $(C_3-C_{20})$cycloalkyl-$(C_1-C_{20})$alkylene, $(C_6-C_{40})$aryl, or $(C_6-C_{20})$aryl-$(C_1-C_{20})$alkylene. More preferably, each of the aforementioned $(C_1-C_{40})$hydrocarbyl groups independently has a maximum of 20 carbon atoms (i.e., $(C_1-C_{20})$hydrocarbyl), and still more preferably a maximum of 12 carbon atoms.

The terms "$(C_1-C_{40})$alkyl" and "$(C_1-C_{18})$alkyl" mean a saturated straight or branched hydrocarbon radical of from 1 to 40 carbon atoms or from 1 to 18 carbon atoms, respectively, that is unsubstituted or substituted by at least one $R^S$. Other alkyl groups (e.g., $(C_1-C_{12})$alkyl)) are defined in an analogous manner. Preferably, $(C_1-C_{40})$alkyl has a maximum of 20 carbon atoms (i.e., $(C_1-C_{20})$alkyl), more preferably 12 carbon atoms, and still more preferably 8 carbon atoms. Examples of unsubstituted $(C_1-C_{40})$alkyl are unsubstituted $(C_1-C_{20})$alkyl; unsubstituted $(C_1-C_{10})$alkyl; unsubstituted $(C_1-C_5)$alkyl; methyl; ethyl; 1-propyl; 2-propyl; 1-butyl; 2-butyl; 2-methylpropyl; 1,1-dimethylethyl; 1-pentyl; 1-hexyl; 1-heptyl; 1-nonyl; and 1-decyl. Examples of substituted $(C_1-C_{40})$alkyl are substituted $(C_1-C_{20})$alkyl, substituted $(C_1-C_{10})$alkyl, trifluoromethyl, and $(C_{45})$alkyl. The $(C_{45})$alkyl is, for example, a $(C_{27}-C_{40})$alkyl substituted by one $R^S$, which is a $(C_{18}-C_5)$alkyl, respectively. Preferably, each $(C_1-C_5)$alkyl independently is methyl, trifluoromethyl, ethyl, 1-propyl, 2-methylethyl, or 1,1-dimethylethyl.

The term "$(C_6-C_{40})$aryl" means an unsubstituted or substituted (by at least one $R^S$) mono-, bi- or tricyclic aromatic hydrocarbon radical of from 6 to 40, preferably from 6 to 14, ring carbon atoms, and the mono-, bi- or tricyclic radical comprises 1, 2 or 3 rings, respectively, wherein the 1 ring is aromatic; at least one of the 2 or 3 rings is aromatic; and the 2 or 3 rings independently are fused or non-fused. Other aryl groups (e.g., $(C_6-C_{10})$aryl)) are defined in an analogous manner. Preferably, $(C_6-C_{40})$aryl has a maximum of 20 carbon atoms (i.e., $(C_6-C_{20})$aryl), more preferably 18 carbon atoms, still more preferably 10 carbon atoms, and even more preferably 6 carbon atoms. Examples of unsubstituted $(C_6-C_{40})$aryl are unsubstituted $(C_6-C_{20})$aryl; unsubstituted $(C_6-C_{18})$aryl; phenyl; $(C_3-C_6)$cycloalkyl-phenyl; fluorenyl; tetrahydrofluorenyl; indacenyl; hexahydroindacenyl; indenyl; dihydroindenyl; naphthyl; tetrahydronaphthyl; and phenanthrene. Examples of substituted $(C_6-C_{40})$aryl are substituted $(C_6-C_{20})$aryl; substituted $(C_6-C_{18})$aryl; 2-$(C_1-C_5)$alkyl-phenyl; 2,4-bis$(C_1-C_5)$alkyl-phenyl; 2,4-bis[$(C_{20})$alkyl]-phenyl; polyfluorophenyl; pentafluorophenyl; and fluoren-9-one-1-yl.

The term "$(C_3-C_{40})$cycloalkyl" means a saturated cyclic hydrocarbon radical of from 3 to carbon atoms that is unsubstituted or substituted by at least one $R^S$. Other cycloalkyl groups (e.g., $(C_3-C_{12})$alkyl)) are defined in an analogous manner. Preferably, $(C_3-C_{40})$cycloalkyl has a maximum of 20 carbon atoms (i.e., $(C_3-C_{30})$cycloalkyl), more preferably 10 carbon atoms, and still more preferably 6 carbon atoms. Examples of unsubstituted $(C_3-C_{40})$cycloalkyl are unsubstituted $(C_3-C_{20})$cycloalkyl, unsubstituted $(C_3-C_{10})$cycloalkyl, cyclopropyl, cyclobutyl, cyclopentyl, cyclohexyl, cycloheptyl, cyclooctyl, cyclononyl, and cyclodecyl. Examples of substituted $(C_3-C_{40})$cycloalkyl are substituted $(C_3-C_{20})$cycloalkyl, substituted $(C_3-C_{10})$cycloalkyl, cyclopentanon-2-yl, and 1-fluorocyclohexyl.

Examples of $(C_1-C_{40})$hydrocarbylene are unsubstituted or substituted $(C_6-C_{40})$arylene, $(C_3-C_{40})$cycloalkylene, and $(C_1-C_{40})$alkylene (e.g., $(C_1-C_{20})$alkylene). In some embodiments, the diradicals are on a same carbon atom (e.g., —CH$_2$—) or on adjacent carbon atoms (i.e., 1,2-diradicals), or are spaced apart by one, two, etc. intervening carbon atoms (e.g., respective 1,3-diradicals, 1,4-diradicals, etc.). Preferred is a 1,2-, 1,3-, 1,4-, or an alpha,omega-diradical, and more preferably a 1,2-diradical. The alpha,omega-diradical is a diradical that has a maximum carbon backbone spacing between the radical carbons. More preferred is a 1,2-diradical version of $(C_6-C_{18})$arylene, $(C_3-C_{20})$cycloalkylene, or $(C_2-C_{20})$alkylene; a 1,3-diradical version of $(C_6-C_{18})$arylene, $(C_4-C_{20})$cycloalkylene, or $(C_3-C_{20})$alkylene; or a 1,4-diradical version of $(C_6-C_{18})$arylene, $(C_6-C_{20})$cycloalkylene, or $(C_4-C_{20})$alkylene.

The term "$(C_1-C_{40})$alkylene" means a saturated straight chain or branched chain diradical (i.e., the radicals are not on ring atoms) of from 1 to 40 carbon atoms that is unsubstituted or substituted by at least one $R^S$. Other alkylene groups (e.g., $(C_1-C_{12})$alkylene)) are defined in an analogous manner. Examples of unsubstituted $(C_1-C_{40})$alkylene are unsubstituted $(C_1-C_{20})$alkylene, including unsubstituted 1,2-$(C_2-C_{10})$alkylene; 1,3-$(C_3-C_{10})$alkylene; 1,4-$(C_4-C_{10})$alkylene; —CH$_2$—, —CH$_2$CH$_2$—, —(CH$_2$)$_3$—, —CH$_2$CHCH$_3$, —(CH$_2$)$_4$—, —(CH$_2$)$_5$—, —(CH$_2$)$_6$—, —(CH$_2$)$_7$—, —(CH$_2$)$_8$—, and —(CH$_2$)$_4$C(H)(CH$_3$)—. Examples of substituted $(C_1-C_{40})$alkylene are substituted $(C_1-C_{20})$alkylene, —CF$_2$—, —C(O)—, and —(CH$_2$)$_{14}$C(CH$_3$)$_2$(CH$_2$)$_5$— (i.e., a 6,6-dimethyl substituted normal-1,20-eicosylene). Since as mentioned previously two $R^S$ may be taken together to form a $(C_1-C_{18})$alkylene, examples of substituted $(C_1-C_{40})$alkylene also include 1,2-bis(methylene)cyclopentane, 1,2-bis(methylene)cyclohexane, 2,3-bis(methylene)-7,7-dimethyl-bicyclo[2.2.1]heptane, and 2,3-bis(methylene)bicyclo[2.2.2]octane.

The term "$(C_3-C_{40})$cycloalkylene" means a cyclic diradical (i.e., the radicals are on ring atoms) of from 3 to 40 carbon atoms that is unsubstituted or substituted by at least one $R^S$. Examples of unsubstituted $(C_3-C_{40})$cycloalkylene are 1,3-cyclopropylene, 1,1-cyclopropylene, and 1,2-cyclohexylene. Examples of substituted $(C_3-C_{40})$cycloalkylene are 2-oxo-1,3-cyclopropylene and 1,2-dimethyl-1,2-cyclohexylene.

The term "$(C_1-C_{40})$heterohydrocarbyl" means a heterohydrocarbon radical of from 1 to 40 carbon atoms and the term "$(C_1-C_{40})$heterohydrocarbylene means a heterohydrocarbon diradical of from 1 to 40 carbon atoms, and each heterohydrocarbon independently has at least one heteroatom B($R^C$) O; S; S(O); S(O)$_2$; Si($R^C$)$_2$; Ge($R^C$)$_2$; P($R^P$); and N($R^N$), wherein independently each $R^C$ is unsubstituted $(C_1-C_{18})$hydrocarbyl, each $R^P$ is unsubstituted $(C_1-C_{18})$hydrocarbyl; and each $R^N$ is unsubstituted $(C_1-C_{18})$hydrocarbyl or absent (e.g., absent when N comprises —N= or tri-carbon substituted N). The radicals of the diradical can be on same or different type of atoms (e.g., both on saturated acyclic atoms or one on an acyclic atom and one on aromatic atom). Other heterohydrocarbyl (e.g., $(C_1-C_{12})$ heterohydrocarbyl)) and heterohydrocarbylene groups are defined in an analogous manner. Preferably, the heteroatom(s) is O; S; S(O); S(O)$_2$; Si($R^C$)$_2$; P($R^P$); or N($R^N$). The heterohydrocarbon radical and each of the heterohydrocarbon diradicals independently is on a carbon atom or heteroatom thereof, although preferably is on a carbon atom when bonded to a heteroatom in formula (I) or to a heteroatom of another heterohydrocarbyl or heterohydrocarbylene. Each $(C_1-C_{40})$heterohydrocarbyl and $(C_1-C_{40})$heterohydrocarbylene independently is unsubstituted or substituted (by at least one $R^S$), aromatic or non-aromatic, saturated or unsaturated, straight chain or branched chain, cyclic (including mono- and poly-cyclic, fused and non-fused polycyclic) or acyclic, or a combination of two or more thereof; and each is respectively the same as or different from another.

Preferably, the $(C_1-C_{40})$heterohydrocarbyl independently is unsubstituted or substituted $(C_1-C_{40})$heteroalkyl, $(C_1-C_{40})$hydrocarbyl-B($R^C$)—, $(C_1-C_{40})$hydrocarbyl-O—, $(C_1-C_{40})$hydrocarbyl-S—, $(C_1-C_{40})$hydrocarbyl-S(O)—, $(C_1-C_{40})$hydrocarbyl-S(O)$_2$—, $(C_1-C_{40})$hydrocarbyl-Si($R^C$)$_2$—, $(C_1-C_{40})$hydrocarbyl-Ge($R^C$)$_2$—, $(C_1-C_{40})$hydrocarbyl-N($R^N$)—, $(C_1-C_{40})$hydrocarbyl-P($R^P$)—, $(C_1-C_{40})$hydrocarbyl-P($R^P$)—$(C_1-C_{20})$alkylene-S—, $(C_2-C_{40})$heterocycloalkyl, $(C_2-C_{19})$heterocycloalkyl-$(C_1-C_{20})$alkylene, $(C_3-C_{20})$cycloalkyl-$(C_1-C_{19})$heteroalkylene, $(C_2-C_{19})$heterocycloalkyl-$(C_1-C_{20})$heteroalkylene, $(C_1-C_{40})$heteroaryl, $(C_1-C_{19})$heteroaryl-$(C_1-C_{20})$alkylene, $(C_6-C_{20})$aryl-$(C_1-C_{19})$heteroalkylene, or $(C_1-C_{19})$heteroaryl-$(C_1-C_{20})$heteroalkylene. More preferably, each of the aforementioned groups has a maximum of 20 carbon atoms (not counting carbon atoms from any $R^S$).

The term "$(C_1-C_{40})$heteroaryl" means an unsubstituted or substituted (by at least one $R^S$) mono-, bi- or tricyclic heteroaromatic hydrocarbon radical of from 1 to 40 total carbon atoms and from 1 to 4 heteroatoms; from 1 to 44 total ring atoms, preferably from 5 to 10 total ring atoms, and the mono-, bi- or tricyclic radical comprises 1, 2 or 3 rings, respectively, wherein the 1-ring is heteroaromatic; at least one of the 2 or 3 rings is heteroaromatic; and the 2 or 3 rings independently are fused or non-fused. Other heteroaryl groups (e.g., $(C_1-C_{12})$heteroaryl)) are defined in an analogous manner. The monocyclic heteroaromatic hydrocarbon radical is a 5-membered or 6-membered ring. The 5-membered ring has from 1 to 4 carbon atoms and from 4 to 1 heteroatoms, respectively, each heteroatom being O, S, N, or P, and preferably O, S, or N. Examples of 5-membered ring heteroaromatic hydrocarbon radical are pyrrol-1-yl; pyrrol-2-yl; furan-3-yl; thiophen-2-yl; pyrazol-1-yl; isoxazol-2-yl; isothiazol-5-yl; imidazol-2-yl; oxazol-4-yl; thiazol-2-yl; 1,2,4-triazol-1-yl; 1,3,4-oxadiazol-2-yl; 1,3,4-thiadiazol-2-yl; tetrazol-1-yl; tetrazol-2-yl; and tetrazol-5-yl. The 6-membered ring has 4 or 5 carbon atoms and 2 or 1 heteroatoms, the heteroatoms being N or P, and preferably N. Examples of 6-membered ring heteroaromatic hydrocarbon radical are pyridine-2-yl; pyrimidin-2-yl; and pyrazin-2-yl. The bicyclic heteroaromatic hydrocarbon radical preferably is a fused 5,6- or 6,6-ring system. Examples of the fused 5,6-ring system bicyclic heteroaromatic hydrocarbon radical are indol-1-yl; and benzimidazole-1-yl. Examples of the fused 6,6-ring system bicyclic heteroaromatic hydrocarbon radical are quinolin-2-yl; and isoquinolin-1-yl. The tricyclic heteroaromatic hydrocarbon radical preferably is a fused 5,6,5-; 5,6,6-; 6,5,6-; or 6,6,6-ring system. An example of the fused 5,6,5-ring system is 1,7-dihydropyrrolo[3,2-J]indol-1-yl. An example of the fused 5,6,6-ring system is 1H-benzo[f]indol-1-yl. An example of the fused 6,5,6-ring system is 9H-carbazol-9-yl, which may also be named as a dibenzo-1H-pyrrole-1-yl. An example of the fused 6,5,6-ring system is 9H-carbazol-9-yl. An example of the fused 6,6,6-ring system is acrydin-9-yl. The 5-membered rings and 6-membered rings of the fused 5,6-; 6,6-; 5,6,5-; 5,6,6-; 6,5,6-; and 6,6,6-ring systems independently can be as described above for 5-membered and 6-membered rings, respectively, except where the ring fusions occur.

The aforementioned heteroalkyl and heteroalkylene groups are saturated straight or branched chain radicals or diradicals, respectively, containing $(C_1-C_{40})$ carbon atoms, or fewer carbon atoms as the case may be, and at least one heteroatom (up to 4 heteroatoms) $Si(R^C)_2$, $Ge(R^C)_2$, $P(R^P)$, $N(R^N)$, N, O, S, S(O), and $S(O)_2$ as defined above, wherein each of the heteroalkyl and heteroalkylene groups independently are unsubstituted or substituted by at least one RS.

The term "$(C_2-C_{40})$heterocycloalkyl" means a cyclic diradical (i.e., the radicals are on ring atoms) of from 2 to 40 carbon atoms and from 1 to 4 heteroatoms, as described previously, that is unsubstituted or substituted by at least one $R^S$. Examples of unsubstituted $(C_2-C_{40})$heterocycloalkyl are unsubstituted $(C_2-C_{20})$heterocycloalkyl, unsubstituted $(C_2-C_{10})$heterocycloalkyl, aziridin-1-yl, oxetan-2-yl, tetrahydrofuran-3-yl, pyrrolidin-1-yl, tetrahydrothiophen-S,S-dioxide-2-yl, morpholin-4-yl, 1,4-dioxan-2-yl, hexahydroazepin-4-yl, 3-oxa-cyclooctyl, 5-thia-cyclononyl, and 2-aza-cyclodecyl.

The term "halogen atom" means fluorine atom (F), chlorine atom (Cl), bromine atom (Br), or iodine atom (I) radical. Preferably each halogen atom independently is the Br, F, or Cl radical, and more preferably the F or Cl radical. The term "halide" means fluoride (F⁻), chloride (Cl⁻), bromide (Br⁻), or iodide (I⁻) anion. Preferably, halide is Cl⁻ or Br⁻.

Unless otherwise indicated herein the term "heteroatom" means O, S, S(O), $S(O)_2$, $Si(R^C)_2$, $P(R^P)$, or $N(R^N)$, wherein independently each RC is unsubstituted $(C_1-C_{18})$hydrocarbyl, each $R^P$ is unsubstituted $(C_1-C_{18})$hydrocarbyl; and each $R^N$ is unsubstituted $(C_1-C_{18})$hydrocarbyl or absent (absent when N comprises —N=).

Preferably, there are no O—O, S—S, or O—S bonds, other than O—S bonds in an S(O) or $S(O)_2$ diradical functional group, in the metal-ligand complex of formula (I). More preferably, there are no O—O, N—N, P—P, N—P, S—S, or O—S bonds, other than O—S bonds in an S(O) or $S(O)_2$ diradical functional group, in the metal-ligand complex of formula (I).

The term "saturated" means lacking carbon-carbon double bonds, carbon-carbon triple bonds, and (in heteroatom-containing groups) carbon-nitrogen, carbon-phosphorous, and carbon-silicon double bonds. Where a saturated chemical group is substituted by at least one substituent $R^S$, at least one double and/or triple bond optionally may or may not be present in substituents $R^S$. The term "unsaturated" means containing at least one carbon-carbon double bond, carbon-carbon triple bond, or (in heteroatom-containing groups) carbon-nitrogen, carbon-phosphorous, or carbon-silicon double bond, not including any such double bonds that may be present in substituents $R^S$, if any, or formally in (hetero) aromatic rings, if any.

Preferred embodiments of the invention contemplate employing the $(C_2-C_{40})$alkane or $(C_3-C_{40})$cycloalkane solvent as the first and second aprotic solvents. Embodiments of the invention also contemplate employing mixtures of two or more of the $(C_2-C_{40})$alkane solvents, two or more $(C_3-C_{40})$ cycloalkane solvents, or at least one $(C_2-C_{40})$alkane solvent and at least one $(C_3-C_{40})$cycloalkane solvent. As used herein, the term "$(C_2-C_{40})$alkane" means a straight or branched chain, non-aromatic hydrocarbon of from 2 to 40 carbon atoms. The $(C_2-C_{40})$alkane is unsubstituted or substituted with from 1 to 6 $(C_3-C_{20})$cycloalkyl groups. Examples of unsubstituted $(C_2-C_{40})$alkane are ethane, propane, normal-butane, normal-pentane, normal-hexane, normal-heptane, normal-octane, 2,2-dimethylhexane, normal-nonane, normal-decane, normal-undecane, normal-dodecane, normal-$(C_{13}-C_{40})$alkane, and isoparaffinic fluids. Preferably, the $(C_2-C_{40})$alkane contains at least 5 carbon atoms. An example of a substituted $(C_2-C_{40})$alkane is tricyclohexylmethane. The term "$(C_3-C_{40})$cycloalkane" means a monocyclic, bicyclic $(C_5-C_{40})$, or tricyclic $(C_7-C_{40})$ non-aromatic hydrocarbon of from 3 to 40, 5 to 40, or 7 to 40 carbon atoms, respectively. The $(C_3-C_{40})$cycloalkane is unsubstituted or substituted with from 1 to 6 $(C_1-C_{20})$alkyl groups. Preferably the $(C_3-C_{40})$ cycloalkane is monocyclic. Examples of unsubstituted monocyclic $(C_3-C_{40})$cycloalkane are cyclopropane, cyclobutane, cyclopentane, cyclohexane, cycloheptane, cyclooctane, cyclononane, cyclodecane, cycloundecane, cyclododecane, and monocyclo$(C_{13}-C_{40})$alkane. An example of a substituted monocyclic $(C_3-C_{40})$cycloalkane is methylcyclohexane. Examples of unsubstituted bicyclic $(C_5-C_{40})$, cycloalkane are decahydronaphthylene and norbornane. An example of unsubstituted tricyclic $(C_7-C_{40})$, cycloalkane is tetradecahydroanthracene.

In some embodiments the aprotic solvent or mixture of aprotic solvents employed by the invention consist essentially of, and in some embodiments consist of, the $(C_2-C_{40})$alkane solvent(s) or $(C_3-C_{40})$cycloalkane. In some embodiments the $(C_2-C_{40})$alkane solvent(s) comprise an isoparaffinic fluid (e.g., ISOPAR E, ISOPAR F, ISOPAR G, ISOPAR H, ISOPAR L, ISOPAR M, or ISOPAR V, ExxonMobil Corporation, Irving, Tex., USA). In some embodiments the $(C_3-C_{40})$cycloalkane solvent comprises a alkyl-substituted cycloalkane. In some embodiments the $(C_2-C_{40})$alkane solvent(s) or $(C_3-C_{40})$cycloalkane solvent(s) has (have) a boiling point or distillation range according to ASTM-D86 at 101 kilopascals that is greater than the reaction temperature. Preferably, the polymerizable olefins are copolymerized at a reaction temperature of from 130° C. to 250° C. and the $(C_2-C_{40})$alkane solvent comprises the isoparaffinic fluid.

In some embodiments, the metal-ligand complex of formula (I), invention catalyst, or preferably both, is characterizable as having a solubility in the $(C_2-C_{40})$alkane or $(C_3-C_{40})$ cycloalkane solvent, preferably 1-octane, at 24° C. of 0.5 weight percent (wt %) or greater, preferably 1.0 wt % or greater, and still more preferably 2.0 wt % or greater.

In the metal-ligand complex of formula (I) and ligand of formula (Q) certain variables and chemical groups n, M, X, L, Z, $R^{3a}$, $R^{4a}$, $R^{3b}$, $R^{4b}$, $R^{5c}$, $R^{5f}$, $R^{5cc}$, $R^{5ff}$, $R^{6c}$, $R^{7c}$, $R^{8c}$, $R^{6d}$, $R^{7d}$, and $R^{8d}$, as the formulas allow, are preferred. Examples of such preferred groups follow.

In some embodiments M is a metal of Group 3. Group 3 metals (symbol), including lanthanoids and actinoids, useful in the present invention are scandium (Sc), yttrium (Y), the lanthanides (sometimes called lanthanoids), especially lanthanum (La), cerium (Ce), praseodymium (Pr), neodymium (Nd), promethium (Pm), samarium (Sm), europium (Eu), gadolinium (Gd), terbium (Tb), dysprosium (Dy), holium (Ho), erbium (Er), thulium (Tm), ytterbium (Yb), and lutetium (Lu), and the stable actinides (sometimes called actinoids), especially stable isotopes of actinium (Ac), thorium (Th), and uranium (U). Unstable actinides such as protactinium (Pa), neptunium (Np), plutonium (Pu), americium (Am), curium (Cm), berkelium (Bk), californium (Cf), einsteinium (Es) fermium (Fm), mendelevium (Md), nobelium (No), and lawrencium (Lr) are excluded from the actinides useful in the present invention. Preferred Group 3 metals are Sc and Y.

In some embodiments M is a metal of Group 4, more preferably titanium, zirconium, or hafnium, still more preferably zirconium or hafnium, and even more preferably M is hafnium. In some embodiments M is zirconium. In some embodiments M is titanium. Preferred Group 4 metals are those in a formal oxidation state of +3 or +4, more preferably +4. For purposes of the present invention, rutherfordium (Rf) is excluded from the Group 4 metals useful in the present invention.

In some embodiments M is a metal of Group 5. Group 5 metals useful in the present invention are vanadium (V), niobium (Nb), and tantalum (Ta). For purposes of the present invention, dubnium (Db) is excluded from the Group 5 metals useful in the present invention.

In some embodiments M is a metal of Group 6. Group 6 metals useful in the present invention are chromium (Cr), molybdenum (Mo), and tungsten (W). For purposes of the present invention, seaborgium (Sg) is excluded from the Group 6 metals useful in the present invention.

In some embodiments M is in a formal oxidation state of +2. In some embodiments M is in a formal oxidation state of +3. In some embodiments M is in a formal oxidation state of +4. In some embodiments M is in a formal oxidation state of +5. In some embodiments M is in a formal oxidation state of +6. The invention contemplates any combination of a preferred M and a preferred formal oxidation state. A preferred formal oxidation state of the metal of Group 3 is +3. A preferred formal oxidation state of the metal of Group 4 is +2 or +4. A preferred formal oxidation state of the metal of Group 5 is +3 or +5.

Generally the X groups are not critical. Certain X is/are preferred. In some embodiments each X independently is the monodentate ligand. When there are two or more X monodentate ligands, preferably each such X is the same. In some embodiments the monodentate ligand is the monoanionic ligand. The monoanionic ligand has a net formal oxidation state of −1. Each monoanionic ligand preferably independently is hydride, $(C_1-C_{40})$hydrocarbyl carbanion, $(C_1-C_{40})$heterohydrocarbyl carbanion, halide, nitrate, carbonate, phosphate, sulfate, $HC(O)O^-$, $(C_1-C_{40})$hydrocarbyl$C(O)O^-$, $HC(O)N(H)^-$, $(C_1-C_{40})$hydrocarbyl$C(O)N(H)^-$, $(C_1-C_{40})$hydrocarbyl$C(O)N((C_1-C_{20})$hydrocarbyl$)^-$, $R^K R^L B^-$, $R^K R^L N^-$, $R^K O^-$, $R^K S^-$, $R^K R^L P^-$, or $R^M R^K R^L Si^-$, wherein each $R^K$, $R^L$, and $R^M$ independently is hydrogen, $(C_1-C_{40})$hydrocarbyl, or $(C_1-C_{40})$heterohydrocarbyl, or $R^K$ and $R^L$ are taken together to form a $(C_2-C_{40})$hydrocarbylene or $(C_1-C_{40})$heterohydrocarbylene and $R^M$ is as defined above. Preferably, each the monoanionic ligand is $(C_1-C_{40})$hydrocarbyl carbanion or halide.

In some embodiments at least one monodentate ligand of X independently is the neutral ligand. Preferably the neutral ligand is a neutral Lewis base group that is $R^X NR^K R^L$, $R^K OR^L$, $R^K SR^L$, or $R^X PR^K R^L$, wherein each $R^X$ independently is hydrogen, $(C_1-C_{40})$hydrocarbyl, $[(C_1-C_{10})$hydrocarbyl$]_3 Si$, $[(C_1-C_{10})$hydrocarbyl$]_3 Si(C_1-C_{10})$hydrocarbyl, or $(C_1-C_{40})$heterohydrocarbyl and each $R^K$ and $R^L$ independently is as defined above.

When n is 2 or greater, some embodiments contemplate a combination of monodentate X comprising a monoanionic ligand and neutral ligand. In some embodiments, each X is a monodentate ligand that independently is a halogen atom (halide), unsubstituted $(C_1-C_{20})$hydrocarbyl (carbanion), unsubstituted $(C_1-C_{20})$hydrocarbyl$C(O)O$—, or $R^K R^L N$— wherein each of $R^K$ and $R^L$ independently is an unsubstituted $(C_1-C_{20})$hydrocarbyl. In some embodiments each monodentate ligand X is a chlorine atom (chloride), $(C_1-C_{10})$hydrocarbyl (carbanion) (e.g., $(C_1-C_6)$alkyl or benzyl carbanion), unsubstituted $(C_1-C_{10})$hydrocarbyl$C(O)O$—, or $R^K R^L N$— wherein each of $R^K$ and $R^L$ independently is an unsubstituted $(C_1-C_{10})$hydrocarbyl.

In some embodiments there are at least two X and the two X are taken together to form the bidentate ligand. In some embodiments the bidentate ligand is a neutral bidentate ligand. Preferably the neutral bidentate ligand is a diene of formula $(R^D)_2 C=C(R^D)-C(R^D)=C(R^D)_2$, wherein each $R^D$ independently is H, unsubstituted $(C_1-C_6)$alkyl, phenyl, or naphthyl. In some embodiments the bidentate ligand is a monoanionic-mono(Lewis base) ligand. The monoanionic-mono(Lewis base) ligand preferably is a 1,3-dionate of formula (D): $R^E-C(O^-)=CH-C(=O)-R^E$ (D), wherein each RD independently is H, unsubstituted $(C_1-C_6)$alkyl, phenyl, or naphthyl. In some embodiments the bidentate ligand is a dianionic ligand. The dianionic ligand has a net formal oxidation state of −2. Preferably each dianionic ligand independently is carbonate, oxalate (i.e., $^-O_2 CC(O)O^-$), $(C_2-C_{40})$hydrocarbylene dicarbanion, $(C_1-C_{40})$heterohydrocarbylene dianion (e.g., $(C_1-C_{40})$heterohydrocarbylene dicarbanion or monocarbanion, nitrogen monoanion), phosphate, or sulfate.

As used herein, the term "carbonate" means an ionic substance consisting of zero or one cations $Q^X$ and an anion of the empirical formula $CO_3^{-2}$, the ionic substance having an overall −1 or −2 charge. The term "nitrate" means an ionic substance consisting of an anion of the empirical formula $NO_3^-$, the ionic substance having an overall −1 charge. The term "oxalate" means an ionic substance consisting of zero or one cations $Q^X$ and an anion of the empirical formula $^-OC(O)C(O)O^-$, the ionic substance having an overall −1 or −2 charge. The term "phosphate" means an ionic substance consisting of zero, one, or two cations $Q^X$ and an anion of the empirical formula $PO_4^{-3}$ the ionic substance having an overall −1, −2, or −3 charge. The term "sulfate" means an ionic substance consisting of zero or one cations $Q^X$ and an anion of the empirical formula $SO_4^{-2}$, the ionic substance having an overall −1 or −2 charge. In each of the ionic substances, preferably $Q^X$ independently is an inorganic cation of hydrogen atom, lithium, sodium, potassium, calcium, or magnesium, including hemi calcium and hemi magnesium.

As previously mentioned, number and charge (neutral, monoanionic, dianionic) of X are selected depending on the formal oxidation state of M such that the metal-ligand complex of formula (I) is, overall, neutral. The integer n indicates number of X. In some embodiments n is 0 and there are 0 X. In some embodiments n is 1 and there is 1 X. In some embodiments n is 2 and there is 2 X. In some embodiments n is 3 and there is 3 X. In some embodiments n is 4 and there is 4 X. In some embodiments n is 5 and there is 5 X. Preferably n is 2 or 3 and at least two X independently are monoanionic monodentate ligands and a third X, if present, is a neutral monodentate ligand. In some embodiments n is 2 and each of the two X independently is a monoanionic monodentate ligand, more preferably the same monoanionic monodentate ligand, and still more preferably M is hafnium in a +4 oxidation state, n is 2, and each of the two X is a same monoanionic monodentate ligand. In some embodiments n is 2 and two X are taken together to form a bidentate ligand. In some embodiments the bidentate ligand is 2,2-dimethyl-2-silapropane-1,3-diyl or 1,3-butadiene.

In some embodiments each X is the same, wherein each X is methyl; ethyl; 1-propyl; 2-propyl; 1-butyl; 2,2,-dimethylpropyl; trimethylsilylmethyl; phenyl; benzyl; or chloro. In some embodiments n is 2 and each X is the same.

In some embodiments at least two X are different. In some embodiments each of at least two X are a different one of methyl; ethyl; 1-propyl; 2-propyl; 1-butyl; 2,2,-dimethylpropyl; trimethylsilylmethyl; phenyl; benzyl; and chloro. In some embodiments at least one X is methyl; ethyl; 1-propyl; 2-propyl; 1-butyl; 2,2,-dimethylpropyl; trimethylsilylmethyl; phenyl; benzyl; or chloro; and another X is the neutral monodentate ligand.

More preferably X and n independently are as defined as in any one of the Examples described later in the EXAMPLES OF THE PRESENT INVENTION section.

Certain Z groups in formula (I) are preferred. In some embodiments each Z is different. In some embodiments one Z is O and one Z is N($C_1$-$C_{40}$)hydrocarbyl (e.g., NCH$_3$). In some embodiments one Z is O and one Z is S. In some embodiments one Z is S and one Z is N($C_1$-$C_{40}$)hydrocarbyl (e.g., NCH$_3$). In some embodiments each Z is the same. In some embodiments each Z is O. In some embodiments each Z is S. In some embodiments each Z is N($C_1$-$C_{40}$)hydrocarbyl (e.g., NCH$_3$). In some embodiments at least one, and in some embodiments each Z is P($C_1$-$C_{40}$)hydrocarbyl (e.g., PCH$_3$).

A certain L group in formula (I) is preferred. In some embodiments L is the ($C_1$-$C_{40}$)hydrocarbylene, and more preferably the ($C_1$-$C_{40}$)hydrocarbylene comprising a portion comprising a 7-carbon atom to 12-carbon atom linker backbone linking the Z atoms in formula (I), and still more preferably the ($C_1$-$C_{40}$)hydrocarbylene comprising a portion comprising a 1-carbon atom to 6-carbon atom linker backbone linking the Z atoms in formula (I). Preferably the portion that comprises the 1-carbon atom to 6-carbon atom linker backbone of the ($C_1$-$C_{40}$)hydrocarbylene of L comprises a 2-carbon atom to 5-carbon atom, and more preferably a 3-carbon atom or 4-carbon atom linker backbone linking the Z atoms in formula (I) to which L is bonded. In some embodiments L comprises the 1-carbon atom linker backbone (e.g., L is —CH$_2$— or C(=O)). In some embodiments L comprises the 2-carbon atom linker backbone (e.g., L is —CH$_2$CH$_2$— or —CH(CH$_3$)CH(CH$_3$)—). In some embodiments L comprises the 3-carbon atom linker backbone (e.g., L is —CH$_2$CH$_2$CH$_2$—; —CH(CH$_3$)CH$_2$CH(CH$_3$)—; —CH(CH$_3$)CH(CH$_3$)CH(CH$_3$)—; —CH$_2$C(CH$_3$)$_2$CH$_2$—); 1,3-cyclopentane-diyl; or 1,3-cyclohexane-diyl. In some embodiments L comprises the 4-carbon atom linker backbone (e.g., L is —CH$_2$CH$_2$CH$_2$CH$_2$—; —CH$_2$C(CH$_3$)$_2$C(CH$_3$)$_2$CH$_2$—; 1,2-bis(methylene)cyclohexane; or 2,3-bis(methylene)-bicyclo[2.2.2]octane). In some embodiments L comprises the 5-carbon atom linker backbone (e.g., L is —CH$_2$CH$_2$CH$_2$CH$_2$CH$_2$— or 1,3-bis(methylene)cyclohexane). In some embodiments L comprises the 6-carbon atom linker backbone (e.g., L is —CH$_2$CH$_2$CH$_2$CH$_2$CH$_2$CH$_2$— or 1,2-bis(ethylene)cyclohexane).

Preferably L is the ($C_1$-$C_{40}$)hydrocarbylene and the ($C_1$-$C_{40}$)hydrocarbylene of L is a ($C_2$-$C_{12}$)hydrocarbylene, and more preferably ($C_3$-$C_8$)hydrocarbylene. In some embodiments the ($C_1$-$C_{40}$)hydrocarbylene is an unsubstituted ($C_1$-$C_{40}$)alkylene. In some embodiments the ($C_1$-$C_{40}$)hydrocarbylene is a substituted ($C_1$-$C_{40}$)alkylene. In some embodiments the ($C_1$-$C_{40}$)hydrocarbylene is an unsubstituted ($C_3$-$C_{40}$)cycloalkylene or substituted ($C_3$-$C_{40}$)cycloalkylene, wherein each substituent independently is $R^S$, wherein preferably the $R^S$ independently is ($C_1$-$C_4$)alkyl.

In some embodiments L is the unsubstituted ($C_1$-$C_{40}$)alkylene, and more preferably L is an acyclic unsubstituted ($C_1$-$C_{40}$)alkylene, and still more preferably the acyclic unsubstituted ($C_1$-$C_{40}$)alkylene is —CH$_2$CH$_2$—, —CH$_2$CH$_2$CH$_2$—, cis —CH(CH$_3$)CH$_2$CH(CH$_3$)—, trans —CH(CH$_3$)CH$_2$CH(CH$_3$)—, —CH(CH$_3$)CH$_2$CH(CH$_3$)$_2$—, —CH(CH$_3$)CH(CH$_3$)CH(CH$_3$)—, —CH$_2$C(CH$_3$)$_2$CH$_2$—, —CH$_2$CH$_2$CH$_2$CH$_2$—, or —CH$_2$C(CH$_3$)$_2$C(CH$_3$)$_2$CH$_2$—. In some embodiments L is the substituted ($C_1$-$C_{40}$)alkylene, and more preferably L is a ($C_1$-$C_{40}$)alkylene-substituted ($C_1$-$C_{40}$)alkylene, and still more preferably the ($C_1$-$C_{40}$)alkylene-substituted ($C_1$-$C_{40}$)alkylene is trans-1,2-bis(methylene)cyclopentane, cis-1,2-bis(methylene)cyclopentane, trans-1,2-bis(methylene)cyclohexane, or cis-1,2-bis(methylene)cyclohexane. In some embodiments the ($C_1$-$C_{40}$)alkylene-substituted ($C_1$-$C_{40}$)alkylene is exo-2,3-bis(methylene)bicyclo[2.2.2]octane or exo-2,3-bis(methylene)-7,7-dimethyl-bicyclo[2.2.1]heptane. In some embodiments L is the unsubstituted ($C_3$-$C_{40}$)cycloalkylene, and more preferably L is cis-1,3-cyclopentane-diyl or cis-1,3-cyclohexane-diyl. In some embodiments L is the substituted ($C_3$-$C_{40}$)cycloalkylene, and more preferably L is a ($C_1$-$C_{40}$)alkylene-substituted ($C_3$-$C_{40}$)cycloalkylene, and still more preferably L is the ($C_1$-$C_{40}$)alkylene-substituted ($C_3$-$C_{40}$)cycloalkylene that is exo-bicyclo[2.2.2]octan-2,3-diyl. In some embodiments L is —CH$_2$CH$_2$—, in other embodiments —CH$_2$CH$_2$CH$_2$—, in other embodiments cis —CH(CH$_3$)CH$_2$CH(CH$_3$)—, in other embodiments trans —CH(CH$_3$)CH$_2$CH(CH$_3$)—, in other embodiments —CH(CH$_3$)CH$_2$CH(CH$_3$)$_2$—, in other embodiments —CH(CH$_3$)CH(CH$_3$)CH(CH$_3$)—, in other embodiments —CH$_2$C(CH$_3$)$_2$CH$_2$—, in other embodiments —CH$_2$CH$_2$CH$_2$CH$_2$—, in other embodiments —CH$_2$C(CH$_3$)$_2$C(CH$_3$)$_2$CH$_2$—, in other embodiments trans-1,2-bis(methylene)cyclopentane, in other embodiments cis-1,2-bis(methylene)cyclopentane, in other embodiments trans-1,2-bis(methylene)cyclohexane, in other embodiments cis-1,2-bis(methylene)cyclohexane, in other embodiments cis-1,3-cyclopentane-diyl, in other embodiments cis-1,3-cyclohexane-diyl, in other embodiments exo-2,3-bis(methylene)bicyclo[2.2.2]octane, and in other embodiments exo-2,3-bis(methylene)-7,7-dimethyl-bicyclo[2.2.1]heptane.

In some embodiments L is the ($C_1$-$C_{40}$)heterohydrocarbylene, and more preferably the ($C_1$-$C_{40}$)heterohydrocarbylene comprising a portion comprising a 7-atom to 12-atom linker backbone linking the Z atoms in formula (I), and still more preferably the ($C_1$-$C_{40}$)heterohydrocarbylene comprising a portion comprising a 1-atom to 6-atom linker backbone linking the Z atoms in formula (I). Preferably the portion that comprises the 1-atom to 6-atom linker backbone of the ($C_1$-$C_{40}$)heterohydrocarbylene of L comprises a from 2-atom to 5-atom, and more preferably a 3-atom or 4-atom linker backbone linking the Z atoms in formula (I) to which L is bonded. In some embodiments L comprises the 1-atom linker backbone (e.g., L is —CH(OCH$_3$)— or —Si(CH$_3$)$_2$—). In some embodiments L comprises the 2-atom linker backbone (e.g., L is —CH$_2$CH(OCH$_3$)— or —CH$_2$Si(CH$_3$)$_2$—). In some embodiments L comprises the 3-atom linker backbone (e.g., L is —CH$_2$CH$_2$CH(OCH$_3$)—, —CH$_2$Si(CH$_3$)$_2$CH$_2$—, or —CH$_2$Ge(CH$_3$)$_2$CH$_2$—). The "—CH$_2$Si(CH$_3$)$_2$CH$_2$-" may be referred to herein as a 1,3-diradical of 2,2-dimethyl-2-silapropane. In some embodiments L comprises the 4-atom linker backbone (e.g., L is —CH$_2$CH$_2$OCH$_2$— or —CH$_2$P(CH$_3$)CH$_2$CH$_2$—). In some embodiments L comprises the 5-atom linker backbone (e.g., L is —CH$_2$CH$_2$OCH$_2$CH$_2$— or —CH$_2$CH$_2$N(CH$_3$)CH$_2$CH$_2$—). In some embodiments L comprises the 6-atom linker backbone (e.g., L is —CH$_2$CH$_2$C(OCH$_3$)$_2$CH$_2$CH$_2$CH$_2$—, —CH$_2$CH$_2$CH$_2$S(O)$_2$CH$_2$CH$_2$—, or —CH$_2$CH$_2$S(O)CH$_2$CH$_2$CH$_2$—). In some embodiments each of the from 1 to 6 atoms of the 1-atom to 6-atom linker backbone is a carbon atom (the heteroatom(s) of the ($C_1$-$C_{40}$)heterohydrocarbylene thereby being elsewhere therein). In some embodiments one of the from 1 to 6 atoms of the 1-atom to 6-atom linker backbone is a heteroatom and the rest of the from 1 to 6 atoms, if any, are carbon atoms. In some embodiments two of the from 2 to 6 atoms of the 2-atom to 6-atom linker backbone independently are heteroatoms and the rest of the from 2 to 6 atoms, if any, are carbon atoms. In some embodiments at least one heteroatom is the Si($R^C$)$_2$. In some embodiments at least one heteroatom is the O. In some embodiments at least one heteroatom is the S(O). In some embodiments at least one heteroatom is the S(O)$_2$. In some embodiments at least one heteroatom is the P($R^P$). In some embodiments at least one heteroatom is the N($R^N$). Preferably, there are no O—O, S—S, or O—S bonds, other than O—S bonds in the S(O) or S(O)$_2$ diradical functional group, in —Z-L-Z—. More preferably, there are no O—O, N—N, P—P, N—P, S—S, or O—S bonds, other than O—S bonds in an S(O) or S(O)$_2$ diradical functional group, in —Z-L-Z—. Preferably the (C$_1$-C$_{40}$)heterohydrocarbylene is (C$_1$-C$_{11}$)heterohydrocarbylene, and more preferably (C$_1$-C$_7$)heterohydrocarbylene. In some embodiments L is the (C$_1$-C$_7$)heterohydrocarbylene, and the (C$_1$-C$_7$)heterohydrocarbylene of L is —CH$_2$Si(CH$_3$)$_2$CH$_2$—; —CH$_2$CH$_2$Si(CH$_3$)$_2$CH$_2$—; or CH$_2$Si(CH$_3$)$_2$CH$_2$CH$_2$—. In some embodiments the (C$_1$-C$_7$) heterohydrocarbylene of L is —CH$_2$Si(CH$_3$)$_2$CH$_2$—, in other embodiments —CH$_2$Si(CH$_2$CH$_3$)$_2$CH$_2$—, in other embodiments —CH$_2$Si(isopropyl)$_2$CH$_2$—, in other embodiments —CH$_2$Si(tetramethylene)CH$_2$—, and in other embodiments —CH$_2$Si(pentamethylene)CH$_2$—. The —CH$_2$Si(tetramethylene)CH$_2$— is named 1-silacyclopentan-1,1-dimethylene. The —CH$_2$Si(pentamethylene)CH$_2$— is named 1-silacyclohexan-1,1-dimethylene.

More preferably L is defined as in any one of the Examples described later in the EXAMPLES OF THE PRESENT INVENTION section.

Certain $R^{3a}$ and $R^{3b}$ groups are preferred. In some embodiments each of $R^{3a}$ and $R^{3b}$ independently is a (C$_1$-C$_{40}$)hydrocarbyl, (C$_1$-C$_{40}$)heterohydrocarbyl, or halogen atom. In some embodiments each of $R^{3a}$ and $R^{3b}$ independently is a (C$_1$-C$_{20}$)hydrocarbyl, (C$_1$-C$_{20}$)heterohydrocarbyl, or halogen atom. In some embodiments each of $R^{3a}$ and $R^{3b}$ independently is a (C$_1$-C$_{10}$)hydrocarbyl, (C$_1$-C$_{40}$)heterohydrocarbyl, or halogen atom. In some embodiments each of $R^{3a}$ and $R^{3b}$ independently is a (C$_1$-C$_{40}$)hydrocarbyl or halogen atom. In some embodiments at least one of $R^{3a}$ and $R^{3b}$ is (C$_1$-C$_{40}$)hydrocarbyl. In some embodiments at least one, preferably both of $R^{3a}$ and $R^{3b}$ is halogen atom, more preferably a fluorine atom or chlorine atom, and still more preferably a fluorine atom. In some embodiments each of $R^{3a}$ and $R^{3b}$ independently is a (C$_1$-C$_6$)hydrocarbyl, (C$_1$-C$_5$)heterohydrocarbyl, fluorine atom, or chlorine atom. In some embodiments each of $R^{3a}$ and $R^{3b}$ independently is (C$_1$-C$_6$)alkyl, (C$_3$-C$_6$)cycloalkyl, (C$_1$-C$_6$)heteroalkyl, fluorine atom, or chlorine atom. In some embodiments of the metal-ligand complex of formula (I) each of $R^{3a}$ and $R^{3b}$ independently is a methyl; ethyl; propyl (preferably 2-propyl); butyl (preferably 1,1,-dimethylethyl); trifluoromethyl; cyclopropyl; —NH$_2$; N,N-diethylamino; cyano; nitro, methoxy; fluorine atom, or chlorine atom. In some embodiments of the metal-ligand complex of formula (I) each of $R^{3a}$ and $R^{3b}$ independently is a methyl; ethyl; propyl (preferably 2-propyl); butyl (preferably 1,1,-dimethylethyl); fluorine atom, or chlorine atom. In some embodiments $R^{3a}$ and $R^{3b}$ are the same as each other. In other embodiments $R^{3a}$ and $R^{3b}$ are different from each other. In some embodiments of the metal-ligand complex of formula (I) each of $R^{3a}$ and $R^{3b}$ is methyl; ethyl; 2-propyl; 1,1-dimethylethyl; trifluoromethyl; halogen atom; cyano; nitro, methoxy; —NH$_2$; or dimethylamino. More preferably $R^{3a}$ and $R^{3b}$ independently are defined therefor are defined as in any one of the Examples described later in the EXAMPLES OF THE PRESENT INVENTION section.

Certain $R^{4a}$ and $R^{4b}$ groups are preferred. In some embodiments each of $R^{4a}$ and $R^{4b}$ is a hydrogen atom. In some embodiments at least one and in some embodiments each of $R^{4a}$ and $R^{4b}$ independently is as defined previously for $R^{3a}$. More preferably $R^{4a}$ ad $R^{4b}$ independently are defined therefor are defined as in any one of the Examples described later in the EXAMPLES OF THE PRESENT INVENTION section Certain $R^{5c}$ to $R^{5ff}$ groups are preferred. In some embodiments $R^{5c}$ and $R^{5f}$ are the same and, independently, $R^{5cc}$ and $R^{5ff}$ are the same. In some embodiments $R^{5c}$ and $R^{5f}$ are respectively the same as $R^{5cc}$ and $R^{5ff}$. In other embodiments at least one of $R^{5c}$ and $R^{5ff}$ is different than a respective one of $R^{5cc}$ and $R^{5ff}$. In some embodiments at least $R^{5c}$ and $R^{5cc}$ are not hydrogen atoms; more preferably each of $R^{5c}$, $R^{5cc}$, $R^{5f}$, and $R^{5ff}$ are not hydrogen atoms; still more preferably each of $R^{5c}$, $R^{5cc}$, $R^{5f}$, and $R^{5ff}$ are not hydrogen atoms and $R^{5c}$ and $R^{5cc}$ are the same as each other and $R^{5f}$ and $R^{5ff}$ are the same as each other; even more preferably each of $R^{5c}$, $R^{5cc}$, $R^{5f}$, and $R^{5ff}$ are not hydrogen atoms and $R^{5c}$, $R^{5cc}$, $R^{5f}$, and $R^{5ff}$ are the same as each other. More preferably, each of $R^{5c}$ to $R^{5ff}$ independently is a (C$_1$-C$_{40}$)hydrocarbyl. Preferably the (C$_1$-C$_{40}$)hydrocarbyl of $R^{5c}$ to $R^{5ff}$ independently is (C$_2$-C$_{20}$)hydrocarbyl; more preferably (C$_2$-C$_{10}$)alkyl, phenyl, or alkyl-substituted phenyl; still more preferably (C$_2$-C$_8$)alkyl or phenyl; and even more (C$_4$-C$_8$)alkyl. In some embodiments each of $R^{5c}$ to $R^{5ff}$ independently is bromo; cyano; methyl; ethyl; or propyl (preferably isopropyl). In some embodiments each of $R^{5c}$ to $R^{5ff}$ independently is butyl (preferably 1-butyl or, more preferably tertiary-butyl); pentyl (preferably 1,1-dimethylpropan-1-yl); hexyl (preferably 1,1-dimethylbutan-1-yl); heptyl (preferably 1,1-dimethylpentan-1-yl); octyl (preferably 1,1-dimethylhexan-1-yl or 2,4,4-trimethylpentan-2yl, or more preferably 2,4,4-trimethylpentan-2yl (i.e., tertiary-octyl, (CH$_3$)$_3$CCH$_2$C(CH$_3$)$_2$—). In some embodiments $R^{5c}$ to $R^{5ff}$ are defined therefor as in any one of the Examples described later in the EXAMPLES OF THE PRESENT INVENTION section.

Certain $R^{6c}$, $R^{8c}$, $R^{6d}$, and $R^{8d}$ groups are preferred. In some embodiments each of $R^{6c}$, $R^{8c}$, $R^{6d}$, and $R^{8d}$ is a hydrogen atom. In some embodiments each of $R^{6c}$, $R^{8c}$, $R^{6d}$, and $R^{8d}$ independently is a hydrogen atom; (C$_1$-C$_{40}$)hydrocarbyl; (C$_1$-C$_{40}$)heterohydrocarbyl; or halogen atom. In some embodiments one of $R^{6c}$, $R^{8c}$, $R^{6d}$, and $R^{8d}$ independently is (C$_1$-C$_{40}$)hydrocarbyl; (C$_1$-C$_{40}$)heterohydrocarbyl; or halogen atom, and each of the remainder of $R^{6c}$, $R^{8c}$, $R^{6d}$, and $R^{8d}$ is a hydrogen atom. In some embodiments at least one of $R^{6c}$, $R^{8c}$, $R^{6d}$, and $R^{8d}$ is a (C$_4$-C$_{40}$)hydrocarbyl and the remainder, if any, of $R^{6c}$, $R^{8c}$, $R^{6d}$, and $R^{8d}$ is a (C$_4$-C$_{40}$)hydrocarbyl or hydrogen atom. In some embodiments two or more of $R^{6c}$, $R^{8c}$, $R^{6d}$, and $R^{8d}$ independently is (C$_1$-C$_{40}$)hydrocarbyl; (C$_1$-C$_{40}$)heterohydrocarbyl; or halogen atom, and each of the remainder, if any, of $R^{6c}$, $R^{8c}$, $R^{6d}$, and $R^{8d}$ is a hydrogen atom. In some embodiments at least one of $R^{6c}$ and $R^{8c}$ or at least one of $R^{6d}$ and $R^{8d}$, and in some embodiments at least one of $R^{6c}$ and $R^{8c}$ and at least one of $R^{6d}$ and $R^{8d}$, is fluoro; cyano; methyl; ethyl; propyl (preferably isopropyl); or butyl (preferably 1-butyl or, more preferably tertiary-butyl. More preferably $R^{6c}$, $R^{8c}$, $R^{6d}$, and $R^{8d}$ independently are defined therefor as in any one of the Examples described later in the EXAMPLES OF THE PRESENT INVENTION section.

In some embodiments each of $R^{4a}$, $R^{4b}$, $R^{6c}$, $R^{8c}$, $R^{6d}$, and $R^{8d}$ is a hydrogen atom.

Certain $R^{7c}$ and $R^{7d}$ groups are preferred. In some embodiments at least one, and preferably each, of $R^{7c}$ and $R^{7d}$ independently is (C$_1$-C$_{40}$)hydrocarbyl, more preferably (C$_2$-C$_{40}$)hydrocarbyl, still more preferably (C$_4$-C$_{40}$)hydrocarbyl, and even more preferably (C$_4$-C$_{10}$)hydrocarbyl, and yet more preferably (C$_4$-C$_8$)hydrocarbyl, which embodiments are especially preferred when the invention catalyst is employed in the high reaction temperature embodiments of the invention process. In some embodiments at least one, and in some such embodiments, each of $R^{7c}$ and $R^{7d}$ independently is (C$_1$-C$_{40}$)heterohydrocarbyl; or halogen atom, more preferably (C$_1$-C$_{40}$)heterohydrocarbyl, still more preferably (C$_4$-

$C_{40}$)heterohydrocarbyl, and even more preferably ($C_4$-$C_8$) heterohydrocarbyl. In some embodiments each of $R^{7c}$ and $R^{7d}$ independently is a halogen atom or ($C_2$-$C_{40}$)alkyl, more preferably a ($C_2$-$C_{12}$)alkyl, still more preferably a ($C_4$-$C_{10}$) alkyl, and even more preferably ($C_4$-$C_{10}$)alkyl. In some embodiments each of $R^{7c}$ and $R^{7d}$ independently is bromo; cyano; methyl; ethyl; or propyl (preferably isopropyl). In some embodiments each of $R^{7c}$ and $R^{7d}$ independently is butyl (preferably 1-butyl or, more preferably tertiary-butyl); pentyl (preferably 1,1-dimethylpropan-1-yl); hexyl (preferably 1,1-dimethylbutan-1-yl); heptyl (preferably 1,1-dimethylpentan-1-yl); octyl (preferably 1,1-dimethylhexan-1-yl or 2,4,4-trimethylpentan-2yl, or more preferably 2,4,4-trimethylpentan-2yl (i.e., tertiary-octyl, $(CH_3)_3CCH_2C(CH_3)_2$—). In some embodiments each of $R^{7c}$ and $R^{7d}$ independently is methyl, tertiary-butyl, or 2,4,4-trimethylpentan-2yl (i.e., $(CH_3)_3CCH_2C(CH_3)_2$—). In some embodiments $R^{7c}$ and $R^{7d}$ are the same as each other. Preferably each of $R^{7c}$ and $R^{7d}$ is 2,4,4-trimethylpentan-2yl. In some embodiments $R^{7c}$ and $R^{7d}$ are different from each other. More preferably $R^{7c}$ and $R^{7d}$ independently are defined therefor as in any one of the Examples described later in the EXAMPLES OF THE PRESENT INVENTION section.

In some embodiments, at least one, and in other embodiments each of $R^{7c}$ and $R^{7d}$ is a hydrogen atom, and at least one of $R^{6c}$ and $R^{8c}$ is as defined previously for $R^{7c}$ and at least one of $R^{6d}$ and $R^{8d}$ is as defined previously for $R^{7d}$. Preferably, two of $R^{6c}$ to $R^{8c}$ are hydrogen atoms and two of $R^{6d}$ to $R^{8d}$ are hydrogen atoms, and the remainder of $R^{6c}$ to $R^{8c}$ and $R^{6d}$ to $R^{8d}$ are as defined previously for $R^{7c}$ and $R^{7d}$, respectively.

In some embodiments each hydrocarbyl independently is a ($C_1$-$C_{12}$)alkyl and each halogen atom independently is a fluorine atom or chlorine atom.

Certain combinations of n, M, X, L, Z, $R^{3a}$, $R^{4a}$, $R^{3b}$, $R^{4b}$, $R^{5c}$, $R^{5f}$, $R^{5cc}$, $R^{5ff}$, $R^{6c}$, $R^{7c}$, $R^{8c}$, $R^{6d}$, $R^{7d}$, and $R^{8d}$, as the formulas allow, are preferred. In some embodiments the metal-ligand complex of formula (I) each Z is O. More preferred in such embodiments is a metal-ligand complex of formula (Ia):

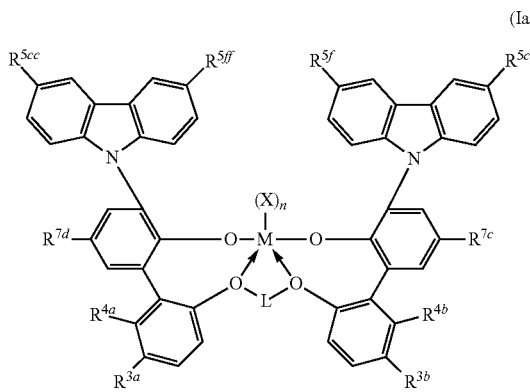

(Ia)

wherein M, X, L, $R^{3a}$, $R^{4a}$, $R^{3b}$, and $R^{4b}$ are as defined previously; $R^{7c}$ and $R^{7d}$ are independently ($C_4$-$C_{40}$)hydrocarbyl; and each of $R^{5c}$, $R^{5f}$, $R^{5cc}$, and $R^{5ff}$ is not hydrogen atom but is otherwise as defined previously. Preferably each $R^{5c}$, $R^{5f}$, $R^{5cc}$, and $R^{5ff}$ independently is an unsubstituted ($C_1$-$C_{12}$) alkyl, phenyl, or unsubstituted ($C_1$-$C_{12}$)alkyl-substituted phenyl.

In some embodiments the metal-ligand complex of formula (I) each Z is O and $R^{4a}$ and $R^{4b}$ are hydrogen atoms. More preferred in such embodiments is a metal-ligand complex of formula (Ia-1):

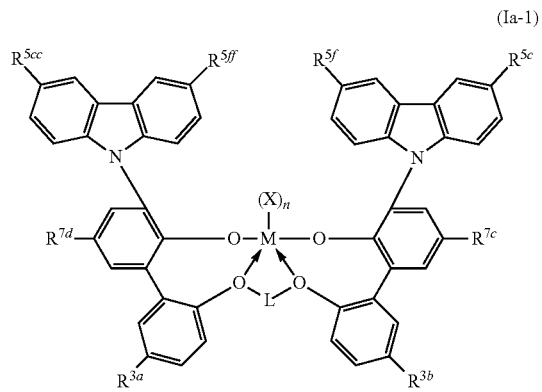

(Ia-1)

wherein M, X, L, $R^{3a}$, and $R^{3b}$ are as defined previously; $R^{7c}$ and $R^{7d}$ are independently ($C_4$-$C_{40}$)hydrocarbyl; and each of $R^{5c}$, $R^{5f}$, $R^{5cc}$, and $R^{5ff}$ is not hydrogen atom but is otherwise as defined previously. Preferably each $R^{5c}$, $R^{5f}$, $R^{5cc}$, and $R^{5ff}$ independently is an unsubstituted ($C_1$-$C_{12}$) alkyl, phenyl, or unsubstituted ($C_1$-$C_{12}$)alkyl-substituted phenyl.

Certain M, X, L, $R^{3a}$, $R^{4a}$, $R^{3b}$, $R^{4b}$, $R^{6c}$, $R^{7c}$, $R^{8c}$, $R^{6d}$, $R^{7d}$, and $R^{8d}$ (as the case may be) and combinations thereof are preferred in the metal-ligand complex of any one of formulas (Ia) to (Ia-1) as are preferred for the metal-ligand complex of formula (I). Examples of such preferred embodiments follow. In the metal-ligand complex of any one of formulas (Ia) to (Ia-1), preferably M is the metal of Group 4, more preferably hafnium or zirconium, and still more preferably hafnium. Preferably each X is a monodentate ligand. In some embodiments of the metal-ligand complex of any one of formulas (Ia) to (Ia-1), n is 2 or 3 and at least two X independently are monoanionic monodentate ligands and the third X, if present, is a neutral monodentate ligand. In some embodiments L is —$CH_2CH_2$—, —$CH_2CH_2CH_2$—, —$CH(CH_3)CH_2CH(CH_3)$—, —$CH_2C(CH_3)_2CH_2$—, —$CH_2CH_2CH_2CH_2$—, 1,2-bis(methylene)cyclohexane, or —$CH_2Si(CH_3)_2CH_2$—. In some embodiments each of $R^{3a}$ and $R^{3b}$ independently is methyl; ethyl; propyl (preferably 2-propyl); butyl (preferably 1,1-dimethylethyl); mono-, di-, or trifluoromethyl; methoxy; ethoxy; 1-methylethoxy; mono-, di-, or trifluoromethoxy; halogen atom; cyano; nitro; —$NH_2$; dimethylamino; aziridin-1-yl; or cyclopropyl. In some embodiments each of $R^{7c}$ and $R^{7d}$ independently is ($C_4$-$C_8$)alkyl. In some embodiments each ($C_1$-$C_{12}$)alkyl independently is methyl; ethyl; propyl (preferably 2-propyl); butyl (preferably 1,1-dimethylethyl); ($C_4$-$C_8$)alkyl; or a ($C_5$-$C_{12}$)alkyl; and each halogen atom independently is a fluorine atom or chlorine atom. In some embodiments the metal-ligand complex of formula (I) is the metal-ligand complex of any one of the formulas (Ia) to (Ia-1) except each Z that is O is replaced by a Z that is S. In some embodiments the metal-ligand complex of formula (I) is the metal-ligand complex of any one of the formulas (Ia) to (Ia-1) except each Z that is O is replaced by a Z that is N($C_1$-$C_{40}$) hydrocarbyl (e.g., $NCH_3$). In some embodiments the metal-ligand complex of formula (I) is the metal-ligand complex of any one of the formulas (Ia) to (Ia-1) except each Z that is O is replaced by a Z that is P($C_1$-$C_{40}$)hydrocarbyl (e.g., $PCH_3$).

Certain M, X, L, $R^{3a}$, $R^{4a}$, $R^{3b}$, $R^{4b}$, $R^{6c}$, $R^{7c}$, $R^{8c}$, $R^{6d}$, $R^{7d}$, $R^{8d}$ and $R^{9a}$, $R^{10a}$, $R^{11a}$, $R^{9b}$, $R^{10b}$, $R^{11b}$, $R^{9aa}$, $R^{10aa}$, $R^{11aa}$, $R^{9bb}$, $R^{10bb}$ and $R^{11bb}$ (as the case may be) and combinations thereof are preferred in the ligand of formula (Q) as are preferred for the metal-ligand complex of any one of formulas (I) to (Ia-1). In some embodiments the ligand of formula (Q) corresponds to a didehydro analog of the metal-ligand complex of formulas (Ia) to (Ia-1) (i.e., is a ligand of formula (Qa) to (Qa-1), respectively, wherein M and X and have been deleted and H has been added to each phenolate oxygen, wherein there are two phenolate oxygen atoms in formula (I), each phenolate oxygen being bonded to M via a bond depicted by a straight line "—"). In some embodiments the invention is the ligand of formula (Q). In some embodiments the invention is the Group 1 or 2 metal salt of the ligand of formula (Q). The Group 1 or 2 metal salt includes monometal salts, bimetal salts, and hemimetal salts. Examples of the monometal salt are Na(Q-H) and [CaOH](Q-H), wherein "Q-H" means a monodeprotonated ligand of formula (Q) having a formal charge of −1. Examples of the bimetal salts are $Na_2$(Q-2H) and $K_2$(Q-2H), wherein "Q-2H" means a doubly deprotonated (i.e., didehydro) ligand of formula (Q) having a formal charge of −2. Examples of the hemimetal salts are Ca(Q-H)$_2$ and Mg(Q-H)$_2$.

The Group 1 or 2 metal salt of the ligand of formula (Q) can be prepared or synthesized by conventional means. For example, the Group 1 or 2 metal salt of the ligand of formula (Q) can be prepared by contacting the ligand of formula (Q) with from one to two mole equivalents of a corresponding Group 1 or 2 metal base such as, for example, a Group 1 or 2 metal alkoxide, metal hydroxide, metal bicarbonate, or metal carbonate. Preferably the contacting is performed in a polar aprotic solvent (e.g., dimethylformamide, dimethylsulfoxide, acetone, or a mixture thereof), polar protic solvent (e.g., methanol, water, or a mixture thereof), or a mixture thereof. Alternatively the Group 1 or 2 metal salt can be directly prepared in situ without going through the conjugate acid that is the ligand of formula (Q). The Group 1 or 2 metal salt of the ligand of formula (Q) can be converted back to the ligand of formula (Q) (i.e., back to its conjugate acid form) by conventional means such as, for example, acidifying with an acid (e.g., acetic acid or hydrochloric acid) a solution or mixture of the Group 1 or 2 metal salt of the ligand of formula (Q) in a polar solvent. The ligand of formula (Q), or the Group 1 or 2 metal salt thereof, can be isolated readily by convention techniques (e.g., extraction, crystallization, precipitation, or chromatography).

Syntheses of some of the ligands (e.g., the ligand of formula (Q)) employed to prepare the metal-ligand complexes of formula (I) may utilize starting materials, intermediates, or reaction products that contain more than one reactive functional group. During chemical reactions, a reactive functional group may be protected from unwanted side reactions by a protecting group that renders the reactive functional group substantially inert to the reaction conditions employed. A protecting group is selectively introduced onto a starting material or intermediate prior to carrying out the reaction step for which the protecting group is needed. Once the protecting group is no longer needed, the protecting group can be removed. It is well within the ordinary skill in the art to introduce protecting groups during a synthesis and then later remove them. Procedures for introducing and removing protecting groups are known, for example, in Protective Groups in Organic Synthesis, 3rd ed., Greene T. W. and Wuts P. G., Wiley-Interscience, New York, 1999. The following moieties are examples of protecting groups that may be utilized to protect amino, hydroxy), or other functional groups: carboxylic acyl groups such as, for example, formyl, acetyl, and trifluoroacetyl; alkoxycarbonyl groups such as, for example, ethoxycarbonyl, tert-butoxycarbonyl (BOC), β,β,β-trichloroethoxycarbonyl (TCEC), and 3-iodoethoxycarbonyl; aralkyloxycarbonyl groups such as, for example, benzyloxycarbonyl (CBZ), para-methoxybenzyloxycarbonyl, and 9-fiuorenylmethyloxycarbonyl (FMOC); trialkylsilyl groups such as, for example, trimethylsilyl (TMS) and tert-butyldimethylsilyl (TBDMS); and other groups such as, for example, triphenylmethyl (trityl), tetrahydropyranyl, vinyloxycarbonyl, ortho-nitrophenylsulfenyl, diphenylphosphinyl, para-toluenesulfonyl (Ts), mesyl, trifluoromethanesulfonyl, methoxymethyl (MOM), and benzyl. Examples of procedures for removing protecting groups include hydrogenolysis of CBZ groups using, for example, hydrogen gas at about 3.4 atmospheres in the presence of a hydrogenation catalyst such as 10% palladium on carbon, acidolysis of BOC or MOM groups using, for example, hydrogen chloride in dichloromethane or trifluoroacetic acid (TFA) in dichloromethane, reaction of silyl groups with fluoride ions, and reductive cleavage of TCEC groups with zinc metal.

The invention contemplates preparing the metal-ligand complex of formula (I) and ligands of formula (Q) by any suitable method. The method of preparation is not critical. Preferably the method employs a convergent synthesis approach involving coupling together of two primary intermediates. Preferred illustrative procedures are described below and shown in FIGS. 1 to 4.

An illustrative procedure for preparing a first primary intermediate of formula useful in the convergent synthesis is shown in FIG. 1. In FIG. 1, the first primary intermediate is of formula (a5). The preparation of the first primary intermediate of formula (a5) starts with an electrophilic aromatic substitution reaction of phenol (a1) with a source of a leaving group LG, wherein LG is, for example, Br or I, to give functionalized phenol (a2). Depending on particular $R^4$ employed in FIG. 1, phenol (a1) is available from commercial suppliers or can be readily prepared by a person of ordinary skill in the art. The source of the leaving group LG-Y can be, for example, $Br_2$, N-bromosuccinimide (NBS), or $I_2$. If desired the $Br_2$ and $I_2$ can be prepared in situ such as by a procedure described later in certain Preparations. The oxygen of functionalized phenol (a2) can then be protected with a hydroxyl protecting group, PG, such as, for example, a methoxymethyl or tetrahydropyran-2-ylmethyl so as to form protected phenol (a3), which also has the leaving group LG. Protected phenol (a3) can be coupled with a source of $R^5$ (e.g., source of the $(C_1-C_{40})$hydrocarbyl or $(C_1-C_{40})$heterohydrocarbyl) such as, for example, $R^5$—H (a4) via an aryl coupling reaction so as to prepare first primary intermediate (a5). Such aryl coupling reactions are known for a variety of types of source of $R^5$ and include copper-mediated nitrogen arylation reactions where the H in $R^5$—H (a4) is bonded to a nitrogen atom of $R^5$, especially a nitrogen atom of a heteroaryl group; and palladium-mediated carbon arylation reactions where the H in $R^5$—H (a4) is bonded to an aromatic, alkenyl, or alkynyl carbon atom of $R^5$. The reactions described in FIG. 1 preferably are carried out under a substantially inert gas atmosphere in an anhydrous aprotic solvent such as, for example, diethyl ether, toluene, xylenes, tetrahydrofuran, diethylene glycol dimethyl ether, or a combination thereof and at a temperature in a range of from about −78° C. to about 200° C. Preferably, the reactions are carried out at atmospheric pressure.

Figure 2:
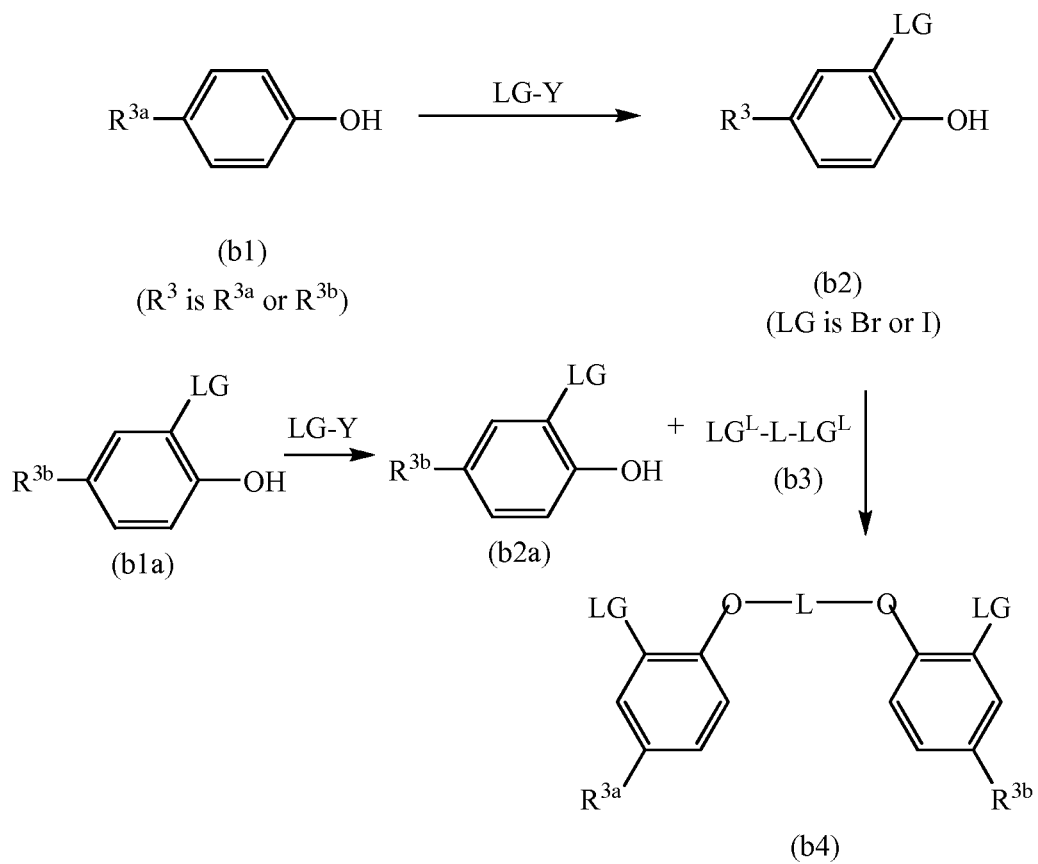
FIG. 2 shows an illustrative procedure for preparing a second primary intermediate useful in the convergent synthesis of the ligand of formula (Q).

An illustrative procedure for preparing a second primary intermediate useful in the convergent synthesis is shown in FIG. 2. In FIG. 2, the second primary intermediate is of formula (b4). The preparation of the second primary intermediate of formula (b4) starts with an electrophilic aromatic substitution reaction of phenol (b1) with a source of a leaving group LG, wherein LG is, for example, Br or I, to give functionalized phenol (b2). Separately, an electrophilic aromatic substitution reaction of phenol (b1a) with the source of the leaving group LG gives functionalized phenol (b2a). The source of the leaving group LG-Y can be the same as described previously for FIG. 1. Depending on particular $R^3$ employed in FIG. 2, phenol (b1) is available from commercial suppliers or can be readily prepared by a person of ordinary skill in the art. One mole equivalent (mole equiv.), more or less, of functionalized phenol (b2) and one mole equivalent, more or less, of functionalized phenol (b2a) together can then be reacted with a source of linker L, wherein the source is $LG^L$-L-$LG^L$ (b3), wherein L is as defined for formula (I), to give second primary intermediate (b4). $LG^L$ are leaving groups suitable for be displaced in a nucleophilic substitution reaction by a phenol or phenolate anion. Examples of suitable $LG^L$ are bromide, iodide, trifluoromethanesulfonate, tosylate, and trifluoroacetate. The reactions described in FIG. 2 preferably are carried out under a substantially inert gas atmosphere in an anhydrous aprotic solvent such as, for example, diethyl ether, toluene, xylenes, tetrahydrofuran, diethylene glycol dimethyl ether, or a combination thereof and at a temperature in a range of from about −78° C. to about 200° C. Preparation of second primary intermediate (b4) can also be carried out in polar organic solvents such as, for example, acetone, ethyl acetate, acetonitrile, ethanol, a mixture thereof, and water-containing mixtures thereof. Preferably, the reactions are carried out at atmospheric pressure.

Figure 3:
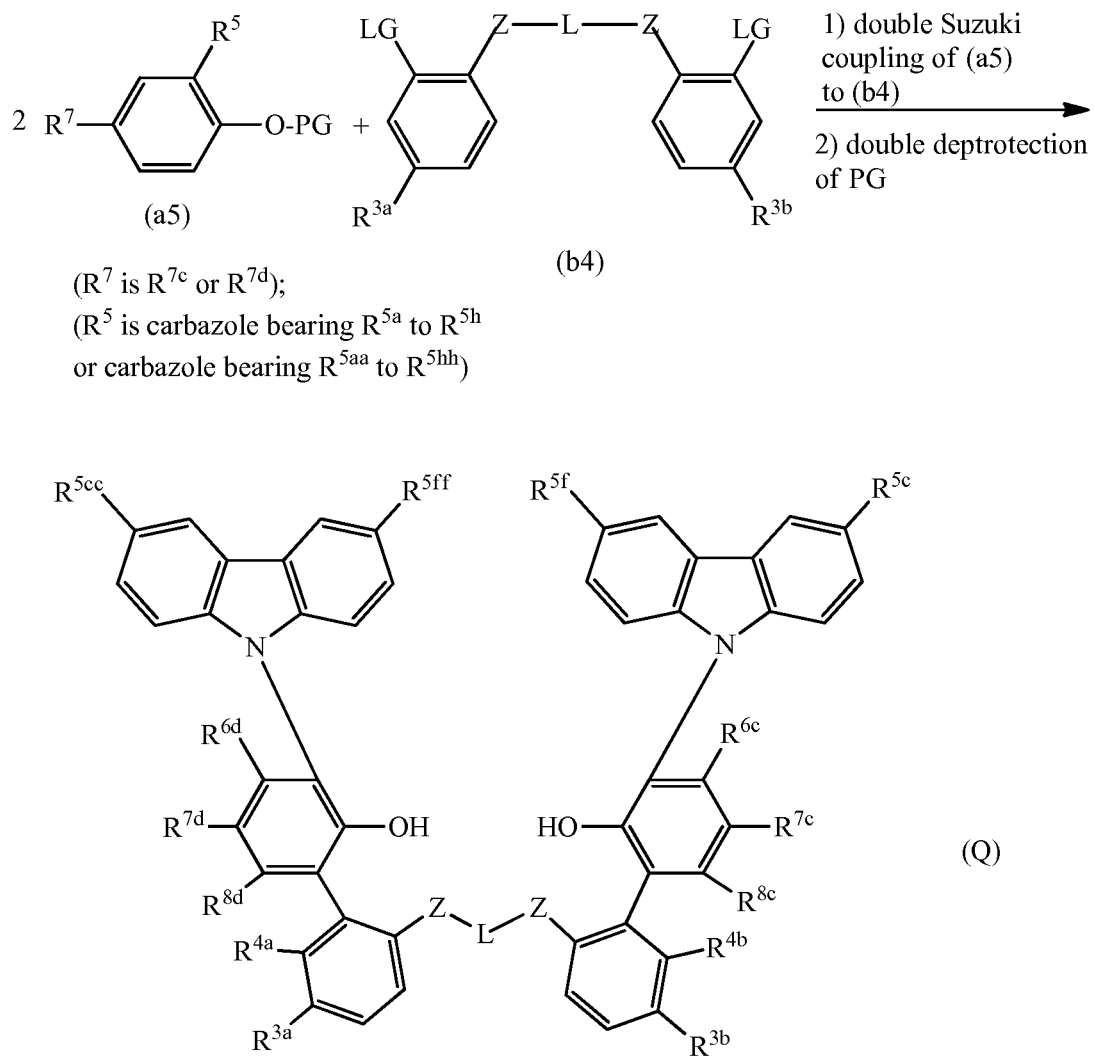
FIG. 3 shows an illustrative procedure for preparing the ligand of formula (Q) from the first and second primary intermediates.

An illustrative procedure for preparing the ligand of formula (Q) from the first and second primary intermediates is shown in FIG. 3. In FIG. 3, the preparation of the ligand of formula (Q) starts with a double Suzuki coupling of first primary intermediate (a5) (prepared as shown in FIG. 1) with second primary intermediate (b4) (prepared as shown in FIG. 2) to give a doubly PG-protected analog of ligand of formula (Q) (not shown), followed by double deprotection of the doubly PG-protected analog of ligand of formula (Q) that removes both protecting groups PG therefrom to give the ligand of formula (Q). The reactions described in FIG. 3 preferably are carried out under a substantially inert gas atmosphere in an anhydrous aprotic solvent such as, for example, diethyl ether, toluene, xylenes, tetrahydrofuran, diethylene glycol dimethyl ether, or a combination thereof and at a temperature in a range of from about −78° C. to about 200° C. The double-deprotection reaction can also be carried out in polar organic solvents such as, for example, acetic acid, acetone, ethyl acetate, acetonitrile, ethanol, a mixture thereof, and water-containing mixtures thereof and preferably further employs a deprotecting agent such as, for example, an acid (e.g., HCl in ethanol or trifluoroacetic acid in methylene chloride), a hydrogenolysis reaction (e.g., when PG is, for example, benzyl or CBZ) employing hydrogen gas and a palladium catalyst. Preferably, the reactions are carried out at atmospheric pressure.

Figure 4:
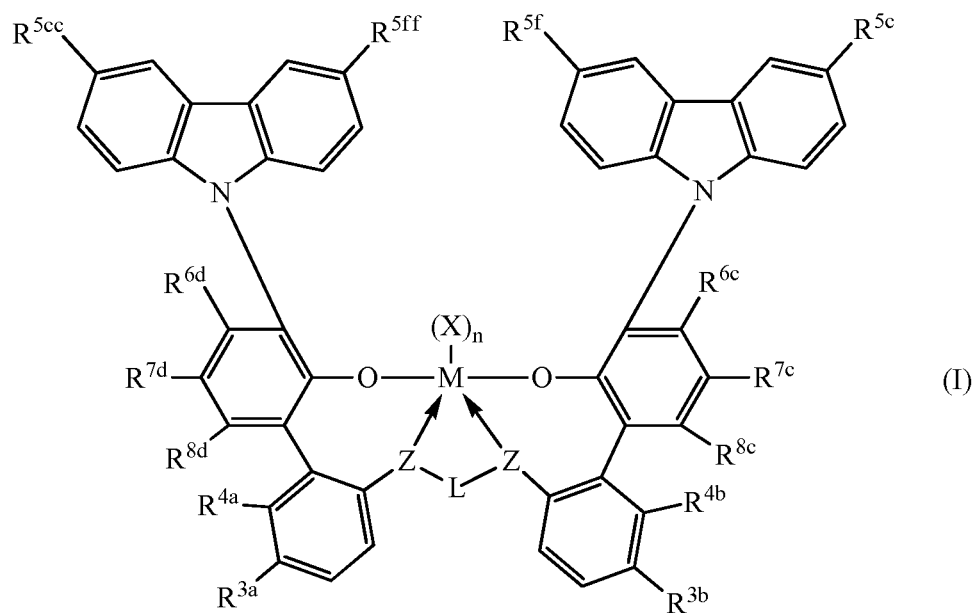
FIG. 4 shows an illustrative procedure for preparing the metal-ligand complex of formula (I) from the ligand of formula (Q).

An illustrative procedure for preparing the metal-ligand complex of formula (I) from the ligand of formula (Q) is shown in FIG. 4. In FIG. 4, the preparation of the metal-ligand complex of formula (I) involves reacting the ligand of formula (Q) (prepared as shown in FIG. 3) with a source or sources of M and X as shown, for example, in Options A to D. In option A, the compound of formula (Q) is doubly deprotonated with a non-nucleophilic base to give bisphenolate in situ (not shown), which is then allowed to react with a metal halide such as $M(Cl)_4$, wherein M is Zr, Hf, or Ti, followed by reaction of the resulting metal-ligand complex with a organometallic compound such as, for example, an organolithium (X-Li) or Grignard reagent (X—MgBr) (or organosodium (X—Na) or organopotassium (X—K)), wherein X is as defined above to give the compound of formula (I). Alternatively in option B, the compound of formula (Q) reacts with a metal-amido compound $M(NR^KR^L)_4$ wherein $R^K$ and $R^L$ are as defined previously for formula (I) to give an intermediate in situ (not shown), which then reacts with the organometallic compound X-Li or X—MgBr (e.g., organolithium or Grignard reagent) to give the compound of formula (I). In yet another option C, the compound of formula (Q) reacts with an organometallic compound $M(X)_4$ to give the compound of formula (I). In yet another alternative option D, the compound of formula (Q) reacts with the metal halide such as $M(Cl)_4$, followed by reaction of the resulting metal-ligand complex with 4 mole equivalents of an organometallic compound X-Li or X—MgBr such as, for example, methyl lithium or methyl magnesium bromide to give the compound of formula (I). The reactions described in FIG. 4 preferably are carried out under a substantially inert gas atmosphere in an anhydrous aprotic solvent such as, for example, toluene, xylenes, tetrahydrofuran, diethylene glycol dimethyl ether, or a combination thereof and at a temperature in a range of from about −78° C. to about 200° C. Preferably, the reactions are carried out at atmospheric pressure.

The invention contemplates procedures for preparing the metal-ligand complex of formula (I) and ligands of formula (Q) other than the previously described procedures illustrated in FIGS. 1 to 4. Such other procedures would be readily known to one of ordinary skill in the art in view of the teachings described herein. Examples of such other procedures are those readily adapted from procedures in U.S. Pat. No. 7,060,848 B2.

Turning to the invention catalyst, as mentioned previously, the invention process employs catalytic amounts of the invention catalyst. When more than one catalyst is employed in the invention process, each catalyst independently will be employed in a catalytic amount. The term "catalytic amount" means less than a stoichiometric quantity based on number of moles of a product yield-limiting stoichiometric reactant employed in the invention process. In the invention process the product-limiting stoichiometric reactant for the invention catalyst typically will be a polymerizable olefin (e.g., a product yield-limiting olefin monomer such as ethylene or olefin comonomer, whichever molar amount thereof is lower). The catalytic amount is also equal to or greater than a minimum amount of the metal-ligand complex of formula (I) that is necessary for at least some product of the catalyzed reaction to be formed and detected (e.g., by mass spectrometry). The minimum catalytic amount preferably is 0.001 mole percent of the number of moles of a product-limiting stoichiometric reactant. Preferably, the actual catalytic amount employed is greater than the minimum catalytic amount. More preferably, the catalytic amount of the metal-ligand complex of formula (I) used to prepare the invention catalyst is from 0.01 mol % to 50 mol % of the moles of the product yield-limiting polymerizable olefin. More preferably, the catalytic amount of the metal-ligand complex of formula (I) is at least 0.05 mol % thereof, and still more preferably at least 0.1 mol % thereof. Also more preferably, the catalytic amount of the metal-ligand complex of formula (I) is 40 mol % thereof or less, and still more preferably 35 mol % thereof or less.

Preferably the invention catalyst is characterized as having a minimum catalyst efficiency or greater. The catalyst efficiency is calculated by dividing the number of grams of the polyolefin copolymer prepared by the total number of grams of metal M of ingredient (a) employed (i.e., metal M of the at least one metal-ligand complex of formula (I)) (i.e., catalyst efficiency=g polyolefin copolymer prepared/g metal M of metal-ligand complex(es) of formula (I) employed). When the catalyst efficiency is determined, preferably the invention process of the first embodiment employs ethylene as the polymerizable olefin at a pressure of 450 pounds per square inch (psi, 3.4 megaPascals (MPa)); 125 grams of 1-octene as a second polymerizable olefin (i.e., the olefin comonomer); a reaction temperature of 190° C.; 0.10 micromole (μmol) of the metal-ligand complex of formula (I); 0.12 μmol of the activating co-catalyst, bis(octadecyl)methylammonium tetrakis(pentafluorophenyl)borate ([HNMe($C_{18}H_{37}$)$_2$][B($C_6F_5$)$_4$], abbreviated as BOMATPB); 1.0 μmol of another activating co-catalyst that is a triisobutylaluminum-modified methylalumoxane-3A (MMAO-3A); hydrogen gas; and toluene (or a mixed alkanes or cycloalkane) solvent, according to the experimental procedure described later. When determined in this manner, a particularly preferred invention catalyst is one that is characterized as having a catalyst efficiency of greater than 350,000, and more preferably greater than 390,000. When determined employing the ethylene/1-octene polymerization procedure described later except using 460 psi ethylene; 250 grams of 1-octene; 0.14 μmol of the metal-ligand complex of formula (I); 0.154 μmol of BOMATPB; 10 μmol MMAO-3A; and a reaction temperature of 170° C., a particularly preferred invention catalyst is one that is characterized as having a catalyst efficiency of greater than 1,700,000, and more preferably greater than 1,800,000. When determined employing the ethylene/1-butene polymerization procedure described later, a particularly preferred invention catalyst is one that is characterized as having a catalyst efficiency of greater than 1,000,000, and more preferably greater than 1,900,000. When determined employing the ethylene/propene/ethylidene norbornene procedure described later, a particularly preferred invention catalyst is one that is characterized as having a catalyst efficiency of greater than 390,000, more preferably greater than 440,000, still more preferably greater than 650,000, and even more preferably greater than 850,000. More preferably the catalyst efficiency is as defined as in any one of the Examples described later in the EXAMPLES OF THE PRESENT INVENTION section.

The invention catalyst can be successfully used at any effective reaction temperature, a practical effective temperature range being from 30° C. to 300° C. The invention catalyst is especially useful for high reaction temperature polymerizations of polymerizable olefins. The term "reaction temperature" means a degree of hotness or coldness of a polymerization mixture. In some embodiments the polymerizable olefins are polymerized in the invention process of the first embodiment at a reaction temperature of 30° C. to 250° C. In practice, a reaction temperature of from about 120° C. to 250° C. is preferred for optimizing yield of polyolefin copolymer product and other reaction parameters. In some embodiments the polymerizable olefins are polymerized in the invention process of the first embodiment at a reaction temperature of 130° C. or higher, in other embodiments at 150° C. or higher, in still other embodiments at 170° C. or higher, and in yet other embodiments at 190° C. or higher. In some embodiments a convenient upper reaction temperature for the polymerization of the polymerizable olefins is 300° C., in other embodiments at 250° C. or lower, and in still other embodiments at 220° C. or lower. In some embodiments of the invention process of the first embodiment the polymerizable olefins are polymerized at a preferred reaction temperature of from 150° C. to 250° C. The invention contemplates embodiments wherein a reaction temperature that is higher or lower than the foregoing reaction temperatures can be used depending upon the particular circumstances. Examples of such circumstances are reactivity of the catalyst, polymerizable olefin(s), or a combination thereof; the particular metal-ligand complex of formula (I), activating co-catalyst(s), or a combination thereof employed; amount of the metal-ligand complex of formula (I) employed; concentration of reactants; presence or absence of reaction additives such as the aforementioned molecular weight control agent, additional catalyst, or a combination thereof; position along the reaction coordinate of the reaction (e.g., in a variable reaction temperature process); presence or absence of solvent; reaction time desired; and configuration of the reactor employed (e.g., batch or continuous flow; stirred tank or not). More preferably the reaction temperature is as defined as in any one of the polymerization Examples described later in the EXAMPLES OF THE PRESENT INVENTION section.

In some embodiments, the invention catalyst, invention catalyst system or composition, or both further comprises at least one aprotic solvent (e.g., as in a solvated form of the invention catalyst), diluents (described later), or a combination thereof, as described herein. In other embodiments, the invention catalyst still further comprises a dispersant, e.g., an elastomer, preferably dissolved in the diluent. In these embodiments, the invention catalyst preferably comprises a homogeneous catalyst.

As mentioned before, in addition to the invention catalyst, in some embodiments the invention the invention process further employs the molecular weight control agent as an ingredient (e). These so-called molecular weight control embodiments of the invention process prepare the molecular weight-controlled polyolefin (e.g., molecular weight-controlled polyolefin copolymer). Examples of molecular weight control agents are chain shuttling agents such as trialkyl aluminum compounds and hydrogen gas ($H_2$).

In some embodiments the invention catalyst is characterizable as being a promiscuous olefin polymerization catalyst. That is, in such embodiments the invention catalyst is characterizable as having greater relative selectivity for polymerizing the aforementioned polymerizable ($C_3$-$C_{40}$)alpha-olefin over polymerizing ethylene than the non-invention ethylene selective catalysts mentioned later. The non-invention ethylene selective catalyst selectively polymerizes ethylene in the presence of the ($C_3$-$C_{40}$)alpha-olefin so as to prepare the poly(ethylene alpha-olefin) copolymer, and preferably the poly(ethylene alpha-olefin) block copolymer. Without wishing to be bound by theory, it is believed that requiring the both phenyl ether rings in formula (I) to be unsubstituted at ring positions thereof between one Z and $R^{3a}$ and the other Z and $R^{3b}$ allows the invention catalyst to adopt a conformation that is responsible for the promiscuous catalytic activity of the invention catalyst in such embodiments.

The embodiments wherein the invention catalyst is the promiscuous olefin polymerization catalyst, the invention catalyst is useful for copolymerizing ethylene and the ($C_3$-$C_{40}$)alpha-olefin and is characterizable as preferably having the aforementioned reactivity ratio $r_1$ of less than 20 ($r_1$<20). Degree of olefin comonomer incorporation into the polyolefin copolymer is inversely correlated to value of $r_1$ such that the lower the value of $r_1$, the higher the degree of comonomer incorporation and vice versa. An $r_1$ value of less than 20 is considered to be a high degree of comonomer incorporation. An $r_1$ value of greater than 30 is considered to be a low degree of comonomer incorporation. In some embodiments $r_1$ is 15 or less. In other embodiments $r_1$ is 12 or less. In still other embodiments $r_1$ is less than 12.

For copolymers produced by a given catalyst, the relative amounts of comonomer and monomer in the copolymer and hence the copolymer composition is determined by relative rates of reaction of comonomer and monomer. Mathematically the molar ratio of comonomer to monomer is given by $$\frac{F_2}{F_1} = \left(\frac{[\text{comonomer}]}{[\text{monomer}]}\right)_{polymer} = \frac{R_{p2}}{R_{p1}} \tag{1}$$

Here $R_{p2}$ and $R_{p1}$ are the rates of polymerization of comonomer and monomer respectively and $F_2$ and $F_1$ are the mole fractions of each in the copolymer. Because $F_1+F_2=1$ we can rearrange this equation to $$F_2 = \frac{R_{p2}}{R_{p1} + R_{p2}} \tag{2}$$

The individual rates of polymerization of comonomer and monomer are typically complex functions of reaction temperature, catalyst employed, and monomer/comonomer concentrations. In the limit as comonomer concentration in the reaction media drops to zero, $R_{p2}$ drops to zero, $F_2$ becomes zero and the polymer consists of pure monomer. In the limiting case of no monomer in the reactor $R_{p1}$ becomes zero and $F_2$ is one (provided the comonomer can polymerize alone).

For most homogeneous catalysts the ratio of comonomer to monomer in the reactor largely determines polymer composition as determined according to either the Terminal Copolymerization Model or the Penultimate Copolymerization Model.

For random copolymers in which the identity of the last monomer inserted dictates the rate at which subsequent monomers insert, the terminal copolymerization model is employed. In this model insertion reactions of the type $$\ldots M_i C^* + M_j \xrightarrow{k_{ij}} \ldots M_i M_j C^* \tag{3}$$

where $C^*$ represents the catalyst, $M_i$ represents monomeri, and $k_{ij}$ is the rate constant having the rate equation $$R_{p_{ij}} = k_{ij}[\ldots M_i C^*][M_j] \tag{4}$$

The comonomer mole fraction (i=2) in the reaction media is defined by the equation:

$$f_2 = \frac{[M_2]}{[M_1] + [M_2]} \tag{5}$$

A simplified equation for comonomer composition can be derived as disclosed in George Odian, *Principles of Polymerization*, Second Edition, John Wiley and Sons, 1970, as follows:

$$F_2 = \frac{r_1(1-f_2)^2 + (1-f_2)f_2}{r_1(1-f_2)^2 + 2(1-f_2)f_2 + r_2 f_2^2}. \tag{6}$$

From this equation the mole fraction of comonomer in the polymer is solely dependent on the mole fraction of comonomer in the reaction media and two temperature dependent reactivity ratios defined in terms of the insertion rate constants as:

$$r_1 = \frac{k_{11}}{k_{12}} \tag{7}$$

$$r_2 = \frac{k_{22}}{k_{21}}.$$

Alternatively, in the penultimate copolymerization model, the identities of the last two monomers inserted in the growing polymer chain dictate the rate of subsequent monomer insertion. The polymerization reactions are of the form $$\ldots M_i M_j C^* + M_k \xrightarrow{k_{ijk}} \ldots M_i M_j M_k C^* \tag{8}$$

and the individual rate equations are:

$$R_{p_{ijk}} = k_{ijk}[\ldots M_i M_j = C^*][M_k] \tag{9}.$$

The comonomer content can be calculated (again as disclosed in George Odian, Supra.) as:

$$\frac{(1-F_2)}{F_2} = \frac{1 + \frac{r_1' X(r_1 X + 1)}{(r_1' X + 1)}}{1 + \frac{r_2'(r_2 + X)}{X(r_2' + X)}} \tag{10}$$

where X is defined as:

$$X = \frac{(1-f_2)}{f_2} \tag{11}$$

and the reactivity ratios are defined as:

$$r_1 = \frac{k_{111}}{k_{112}} \tag{12}$$

$$r_1' = \frac{k_{211}}{k_{212}}$$

$$r_2 = \frac{k_{222}}{k_{221}}$$

$$r_2' = \frac{k_{122}}{k_{121}}.$$

For this model as well the polymer composition is a function only of temperature dependent reactivity ratios and comonomer mole fraction in the reactor. The same is also true when reverse comonomer or monomer insertion may occur or in the case of the interpolymerization of more than two monomers.

Reactivity ratios for use in the foregoing models may be predicted using well known theoretical techniques or empirically derived from actual polymerization data. Suitable theoretical techniques are disclosed, for example, in B. G. Kyle, *Chemical and Process Thermodynamics*, Third Addition, Prentice-Hall, 1999 and in Redlich-Kwong-Soave (RKS) Equation of State, *Chemical Engineering Science,* 1972, pp 1197-1203. Commercially available software programs may be used to assist in deriving reactivity ratios from experimentally derived data. One example of such software is Aspen Plus from Aspen Technology, Inc., Ten Canal Park, Cambridge, Mass. 02141-2201 USA.

In embodiments of the invention process employing the invention catalyst as the promiscuous olefin polymerization catalyst, the invention process further employs ethylene, the $(C_3-C_{40})$alpha-olefin, and a combination of a chain shuttling agent and the non-invention ethylene selective polymerization catalyst. The non-invention ethylene selective polymerization catalyst is characterizable as having a reactivity ratio $r_1$ greater than 20, preferably greater than 30, and more preferably greater than 50. In these so-called chain shuttling embodiments of the invention process, the chain shuttling agent (CSA) is the aforementioned ingredient (e) and the non-invention ethylene selective polymerization catalyst is the aforementioned ingredient (f). If desired, in some of such embodiments the molecular weight control agent (e.g., hydrogen gas) can also be employed as another ingredient (e).

The chain shuttling embodiments of the invention process preferably produce the polyolefin copolymer as a poly(ethylene alpha-olefin) block copolymer, which has at least one hard segment and at least one soft segment. The non-invention ethylene selective polymerization catalyst, where it is employed in the chain shuttling embodiments of the invention process, produces at least one polyethylene hard segment of the poly(ethylene alpha-olefin) block copolymer in the presence of the alpha-olefin and the invention catalyst that is the promiscuous olefin polymerization catalyst gives at least one soft segment of the poly(ethylene alpha-olefin) copolymer, the soft segment comprising residuals of ethylene and the alpha-olefin. The contacting step comprises a continuous polymerization process that is performed under olefin polymerizing conditions (described later) and preferably prepares the poly(ethylene alpha-olefin) block copolymer in one polymerization reactor. Preferably the poly(ethylene alpha-olefin) block copolymer comprises a segment rich in polyethylene (a hard segment) characterizable by a high melting temperature ($T_m>100°$ C.) and a segment rich in residuals from the alpha-olefin and ethylene (a soft segment). Preferably the alpha-olefin employed in the chain shuttling embodiments of the invention process is the $(C_3-C_{40})$alpha-olefin.

Suitable chain shuttling agents are known. As used herein, the term "chain shuttling agent" means a molecule characterizable, without limitation, as functioning in the chain shuttling embodiments of the invention process in such a way that polymer chains are transferred between two distinct catalysts with different monomer selectivities in a single polymerization reactor. That is, the chain shuttling agent (CSA) is a molecule characterizable, without limitation, as functioning in such a way that during the continuous process polymer chains are transferred between the invention catalyst comprising a mixture or reaction product of ingredients (a) and (b) and that functions as the promiscuous olefin polymerization catalyst and the non-invention ethylene selective catalyst. Typically, chain shuttling agents comprise a first metal that is Al, B, or Ga, the first metal being in a formal oxidation state of +3; or a second metal that is Zn or Mg, the second metal being in a formal oxidation state of +2. Preferred chain shuttling agents are described in U.S. Patent Application Publication Number US 2007/0167315. Chain shuttling agents suitable for use with the catalyst system in the chain shuttling embodiments of the invention process include diethylzinc, di(1-butyl)zinc, di(n-hexyl)zinc, triethylaluminum, trioctylaluminum, triethylgallium, i-butylaluminum bis(dimethyl(t-butyl)siloxane), i-butylaluminum bis(di(trimethylsilyl)amide), n-octylaluminum di(pyridine-2-methoxide), bis(n-octadecyl)i-butylaluminum, i-butylaluminum bis(di(n-pentyl)amide), n-octylaluminum bis(2,6-di-t-butylphenoxide), n-octylaluminum di(ethyl(1-naphthyl)amide), ethylaluminum bis(t-butyldimethylsiloxide), ethylaluminum di(bis(trimethylsilyl)amide), ethylaluminum bis(2,3,6,7-dibenzo-1-azacycloheptaneamide), n-octylaluminum bis(2,3,6,7-dibenzo-1-azacycloheptaneamide), n-octylaluminum bis(dimethyl(t-butyl)siloxide, ethylzinc (2,6-diphenylphenoxide), and ethylzinc (t-butoxide).

In some embodiments, when preparing the poly(ethylene alpha-olefin) block copolymer according to the chain shuttling embodiments of the invention process, the process employs a catalyst system comprising a mixture or reaction product of:

(A) a first olefin polymerization catalyst, the first olefin polymerization catalyst being characterized as having a high comonomer incorporation index (described later; e.g., a comonomer incorporation index of 15 mole percent of comonomer or higher);

(B) a second olefin polymerization catalyst, the second olefin polymerization catalyst being characterized as having a comonomer incorporation index that is less than 90 percent of the comonomer incorporation index of the first olefin polymerization catalyst; and (C) the chain shuttling agent;

the first olefin polymerization catalyst comprising the invention catalyst as described in the first embodiment, wherein the promiscuous olefin polymerization catalyst comprises the invention catalyst.

The comonomer incorporation index is another means of characterizing the high olefin comonomer incorporation characteristic of the invention catalyst and can be used instead of $r_1$. In some embodiments, the amount of the $(C_3-C_{40})$alpha-olefin comonomer incorporated into a polyolefin copolymer (e.g., a rich polyethylene, poly(ethylene alpha-olefin) copolymer, or a segment (e.g., the hard and soft segments) of the poly(ethylene alpha-olefin) block copolymer) can be characterized by the aforementioned comonomer incorporation index. As used herein, the term, "comonomer incorporation index", refers to the mole percent of residuals of comonomer incorporated into an ethylene/comonomer copolymer, or ethylene-derived hard segment thereof, prepared under representative olefin polymerization conditions (described later herein), ideally under steady-state, continuous solution polymerization conditions in a hydrocarbon diluent at 100° C., 4.5 megapascals (MPa) ethylene pressure (reactor pressure), greater than 92 percent (more preferably greater than 95 percent) ethylene conversion, and greater than 0.01 percent comonomer conversion. The selection of metal-ligand complexes or catalyst compositions having the greatest difference in comonomer incorporation indices results in copolymers from two or more monomers having the largest difference in block or segment properties, such as density.

Monomer and comonomer content of the polyolefin copolymers prepared by the invention process may be measured using any suitable technique such as, for example, infrared (IR) spectroscopy, especially the aforementioned FT-IR spectroscopy, and nuclear magnetic resonance (NMR) spectroscopy, with techniques based on NMR spectroscopy being preferred and carbon-13 NMR spectroscopy being more preferred. Using carbon-13 NMR spectroscopy, prepare an analysis sample from a polymer sample of the high density polyethylene or poly(ethylene alpha-olefin) block copolymer by adding approximately 3 g of a 50/50 mixture of tetrachloroethane-$d^2$/orthodichlorobenzene to 0.4 g of the polymer sample in a 10 millimeter (mm) NMR tube. Dissolve and homogenize the polymer sample by heating the tube and its contents to 150° C. Collect carbon-13 NMR spectroscopy data using a JEOL Eclipse™ 400 MHz spectrometer or a Varian Unity Plus™ 400 MHz spectrometer, corresponding to a carbon-13 resonance frequency of 100.5 MHz. Acquire the carbon-13 data using 4000 transients per data file with a 6 second pulse repetition delay. To achieve minimum signal-to-noise for quantitative analysis, add multiple data files together. The spectral width is 25,000 Hz with a minimum file size of 32,000 data points. Analyze the analysis sample at 130° C. in a 10 mm broad band probe. Determine the comonomer incorporation with the carbon-13 data using Randall's triad method (Randall, J. C.; JMS-Rev. Macromol. Chem. Phys., C29, 201-317 (1989), which is incorporated by reference herein in its entirety.

In certain circumstances the comonomer incorporation index may be determined directly, for example by the use of NMR spectroscopic techniques described previously or by IR spectroscopy. If NMR or IR spectroscopic techniques cannot be used, then any difference in comonomer incorporation is indirectly determined. For polymers formed from multiple monomers this indirect determination may be accomplished by various techniques based on monomer reactivities.

The "first olefin polymerization catalyst" is interchangeably referred to herein as "Catalyst (A)." In some embodiments, the first olefin polymerization catalyst (Catalyst (A)) means the aforementioned "promiscuous olefin polymerization catalyst." The "second olefin polymerization catalyst" is interchangeably referred to herein as "Catalyst (B)." The first and second olefin polymerization catalysts (i.e., Catalyst (A) and Catalyst (B)) have different ethylene and ($C_3$-$C_{40}$)alpha-olefin selectivities.

In some embodiments more than one Catalysts (B), more than one Catalysts (A), or both independently can be employed in the invention process, including the chain shuttling embodiments of the invention process. More preferably, the invention catalyst that comprises a mixture or reaction product of the ingredients (a) and (b) as described in the first embodiment is a Catalyst (A), but not Catalyst (B). Preferably, the comonomer incorporation index of Catalyst (B) is less than 50 percent and more preferably less than 5 percent of the comonomer incorporation index of Catalyst (A). Preferably, the comonomer incorporation index for Catalyst (A) is greater than 20 mol %, more preferably greater than 30 mol %, and still more preferably greater than 40 mol % incorporation of comonomer.

In addition to employing the embodiment of the invention catalyst that is the promiscuous olefin polymerization catalyst as the Catalyst (A), at least one non-invention promiscuous olefin polymerization catalysts can also be employed as additional Catalyst(s) (A). Preferably, such non-invention Catalysts (A) are those described in US 2006/0199930 A1; US 2007/0167578 A1; US 2008/0311812 A1; U.S. Pat. No. 7,355,089 B2; or WO 2009/012215 A2. Also in such embodiments, the catalyst system further comprises the ethylene selective non-invention catalyst, which is the non-invention Catalyst (B) (i.e., a Catalyst (B) that is other than the invention catalyst that comprises a mixture or reaction product of the ingredients (a) and (b), wherein ingredients (a) and (b) are as described previously for the first embodiment). Preferably the ethylene selective non-invention catalyst that is the non-invention Catalyst (B) is a Catalyst (B) described in US 2006/0199930 A1; US 2007/0167578 A1; US 2008/0311812 A1; U.S. Pat. No. 7,355,089 B2; or WO 2009/012215 A2.

Representative non-invention Catalysts (A) and (B) of US 2006/0199930 A1; US 2007/0167578 A1; US 2008/0311812 A1; U.S. Pat. No. 7,355,089 B2; or WO 2009/012215 A2 are the catalysts of formulas (A1) to (A5), (B1), (B2), (C1) to (C3), and (D1):

Catalyst (A1) is [N-(2,6-di(1-methylethyl)phenyl)amido)(2-isopropylphenyl)(α-naphthalen-2-diyl(6-pyridin-2-diyl)methane)]hafnium dimethyl, prepared according to the teachings of WO 03/40195, 2003US0204017, U.S. Ser. No. 10/429,024, filed May 2, 2003, and WO 04/24740, and having the structure:

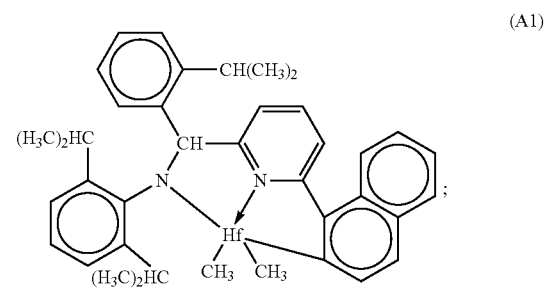

(A1)

Catalyst (A2) is [N-(2,6-di(1-methylethyl)phenyl)amido)(2-methylphenyl)(1,2-phenylene-(6-pyridin-2-diyl)methane)]hafnium dimethyl, prepared according to the teachings of WO 03/40195, 2003US0204017, U.S. Ser. No. 10/429,024, filed May 2, 2003, and WO 04/24740, and having the structure:

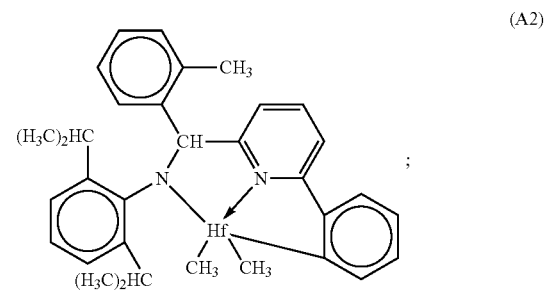

(A2)

Catalyst (A3) is bis[N,N'''-(2,4,6-tri(methylphenyl)amido)ethylenediamine]hafnium dibenzyl, and having the structure:

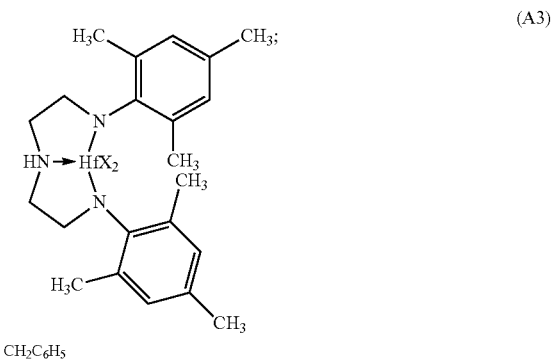

(A3)

Catalyst (A4) is bis((2-oxoyl-3-(dibenzo-1H-pyrrole-1-yl)-5-(methyl)phenyl)-2-phenoxymethyl)cyclohexane-1,2-diyl zirconium (IV) dibenzyl, prepared substantially according to the teachings of US-A-2004/0010103, and having the structure:

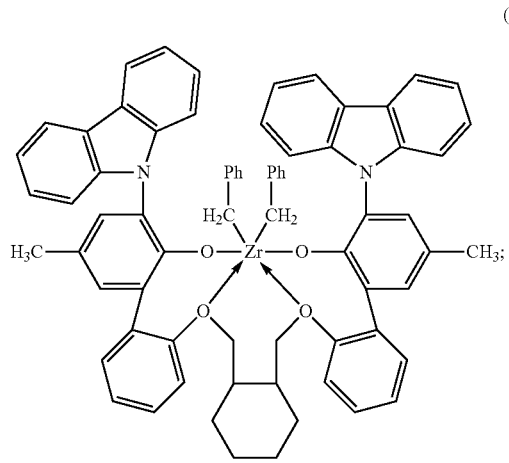

(A4)

(Ph is phenyl)

Catalyst (A5) is [η²-2-2,6-diisopropyl-N-(2-methyl-3-(octylimino)butan-2-yl)benzeneamide]trimethylhafnium, prepared substantially according to the teachings of WO 2003/051935, and having the structure:

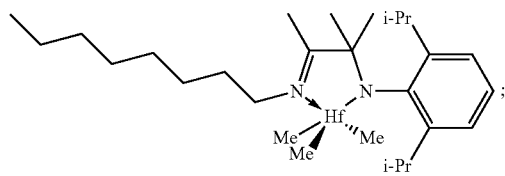

(A5)

(Me is methyl and i-Pr is ispropyl)

Catalyst (B1) is 1,2-bis-(3,5-di-t-butylphenylene)(1-(N-(1-methylethyl)imino)methyl)(2-oxoyl)zirconium dibenzyl, and having the structure:

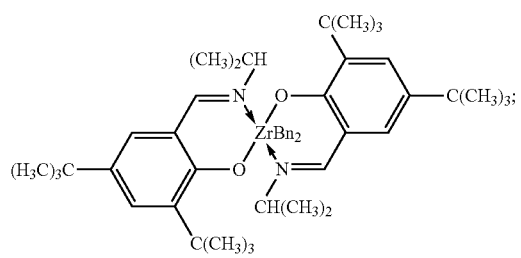

(B1)

Bn = CH₂C₆H₅

Catalyst (B2) is 1,2-bis-(3,5-di-t-butylphenylene)(1-(N-(2-methylcyclohexyl)-imino)methyl)(2-oxoyl) zirconium dibenzyl, and having the structure:

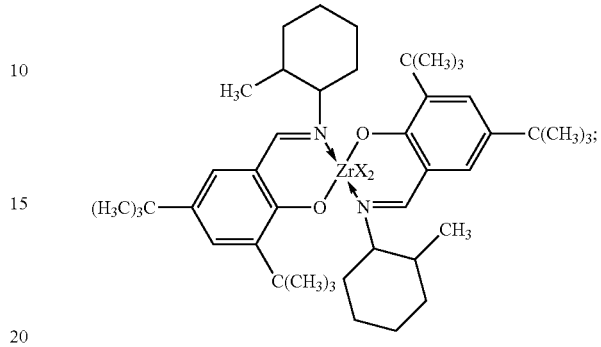

(B2)

X = CH₂C₆H₅

Catalyst (C1) is (t-butylamido)dimethyl(3-N-pyrrolyl-1,2,3,3a,7a-η-inden-1-yl)silanetitanium dimethyl, prepared substantially according to the techniques of U.S. Pat. No. 6,268,444, and having the structure:

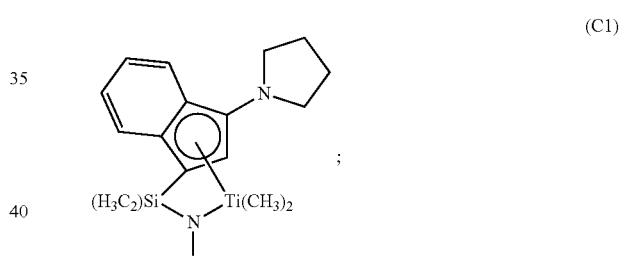

(C1)

Catalyst (C2) is (t-butylamido)di(4-methylphenyl)(2-methyl-1,2,3,3a,7a-η-inden-1-yl)silanetitanium dimethyl, prepared substantially according to the teachings of US-A-2003/004286, and having the structure:

(C2)

Catalyst (C3) is (t-butylamido)di(4-methylphenyl)(2-methyl-1,2,3,3a,8a-η-s-indacen-1-yl)silanetitanium dimethyl, prepared substantially according to the teachings of US-A-2003/004286, and having the structure:

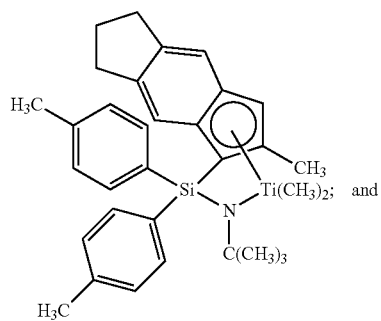

(C3)

Catalyst (D1) is bis(dimethyldisiloxane)(indene-1-yl)zirconium dichloride, available from Sigma-Aldrich, and having the structure:

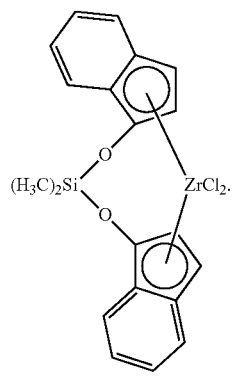

(D1)

The metal-ligand complex of formula (I), and the aforementioned non-invention catalysts for that matter, are rendered catalytically active by using an activating technique such as those that are known in the art for use with metal-based olefin polymerization reactions or, preferably, by contacting it to, or combining it with, the at least one activating co-catalyst. Suitable activating co-catalysts for use herein include Lewis acid activating co-catalysts are Group 13 metal compounds. Preferred Lewis acid activating co-catalysts are Group 13 metal compounds containing from 1 to 3 hydrocarbyl substituents as described herein. Examples of such suitable activating cocatalysts are boron-containing ionic compounds; alkyl aluminums; polymeric or oligomeric alumoxanes (also known as aluminoxanes); neutral Lewis acids; and non-polymeric, non-coordinating, ion-forming compounds (including the use of such compounds under oxidizing conditions). A suitable activating technique is bulk electrolysis (explained in more detail hereinafter). Combinations of at least one of the foregoing activating co-catalysts, activating techniques, or activating co-catalysts and techniques are also contemplated.

In some embodiments the at least one activating co-catalyst comprises the alkyl aluminum. The term "alkyl aluminum" means a monoalkyl aluminum dihydride or monoalkylaluminum dihalide, a dialkyl aluminum hydride or dialkyl aluminum halide, or a trialkylaluminum. Preferably, the alkylaluminum comprises an alkylaluminum compound of formula (II): $Al(R^A)(R^B)(R^C)$ (II), wherein $R^A$ is $(C_1$-$C_{40})$alkyl, and each of $R^B$ and $R^C$ independently is $(C_1$-$C_{40})$alkyl, hydride, or halide. Aluminoxanes and their preparations are known at, for example, U.S. Pat. No. 6,103,657. Examples of preferred polymeric or oligomeric alumoxanes are methylalumoxane, triisobutylaluminum-modified methylalumoxane, and isobutylalumoxane.

In some embodiments the at least one activating co-catalyst comprises the a boron-containing ionic compound. More preferred Group 13 metal compounds are tri(hydrocarbyl)-substituted-aluminum or tri(hydrocarbyl)-boron compounds, still more preferred are tri($(C_1$-$C_{10})$alkyl)aluminum or tri $((C_6$-$C_{18})$aryl)boron compounds and halogenated (including perhalogenated) derivatives thereof, even more especially tris(fluoro-substituted phenyl)boranes, still even more especially tris(pentafluorophenyl)borane. In some embodiments, the activating co-catalyst is a tris($(C_1$-$C_{20})$hydrocarbyl)borate (e.g., trityl tetrafluoroborate) or a tri($(C_1$-$C_{20})$hydrocarbyl)ammonium tetra($(C_1$-$C_{20})$hydrocarbyl)borane (e.g., bis(octadecyl)methylammonium tetrakis(pentafluorophenyl)borane). As used herein, the term "ammonium" is synonymous with the term "ammonium-type cation" and means a nitrogen bearing a formal charge of +1. The ammonium-type cation preferably is an ammonium-type organic cation, which preferably is a $((C_1$-$C_{20})$hydrocarbyl)$_3$N(H)$^+$, a $((C_1$-$C_{20})$hydrocarbyl)$_2$N(H)$_2^+$, or $(C_1$-$C_{20})$hydrocarbylN(H)$_3^+$. The ammonium-type cation $((C_1$-$C_{20})$hydrocarbyl)$_3$N(H)$^+$ is more preferred. As used here, each $(C_1$-$C_{20})$hydrocarbyl independently may be the same or different.

The boron-containing ionic compound comprises a cation and a boron-containing anion. Preferably, the boron-containing anion is a tetra-substituted boron anion (i.e., a borate) or is derived in situ during the invention process from a tri-substituted boron (i.e., a borane) and an anionic ligand one of X of formula (I). The substituents of the tetra-substituted boron and trisubstituted boron preferably are halo or $(C_1$-$C_{20})$hydrocarbyl. A more preferred tri-substituted boron is B($(C_1$-$C_{20})$hydrocarbyl)$_3$ (e.g., tris(pentafluorophenyl borane). A more preferred tetra-substituted boron anion is [B($(C_1$-$C_{20})$hydrocarbyl)$_4$]$^-$ (e.g., trityl tetrakis(pentafluorophenyl)borate). A still more preferred boron-containing ionic compound is a tri($(C_1$-$C_{20})$hydrocarbyl)ammonium tetra($(C_1$-$C_{20})$hydrocarbyl)borate (e.g., bis(octadecyl)methylammonium tetrakis(pentafluorophenyl)borate ([HNMe$(C_{18}H_{37})_2$][B$(C_6F_5)_4$], abbreviated as BOMATPB)). Preferably, the cation comprises the ammonium-type cation or hydrocarbon cation (e.g., triphenylmethyl cation).

Preferred combinations of neutral Lewis acid activating co-catalysts include mixtures comprising a combination of a tri($(C_1$-$C_4)$alkyl)aluminum and a halogenated tri($(C_6$-$C_{18})$aryl)boron compound, especially a tris(pentafluorophenyl)borane. Also preferred are combinations of such neutral Lewis acid mixtures with a polymeric or oligomeric alumoxane, and combinations of a single neutral Lewis acid, especially tris(pentafluorophenyl)borane with a polymeric or oligomeric alumoxane. Preferred ratios of numbers of moles of (metal-ligand complex):(tris(pentafluoro-phenylborane):(alumoxane) [e.g., (Group 4 metal-ligand complex):(tris(pentafluoro-phenylborane):(alumoxane)] are from 1:1:1 to 1:10:30, more preferably from 1:1:1.5 to 1:5:10.

Many suitable activating co-catalysts and activating techniques have been previously taught with respect to different metal-ligand complexes in the following USPNs: U.S. Pat. No. 5,064,802; U.S. Pat. No. 5,153,157; U.S. Pat. No. 5,296, 433; U.S. Pat. No. 5,321,106; U.S. Pat. No. 5,350,723; U.S.

Pat. No. 5,425,872; U.S. Pat. No. 5,625,087; U.S. Pat. No. 5,721,185; U.S. Pat. No. 5,783,512; U.S. Pat. No. 5,883,204; U.S. Pat. No. 5,919,983; U.S. Pat. No. 6,696,379; and U.S. Pat. No. 7,163,907. Examples of suitable hydrocarbyloxides are disclosed in U.S. Pat. No. 5,296,433. Examples of suitable Bronsted acid salts for addition polymerization catalysts are disclosed in U.S. Pat. No. 5,064,802; U.S. Pat. No. 5,919,983; U.S. Pat. No. 5,783,512. Examples of suitable salts of a cationic oxidizing agent and a non-coordinating, compatible anion as activating co-catalysts for addition polymerization catalysts are disclosed in U.S. Pat. No. 5,321,106. Examples of suitable carbenium salts as activating co-catalysts for addition polymerization catalysts are disclosed in U.S. Pat. No. 5,350,723. Examples of suitable silylium salts as activating co-catalysts for addition polymerization catalysts are disclosed in U.S. Pat. No. 5,625,087. Examples of suitable complexes of alcohols, mercaptans, silanols, and oximes with tris(pentafluorophenyl)borane are disclosed in U.S. Pat. No. 5,296,433. Some of these catalysts are also described in a portion of U.S. Pat. No. 6,515,155 B1 beginning at column 50, at line 39, and going through column 56, at line 55, only the portion of which is incorporated by reference herein.

In some embodiments at least two of the foregoing activating co-catalysts are used in combination with each other. An especially preferred combination is a mixture of a tri(($C_1$-$C_4$)hydrocarbyl)aluminum, tri(($C_1$-$C_4$)hydrocarbyl)borane, or an ammonium borate (preferably BOMATPB) with an oligomeric or polymeric alumoxane compound.

The ratio of total number of moles of the at least one metal-ligand complex of formula (I) to total number of moles of the at least one activating co-catalyst is from 1:10,000 to 100:1. Preferably, the ratio is at least 1:5000, more preferably at least 1:1000; and 10:1 or less, more preferably 1:1 or less. When an alumoxane alone is used as the activating co-catalyst, preferably the number of moles of the alumoxane that are employed is at least 100 times the number of moles of the metal-ligand complex of formula (I). When tris(pentafluorophenyl)borane alone is used as the activating co-catalyst, preferably the number of moles of the tris(pentafluorophenyl)borane that are employed to the total number of moles of at least one metal-ligand complex of formula (I) form 0.5:1 to 10:1, more preferably from 1:1 to 6:1, still more preferably from 1:1 to 5:1. The remaining activating co-catalysts are generally employed in approximately mole quantities of from equal to 1.2 times the total mole quantities of at least one metal-ligand complex of formula (I).

As mentioned before, the invention process employs olefin polymerizing conditions. In some embodiments, the olefin polymerizing conditions independently produce the invention catalyst in situ that is formed by combination or reaction of the metal-ligand complex of formula (I) and the at least one activating co-catalyst of ingredient (b). The invention catalyst system comprises the invention catalyst and at least one other ingredient of the invention process. Such other ingredients include, but are not limited to, (i) polymerizable olefin(s); (ii) another metal-ligand complex of formula (I); (iii) at least one non-invention Catalyst (A); (iv) at least one non-invention Catalyst (B); (v) chain shuttling agent; (vi) a catalyst stabilizer (if any); (vii) a solvent (if any); and (viii) a mixture of any two or more thereof.

Olefin polymerizing conditions independently refer to reaction conditions such as solvent(s), atmosphere(s), temperature(s), pressure(s), time(s), and the like of the invention polymerization reaction that are preferred for giving, after 15 minutes reaction time, at least a 10 percent (%), more preferably at least 20%, and still more preferably at least 30% reaction yield of the polyolefin copolymer from the invention process. Preferably, the invention process is independently are run under an inert atmosphere (e.g., under an inert gas consisting essentially of, for example, nitrogen gas, argon gas, helium gas, or a mixture of any two or more thereof). Other atmospheres are contemplated, however, and these include sacrificial olefin in the form of a gas and hydrogen gas (e.g., as a polymerization termination agent). In some aspects, the invention process independently is run without any solvent, i.e., is a neat process that is run in a neat mixture of ingredients (a) to (c) or in a neat mixture of ingredients (a) to (d), as the case may be, wherein excess amount of ingredient (c), (d), or ingredients (c) and (d) can function as the aprotic solvent. In other aspects, the neat mixture further contains additional ingredients (e.g., catalyst stabilizer such as triphenylphosphine) other than solvent(s). In still other aspects, the invention process is run with the aprotic solvent or mixture of two or more aprotic solvents, i.e., is a solvent-based process that is run as a solvent-containing mixture of ingredients (a) to (c) or a solvent-containing mixture of ingredients (a) to (d), as the case may be, and at least one solvent, e.g., an aprotic solvent. Preferably, the neat process or solvent-based process is run at a reaction temperature of the neat mixture or solvent-containing mixture as described previously. Preferably the invention process independently is run under a reaction pressure of from about 0.9 atmospheres (atm) to about 10 atm (i.e., from about 91 kiloPascals (kPa) to about 1010 kPa). More preferably, the pressure is about 1 atm (i.e., about 101 kPa).

In some embodiments, polymerizable olefins useful in the invention process are hydrocarbons, typically ($C_2$-$C_{40}$)hydrocarbons consisting of from 2 to 40 carbon atoms (although the number of carbon atoms could be higher as mentioned previously) and hydrogen atoms and containing at least 1, and preferably no more than 3, and more preferably no more than 2, carbon-carbon double bonds. The ($C_2$)hydrocarbon is ethylene. In some embodiments, from 1 to 4 hydrogen atoms of the ($C_2$-$C_{40}$)hydrocarbons are replaced, each by a halogen atom, preferably fluoro or chloro to give halogen atom-substituted ($C_2$-$C_{40}$)hydrocarbons as the useful polymerizable olefins. The ($C_2$-$C_{40}$)hydrocarbons (not halogen atom-substituted) are preferred. Preferred polymerizable olefins (i.e., olefin monomers) useful for making the polyolefin copolymers are ethylene and polymerizable ($C_3$-$C_{40}$)olefins. The ($C_3$-$C_{40}$)olefins include a ($C_3$-$C_{40}$)alpha-olefin, a cyclic olefin, styrene, and a cyclic or acyclic diene. In some embodiments at least one of the other polymerizable olefin is the alpha-olefin, and more preferably a ($C_3$-$C_{40}$)alpha-olefin. In some embodiments the ($C_3$-$C_{40}$)alpha-olefin is a ($C_4$-$C_{40}$) alpha-olefin, more preferably a ($C_6$-$C_{40}$)alpha-olefin, still more preferably a ($C_7$-$C_{40}$)alpha-olefin, and even more preferably a ($C_8$-$C_{40}$)alpha-olefin. Preferably, the ($C_3$-$C_{40}$)alpha-olefin comprises a branched chain ($C_3$-$C_{40}$)alpha-olefin, still more preferably a linear-chain ($C_3$-$C_{40}$)alpha-olefin, even more preferably a linear chain ($C_3$-$C_{40}$)alpha-olefin of formula (A): $CH_2=CH_2-(CH_2)_zCH_3$ (A), wherein z is an integer of from 0 to 40, and yet even more preferably a linear-chain ($C_3$-$C_{40}$)alpha-olefin that is 1-propene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, or a linear-chain ($C_{20}$-$C_{24}$)alpha-olefin. Preferably the cyclic olefin is a ($C_3$-$C_{40}$)cyclic olefin. Preferably, the cyclic or acyclic diene is a ($C_4$-$C_{40}$)diene, preferably an acyclic diene, more preferably an acyclic conjugated ($C_4$-$C_{40}$)diene, more preferably an acyclic 1,3-conjugated ($C_4$-$C_{40}$)diene, and still more preferably 1,3-butadiene.

Preferably in the invention process, the mole ratio of (moles of ($C_3$-$C_{40}$)alpha-olefin)/(moles of ethylene) is 0.1 or higher, more preferably 0.30 or higher, still more preferably 0.50 or higher, and even more preferably 0.75 or higher (e.g., 1.0 or higher).

Polyolefin copolymers that can be made by the invention process include copolymers of two or more of the aforementioned polymerizable olefins. Such polyolefin copolymers include, for example, rich polyethylene and interpolymers that comprise residuals of ethylene and at least one polymerizable ($C_3$-$C_{40}$)olefin. Preferred homopolymers are polyethylene. Preferred interpolymers are those prepared by co-polymerizing a mixture of two or more polymerizable olefins such as, for example, ethylene/propylene, ethylene/1-butene, ethylene/1-pentene, ethylene/1-hexene, ethylene/4-methyl-1-pentene, ethylene/1-octene, ethylene/styrene, ethylene/propylene/butadiene and other EPDM terpolymers. Preferably, the polyolefin copolymer is an ethylene/alpha-olefin interpolymer (i.e., poly(ethylene alpha-olefin) copolymer such as, for example, a poly(ethylene-co-1-octene), which also can be written as poly(ethylene 1-octene) or ethylene/1-octene copolymer; or an ethylene/alpha-olefin/diene interpolymer (i.e., a poly(ethylene alpha-olefin diene) terpolymer such as, for example, a poly(ethylene 1-octene 1,3-butadiene).

The invention olefin polymerization reactions can be run in one reactor or multiple reactors, the multiple reactors being two reactors, or more than two reactors. For example, single reactor, multiple catalyst processes are useful in the present invention. In one embodiment, two or more catalysts are introduced into a single reactor under the olefin polymerization conditions, wherein at least the first one of the catalysts is an invention catalyst and each catalyst inherently produces a mixture or blend of different polyolefin copolymers. The terms "mixture" and "blend" as applied to the polyolefin copolymers are synonymous. In one embodiment, a relatively high molecular weight product ($M_w$ from 100,000 to over 1,000,000, more preferably 200,000 to 500,000) polyolefin is formed from one of the catalysts while a product of a relatively low molecular weight ($M_w$ 2,000 to 300,000) polyolefin is formed from another of the catalysts. The two or more catalysts can have similar or different comonomer incorporation ability, different molecular weight capability, or a combination thereof. The resulting mixture or blend of different polyolefin copolymers will have properties dependent on the ratio of the two or more catalysts that are employed in the single reactor. Suitable combinations of polyolefin molecular weight, comonomer incorporation ability, processes, and ratios of catalysts for such products are disclosed in U.S. Pat. No. 6,924,342. The invention catalysts are compatible with other olefin polymerization catalysts, including Ziegler/Natta catalysts. Due to this compatibility, the second catalyst composition may comprise another invention catalyst, a metallocene or other π-bonded ligand group containing metal complex (including constrained geometry metal complexes), or a polyvalent heteroatom ligand group containing metal complex, especially polyvalent pyridylamine or imidizolylamine based complexes and tetradentate oxygen-ligated biphenylphenol based Group 4 metal complexes. Preferably, the invention catalyst is prepared from and the invention process employs three or fewer, more preferably two, and still more preferably one metal-ligand complex of formula (I).

Examples of suitable processes and systems employing multiple reactors include such processes and systems as are disclosed in U.S. Pat. No. 3,914,342. The multiple reactors, preferably two reactors, can be operated in series or in parallel, with at least one invention catalyst being employed in at least one of the reactors. In some embodiments one, two, or, when employing more than two reactors, three or more of the multiple reactors contain the two or more catalysts described in the immediately preceding paragraph (single reactor paragraph). Polyolefin products from these reactors can have similar or different densities. The final polymer product is a mixture or blend of effluents of different polyolefin copolymers from the two or more, preferably two, reactors. The effluents of different polyolefin copolymers are combined by mixing or blending prior to being subjected to devolatilization so as to result in a uniform mixing or blending of the different polyolefin copolymers. In another embodiment, the molecular weight of the different polyolefin copolymers from the two or more reactors is nearly the same but the densities vary to the extent that one of the reactors produces a first polyolefin copolymer with density in the range of 0.865-0.895, while another reactor produces a second polyolefin copolymer with a different density in the range of 0.885-0.950. When two reactors and two catalysts, at least one of which is an invention catalyst, are employed, such a dual reactor/dual catalyst invention process allows for the preparation of a mixture or blend polyolefin copolymers with tailored properties. In some embodiments employing the dual reactors, two reactors are connected in series, that is, the effluent from a first reactor is charged to a second reactor and, optionally, fresh monomer, solvent and hydrogen is added to the second reactor. Olefin polymerization conditions are adjusted in the second reactor so that they are different from the olefin polymerization conditions that were employed in the first reactor such that a weight ratio of weight of the polyolefin copolymer produced in the first reactor to weight of the polyolefin copolymer produced in the second reactor is ideally in the range of from 20:80 to 80:20. This embodiment of a dual reactor process is capable of producing a mixture or blend of different polyolefin copolymers having broadened molecular weight distribution or polydispersity index (PDI). In addition, in a more preferred embodiment, the invention process produces a mixture or blend of different polyolefin copolymers that comprises high and low molecular weight polyolefin copolymer components, wherein the high molecular weight polyolefin copolymer component contains higher quantities of comonomer (lower density) incorporated therein than quantities of comonomer that are contained in the low molecular weight polyolefin copolymer component.

In some embodiments one of the two reactors of the dual reactor embodiment, including the first of two reactors operating in series, contains a heterogeneous Ziegler-Natta catalyst or a chromium containing catalyst, such as one of the numerous such catalysts known in the art. Examples of Ziegler-Natta catalysts include, but are not limited to, titanium-based catalysts supported on $MgCl_2$, and additionally comprise compounds of aluminum containing at least one aluminum-alkyl bond. Suitable Ziegler-Natta catalysts and their preparation include, but are not limited to, those disclosed in U.S. Pat. Nos. 4,612,300, 4,330,646, and 5,869,575. Suitable chromium based catalysts are those disclosed in U.S. Pat. Nos. 4,981,927, 4,835,219, 4,564,660, 4,173,548, 3,953,413, and elsewhere. The invention catalyst is contained in the same or different one of the two reactors.

The mixture or blend of different polyolefin copolymers and invention process for preparing same are preferred. Especially preferred is such a mixture or blend containing the rich polyethylene or rich polyethylene segment-containing poly(ethylene alpha-olefin) copolymer produced by the invention process.

In another embodiment the present invention is the poly(ethylene alpha-olefin) copolymer prepared by certain embodiments of the invention process. A particularly valuable type of poly(ethylene alpha-olefin) copolymer is the aforementioned poly(ethylene alpha-olefin) block copolymer or, simply, an olefin block copolymer (OBC), which can be prepared by the aforementioned chain shuttling embodiments of the invention process. OBCs are characterized as having at least one so-called "hard segment" or block comprising residuals of ethylene monomer and at least one so-called "soft segment" or block comprising residuals of an alpha-olefin (also known as an alpha-olefin and 1-olefin) monomer. OBCs are available from The Dow Chemical Company, Midland, Mich., USA under the trade name INFUSE™ Olefin Block Copolymers. INFUSE™ Olefin Block Copolymers are useful in a variety of forms and applications such as, for example, those listed at www.dow.com/infuse. Part of a preparation of an OBC involves a process that, among other steps, selectively polymerizes ethylene in the presence of the alpha-olefin to form the at least one hard segment of the OBC. More preferably, the poly(ethylene alpha-olefin) block copolymer is characterizable as having a melting temperature of greater than 100° C., and more preferably greater than 120° C., as determined by Differential Scanning Calorimetry using the procedure described later.

In some embodiments a preferred invention process can achieve a minimum molecular weight distribution or polydispersity index (PDI) of the polyolefin copolymer product produced thereby. In some embodiments the PDI is greater than 2.0, more preferably greater than, or equal to, 2.2; still more preferably greater than 2.30, even more preferably greater than 2.40, and yet more preferably greater than 2.50. In some embodiments, PDI is 2.6, in other embodiments 2.7. More preferably the PDI is as defined as in any one of the Examples described later in the EXAMPLES OF THE PRESENT INVENTION section.

In some embodiments a preferred invention process can achieve a productivity ratio of weight of polyolefin copolymer produced per weight of ethylene employed, as determined employing ethylene and 1-octene as described later at a polymerization reaction temperature of 190° C., wherein the productivity ratio of the polyolefin copolymer produced to ethylene employed is greater than 1.2, preferably greater than 1.40, and more preferably greater than 1.60, and still more preferably greater than 1.80. More preferably the productivity ratio is as defined as in any one of the Examples described later in the EXAMPLES OF THE PRESENT INVENTION section.

Illustrative examples of the present invention are provided later where the examples employ certain methods and materials, which include certain preparations. The methods and materials and preparations are described in the following section.

Methods, Materials and Preparations

General Considerations

All solvents and reagents are obtained from commercial sources and used as received unless indicated otherwise. Purify hexanes solvent through a column of activated alumina followed by a column of Q5 copper oxide on alumina (Cu-0226 S is obtained from (Engelhard subsidiary of BASF Corporation). Purify tetrahydrofuran (THF) and diethyl ether through columns of activated alumina. Synthesize and store all metal complexes in a Vacuum Atmospheres inert atmosphere glove box under a dry nitrogen atmosphere. Record NMR spectra on a 300 megahertz (MHz) Varian INOVA spectrometer. Report chemical shifts in parts per million (δ) versus tetramethylsilane and referenced to residual protons in a deuterated solvent.

Determining percent incorporation of 1-octene and polymer density by FT-IR Spectroscopy:

Deposit 140 microliters (µL) of each polymer solution onto a silica wafer, heat at 140° C. until the 1,2,4-trichlorobenzne (TCB) evaporates, and analyze using a Nicolet Nexus 670 FT-IR with 7.1 version software equipped with an AutoPro auto sampler.

Gel Permeation Chromatography (GPC):

Determine weight average molecular weight ($M_w$) and polydispersity index: Determine $M_w$ and ratio of $M_w/M_n$ (polydispersity index or PDI) using a Polymer Labs™ 210 high temperature gel permeation chromatograph. Prepare samples using 13 mg of polyethylene polymer that is diluted with 16 mL of 1,2,4-trichlorobenzene (stabilized with butylated hydroxy toluene (BHT)), heat and shake at 160° C. for 2 hours.

Determining melting and crystallization temperatures and heat of fusion by Differential Scanning Calorimetry (DSC; DSC 2910, TA Instruments, Inc.)): First heat samples from room temperature to 180° C. at a heating rate of 10° C. per minute. After being held at this temperature for 2 to 4 minutes, cool the samples to −40° C. at a cooling rate of 10° C. per minute; hold the sample at the cold temperature for 2 to 4 minutes, and then heat the sample to 160° C.

Analyzing end groups by proton-nuclear magnetic resonance ($^1$H-NMR) spectroscopy using a Varian 600 MHz NMR instrument and deuterated tetrachloroethane.

Abbreviations (meanings): r.t. (room temperature); g (gram(s)); mL (milliliter(s)); ° C. (degrees Celsius); mmol (millimole(s)); MHz (MegaHertz); Hz (Hertz).

Non-limiting examples of intermediates of the present invention and methods of preparing same are described in the Preparations.

Preparation 1

Preparation of Intermediate, 3,6-bis(1,1-dimethylethyl)-9H-carbazole, (P1)

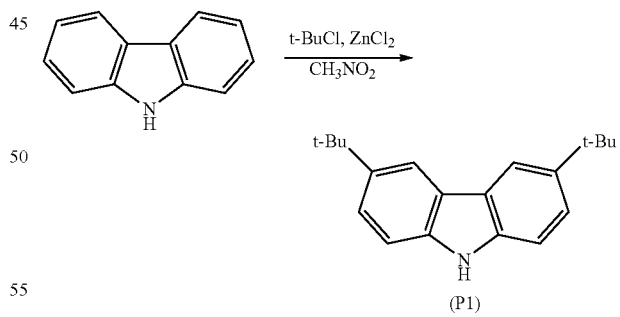

To a 500 mL three-necked round bottom flask equipped with an over head stirrer, nitrogen gas bubbler, and an addition funnel add 20.02 g (120.8 mmol) of carbazole, 49.82 g (365.5 mmol) of $ZnCl_2$, and 300 mL of nitromethane at room temperature. To the resulting dark brown slurry add 49.82 g (365.5 mmol) of 2-chloro-2-methylpropane (also known as tertiary-butyl chloride or t-BuCl) dropwise from the addition funnel over the period of 2.5 hours. After completing the addition, stir the resulting slurry for an additional 18 hours. Pour the reaction mixture into 800 mL of ice cold water, extract with 3×500 mL methylene chloride, combine and dry the extracts with anhydrous magnesium sulfate, filter, and concentrate the filtrate first by rotary evaporation and then by evaporation under high vacuum to remove nitromethane. Dissolve the resulting residue first in hot methylene chloride (70 mL) followed by hot hexanes (50 mL), allow the resulting solution to cool to room temperature and then placed it in a refrigerator overnight. Isolate the solids formed and wash the isolated solids with cold hexanes and then place them under high vacuum to yield 10.80 g (32.0%) of (P1) as off white crystals.

$^1$H NMR (400 MHz, CDCl$_3$) δ 8.11 (d, J=1.6 Hz, 2H), 7.75 (s, 1H), 7.48 (dd, J=8.5, 1.9 Hz, 2H), 7.31 (d, J=8.5 Hz, 2H), 1.48 (s, 18H).

$^{13}$C NMR (101 MHz, CDCl$_3$) δ 142.17 (s), 137.96 (s), 123.45 (s), 123.28 (s), 116.11 (s), 109.97 (s), 34.73 (s), 32.09 (s).

Preparation 2

Preparation of Intermediate, 2-iodo-4-(2,4,4-trimethylpentan-2-yl)phenol, (P2)

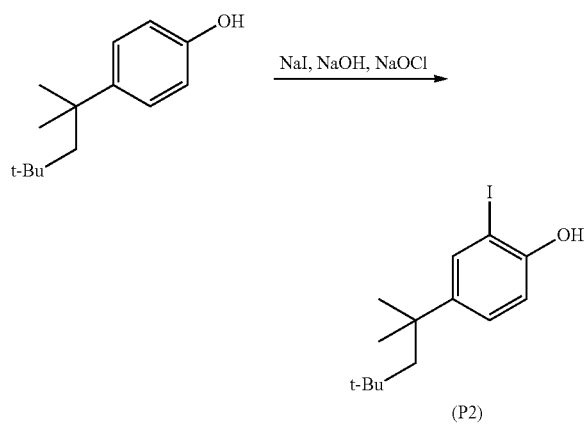

To a stirred solution of 10.30 g (50.00 mmol) of 4-(2,4,4-trimethylpentan-2-yl)phenol in 125 mL of methanol at 0° C., add 7.48 g (50.00 mmol) of NaI and 2.00 g (50 mmol) of NaOH. To the resulting mixture add 86 mL of 5% aqueous NaOCl solution (commercial bleach) over a one hour period. Stir the resulting slurry for one more hour at 0° C. Then add 30 mL of aqueous 10% Na$_2$S$_2$O$_3$ solution, and acidify the resulting reaction mixture with addition of dilute hydrochloric acid. Extract the resulting mixture with methylene chloride, wash the resulting organic layer with brine, and dry it over anhydrous magnesium sulfate. Remove volatiles and purify the resulting residue by flash chromatography on silica gel eluting with 5 volume percent (vol %) ethyl acetate in hexanes to yield 11.00 g (66%) of (P2) as a viscous oil.

$^1$H NMR (CDCl$_3$) δ 7.60 (d, J=2.5 Hz, 1H), 7.25 (dd, J=8.5 and 2.2 Hz, 1H), 6.90 (d, J=8.5 Hz, 1H), 5.13 (s, 1H), 1.69 (s, 2H), 1.32 (s, 6H) and 0.74 (s, 9H).

$^{13}$C{$^1$H} NMR (CDCl$_3$) δ 152.21, 144.52, 135.56, 128.03, 114.17, 85.36, 56.92, 38.01, 32.43, 31.90 and 31.64.

GCMS (m/e): 332 (M$^+$).

Preparation 3

Preparation of Intermediate, 2-iodo-1-(methoxymethoxy)-4-(2,4,4-trimethylpentan-2-yl)benzene, (P3)

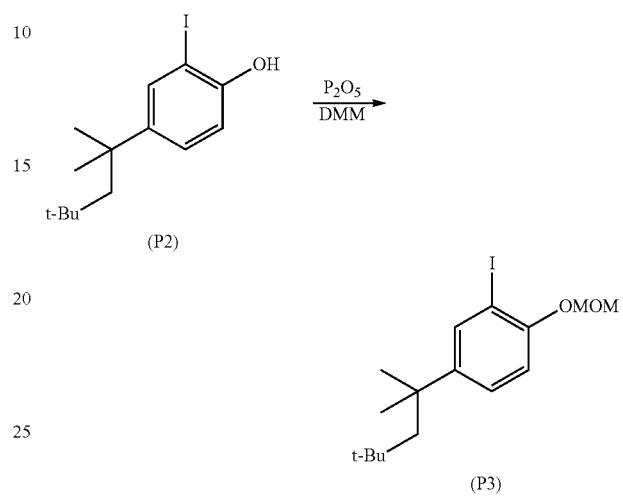

(A general procedure for methoxymethyl-ether (MOM-ether synthesis.) To a stirred solution of 4-(2,4,4-trimethylpentan-2-yl)phenol (P2) (9.50 g, 28.61 mmol, Preparation 2) and dimethoxymethane (25 mL, 286.2 mmol; DMM) in 150 mL of methylene chloride under the nitrogen atmosphere, add 14.00 g (99.29 mmol) of P$_2$O$_5$ in portions over a period of 1.5 hours. After the final addition, stir the resulting reaction mixture for another 1.5 hours. Then decant the resulting solution, and pass the decanted liquid through a small bed of silica gel. Wash the resulting solution successively with water and brine, and dry the washed solution over anhydrous magnesium sulfate. Pass the dried solution through a small bed of silica gel, and remove solvent to yield 9.90 g (92%) of pure (P3) as a viscous oil.

$^1$H NMR (C$_6$D$_6$) δ 7.88 (d, J=2.2 Hz, 1H), 7.03 (dd, J=2.5 Hz and 8.5 Hz, 1H), 6.89 (d, J=8.8 Hz, 1H), 4.82 (s, 2H), 3.12 (s, 3H), 1.53 (s, 2H), 1.15 (s, 6H) and 0.70 (s, 9H).

$^{13}$C{$^1$H} NMR (C$_6$D$_6$) δ 154.47, 145.69, 137.49, 127.40, 114.45, 95.12, 87.32, 56.98, 56.03, 38.11, 32.55.

Preparation 4

Preparation of Intermediate, 3,6-di-tert-butyl-9-(2-(methoxymethoxy)-5-(2,4,4-trimethylpentan-2-yl)phenyl)-9H-carbazole, (P4)

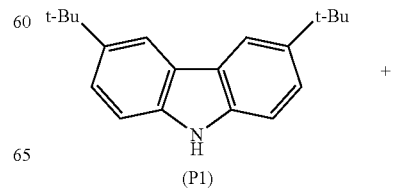

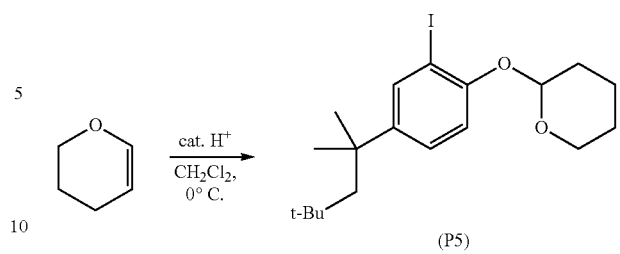

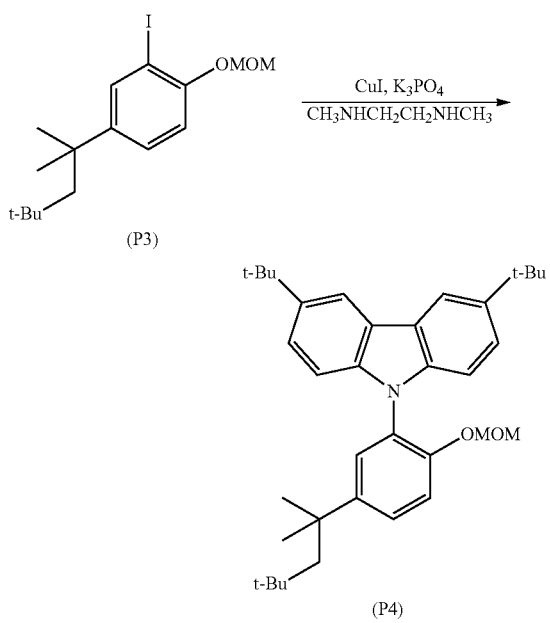

Heat a mixture of 4.96 g (13.18 mmol) of 2-iodo-1-(methoxymethoxy)-4-(2,4,4-trimethylpentan-2-yl)benzene (P3), Preparation 3; 3.68 g (13.18 mmol) of 3,5-di-t-butylcarbazole (P1), Preparation 1; 0.53 g (2.6 mmol) of CuI, 8.42 g (39.54 mmol) of $K_3PO_4$, and 0.63 g (4.13 mmol) of N,N'-dimethylethylenediamine in 25 mL of toluene under nitrogen atmosphere to reflux and reflux for 24 hours. Cool the reaction mixture, dilute it with 25 mL of THF, and filter to remove solid. Concentrate the filtrate to give a solid residue. Crystallize the solid residue from acetonitrile to yield 5.5 g (90%) of (P4) as white solid.

$^1$H NMR (CDCl$_3$) δ 8.17 (d, J=2.4 Hz, 2H), 7.46 (m, 4H), 7.33 (d, J=7.8 Hz, 1H), 7.09 (d, J=8.6 Hz, 2H), 4.94 (s, 2H), 3.21 (s, 3H), 1.76 (s, 2H), 1.50 (s, 18H), 1.40 (s, 6H) and 0.83 (s, 9H).

$^{13}$C{$^1$H} NMR (CDCl$_3$) δ 151.37, 144.89, 142.16, 139.87, 127.85, 126.81, 126.63, 123.34, 122.99, 116.34, 116.03, 109.45, 95.13, 57.00, 56.07, 38.25, 34.70, 32.40, 32.07, 31.84, 31.57.

Preparation 5

Preparation of Intermediate, 2-(2-iodo-4-(2,4,4-trimethylpentan-2-yl)phenoxy)tetrahydro-2H-pyran, (P5)

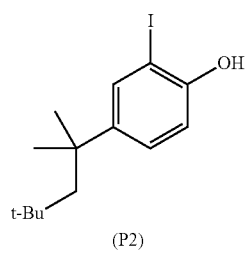

To a stirred solution of 4.91 g (14.78 mmol) of 4-(2,4,4-trimethylpentan-2-yl)phenol (P2) and 1.50 g (17.83 mmol) of 3,4-dihydropyran in 5 mL of methylene chloride at 0° C. add 0.039 g (0.205 mmol) of para-toluenesulfonic acid monohydrate. The resulting solution quickly becomes purple. Allow solution to warm to room temperature, and stir thereat for approximately 10 minutes. Then add 0.018 g (0.178 mmol) of triethylamine, and the resulting mixture turned yellow. Dilute the mixture with 50 mL of methylene chloride, and successively wash the diluted mixture with 50 mL each of 1M NaOH, water, and brine. Dry the organic phase with anhydrous magnesium sulfate, filter, and concentrate to give a crude material. Purify the crude material by flash chromatography on silica gel using 5 vol % ethyl acetate in hexanes to yield 5.18 g (93.12%) of (P5) as a golden oil.

$^1$H NMR (CDCl$_3$) δ 7.74 (d, J=2.3 Hz, 1H), 7.27 (dd, J=2.3 and 8.6 Hz, 1H), 6.99 (d, J=8.6 Hz, 1H), 5.49 (m, 1H), 3.91 (m, 1H), 3.61 (m, 1H), 2.20-1.60 (m, 6H), 1.69 (s, 2H), 1.34 (s, 6H) and 0.75 (s, 9H).

$^{13}$C{$^1$H} NMR (CDCl$_3$) δ 153.27, 145.49, 136.98, 127.08, 114.44, 96.72, 87.09, 61.69, 56.91, 37.95, 32.33, 31.81, 31.52, 31.44, 30.26, 25.27, 18.36.

Preparation 6

Preparation of Intermediate, 3,6-di-tert-butyl-9-(2-(tetrahydro-2H-pyran-2-yloxy)-5-(2,4,4-trimethylpentan-2-yl)phenyl)-9H-carbazole, (P6)

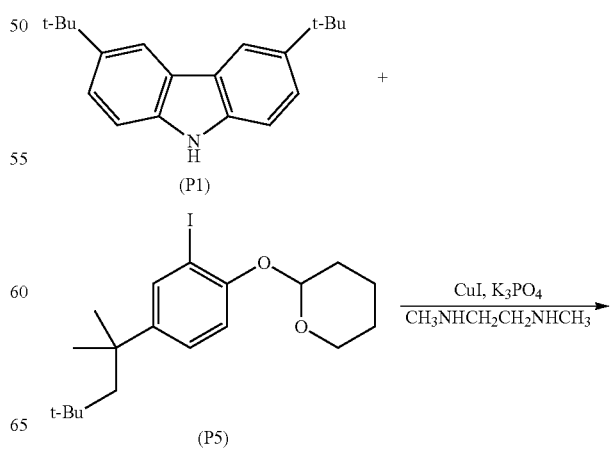

-continued

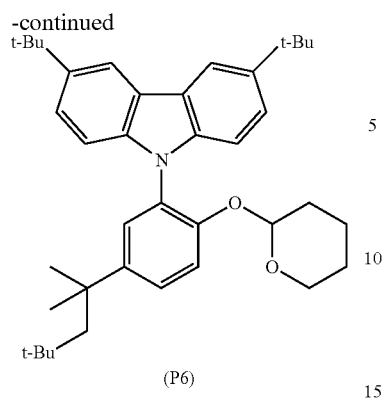

To a 50 mL three necked round bottom flask equipped with a stir bar and condenser under N₂ atmosphere add 20 mL of dry toluene, 5.00 g (12.01 mmol) of 2-(2-iodo-4-(2,4,4-trimethylpentan-2-yl)phenoxy)tetrahydro-2H-pyran (P5), Preparation 5; 3.56 g (12.01 mmol) of di-t-butyl carbazole (P1), Preparation 1; 0.488 g (2.56 mmol) of CuI, 7.71 g (36.22 mmol) of K₃PO₄, and 0.338 g (3.84 mmol) of N,N'-dimethylethylenediamine. Reflux the reaction mixture for 48 hours, cool it, filter it through a bed of silica gel, rinse the silica gel with tetrahydrofuran (THF), and concentrate the organics to give a crude residue. Crystallize the crude residue using acetonitrile to yield 4.57 g (67.01%) of (P6) as a white solid.

$^1$H NMR (CDCl₃) δ 8.13 (t, J=1.71 Hz, 1H), 7.48 (d, J=2.4 Hz, 1H), 7.40 (m, 3H), 7.31 (d, J=8.68 Hz, 1H), 7.14 (d, J=8.68 Hz, 1H), 7.08 (d, J=8.56 Hz, 1H), 5.22 (t, J=2.81 Hz, 1H), 3.72 (td, J=11.12 and 2.8 Hz, 1H), 3.47 (dt, J=11.12 and 3.47 Hz, 1H), 1.75 (s, 2H), 1.474 (s, 9H), 1.472 (s, 9H), 1.394 (s, 3H), 1.391 (s, 3H), 1.37-1.12 (m, 6H) and 0.82 (s, 9H).

$^{13}$C{$^1$H} NMR (CDCl₃) δ 150.96, 144.22, 142.07, 140.02, 127.49, 126.60, 126.56, 123.14, 123.12, 122.96, 116.37, 115.88, 115.72, 110.18, 109.52, 97.02, 61.56, 57.03, 38.23, 34.69, 32.41, 32.07, 31.86, 31.72, 31.50, 29.98, 25.06, 17.61.

Preparation 7

Preparation of Intermediate, 4-fluoro-2-iodophenol, (P7)

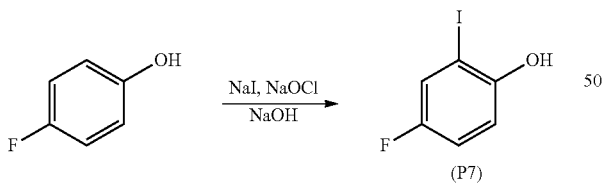

To a stirred solution of 16.8 g (150 millimoles (mmol)) of 4-fluorophenol in 300 mL of methanol at 0° C., add 22.5 g (150 mmol) of NaI and 6.00 g (150 mmol) of NaOH. To the resulting mixture add 258 mL of 5% aqueous NaOCl solution (commercial bleach) over a one hour period. Stir the resulting slurry for one more hour at 0° C. Add 90 mL of 10% aqueous Na₂S₂O₃ solution, and acidify the resulting reaction mixture by adding dilute hydrochloric acid. Extract the resulting mixture with methylene chloride, wash the resulting organic layer with brine and dry it over anhydrous magnesium sulfate. Remove solvent, dissolve the residue in hot hexanes, and allow the resulting solution to stand in a freezer for two hours. A dark colored material oils out. Decant the solution away therefrom and allow the resulting colorless decanted solution to stand in a freezer for 18 hours. Filter off the resulting white crystals and dry them under reduced pressure to yield 18.00 g (50%) of pure 4-fluoro-2-iodophenol (P7) as a white solid.

$^1$H NMR (CDCl₃) δ 7.30 (m, 1H), 6.95 (m, 2H) and 5.13 (s, 1H).

GCMS (m/e): 238 (Me).

Preparation 8

Preparation of Intermediate, 1,3-bis(4-fluoro-2-iodophenoxy)propane, (P8)

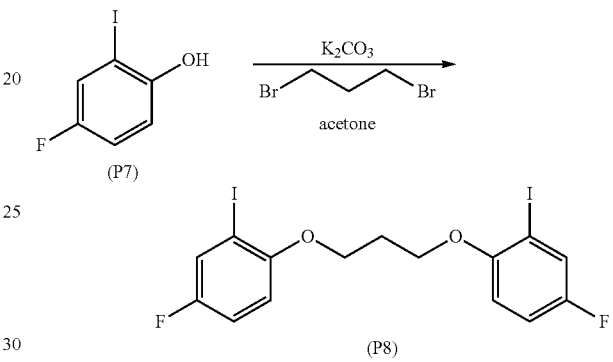

To a solution of 15.00 g (63.03 mmol) of 4-fluoro-2-iodophenol (P7), Preparation 7 and 6.40 g (31.68 mmol) of 1,3-dibromopropane in 200 mL of acetone add 26.00 g (188.4 mmol) of potassium carbonate. Reflux the resulting reaction mixture for 24 hours. Cool the reaction mixture to room temperature, filter it, and concentrate the filtrate by rotary evaporation. Crystallize the resulting solid from acetonitrile to yield 12.00 g (74%) of (P8) as a white crystalline solid.

$^1$H NMR (CDCl₃) δ 7.48 (m, 1H), 7.02 (m, 1H), 6.88 (m, 1H), 4.26 (t, J=6.05 Hz, 4H) and 2.34 (quintet, J=6.05 Hz, 2H).

GCMS (m/e): 516 (Me).

Preparation 9

Preparation of Intermediate, 4-chloro-2-iodophenol, (P9)

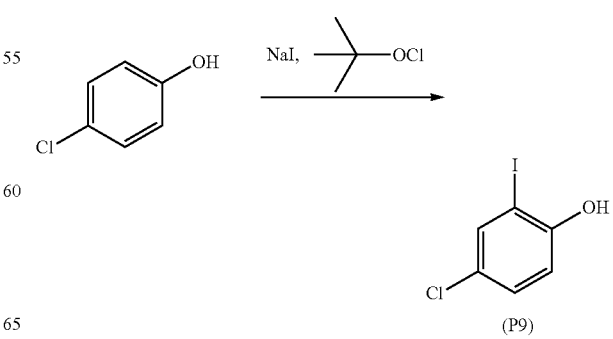

To a solution of 40 mmol of 4-chlorophenol and 52 mmol of sodium iodide in 80 mL of acetonitrile and 16 mL of water at room temperature add 52 mmol of tert-butyl hypochlorite dropwise over a period of 30 minutes. Stir the reaction mixture for 3 hours at ambient temperature. Dilute the reaction mixture with 200 mL of ethyl acetate. Wash the resulting organic solution successively with 5% aqueous sodium thiosulfate solution and brine and dry over anhydrous magnesium sulfate. Remove the solvent and then crystallize from hexanes to yield 51% of (P9) as a solid.

Preparation 10

Preparation of Intermediate, 1,3-bis(4-chloro-2-iodophenoxy)propane, (P10)

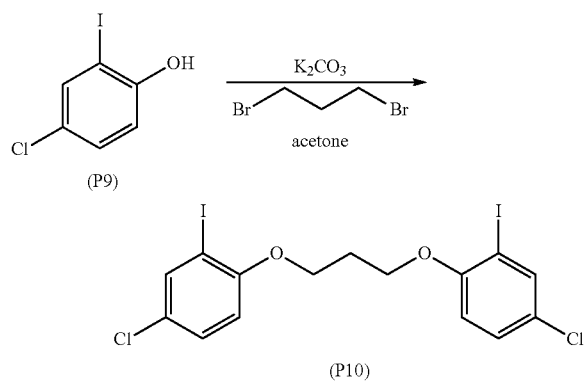

In a manner similar to the preparation of (P8) (Preparation 8) except use (P9) (Preparation 9) instead of (P7), prepare crude 1,3-bis(4-chloro-2-iodophenoxy)propane (P10) from 4-chloro-2-iodophenol (P9) and purify by crystallization from acetonitrile to yield (P10) as a white solid.

Preparation 11

Preparation of Intermediate, 2-iodo-4-methylphenol, (P11)

In a manner similar to the preparation of (P7) (Preparation 7), except use 4-methylphenol instead of the 4-(2,4,4-trimethylpentan-2-yl)phenol, prepare crude (P11). Purify crude (P11) by crystallization from hexanes to obtain purified (P11) as a solid.

Preparation 12

Preparation of Intermediate, 1,3-bis(2-iodo-4-methylphenoxy)propane, (P14)

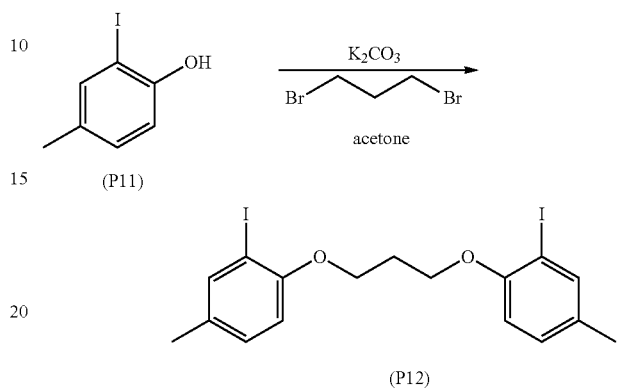

In a manner similar to the preparation of (P8) (Preparation 8) except use (P11) (Preparation 11) instead of (P7), prepare crude 1,3-bis(2-iodo-4-methylphenoxy)propane, (P12) from 2-iodo-4-methylphenol (P11) and purify by crystallization from acetonitrile to yield purified (P12) as a solid.

Preparation 13

Preparation of Intermediate, 1-(4-chloro-2-iodophenoxy)-3-(4-fluoro-2-iodophenoxy)propane, (P13)

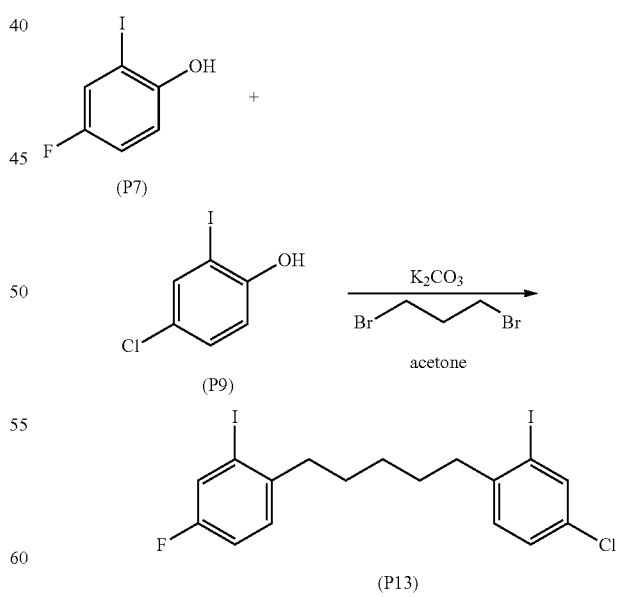

In a manner similar to the preparation of (P8) (Preparation 8) except use a mixture of equimilar amounts of (P7) (Preparation 7) and (P9) (Preparation 9) instead of (P7), prepare crude 1-(4-chloro-2-iodophenoxy)-3-(4-fluoro-2-iodophenoxy)propane, (P13), and purify it by crystallization from acetonitrile to yield (P13) as a white solid.

Non-limiting examples of the present invention are described below that illustrate some specific embodiments and aforementioned advantages of the present invention. Preferred embodiments of the present invention incorporate one limitation, and more preferably any two, limitations of the Examples, which limitations thereby serve as a basis for amending claims.

EXAMPLES OF THE PRESENT INVENTION

Example Q1

Preparation of Ligand, 2',2'''-(propane-1,3-diylbis (oxy))bis(3-(3,6-di-tert-butyl-9H-carbazol-9-yl)-5'-fluoro-5-(2,4,4-trimethylpentan-2-yl)biphenyl-2-ol, (Q1)

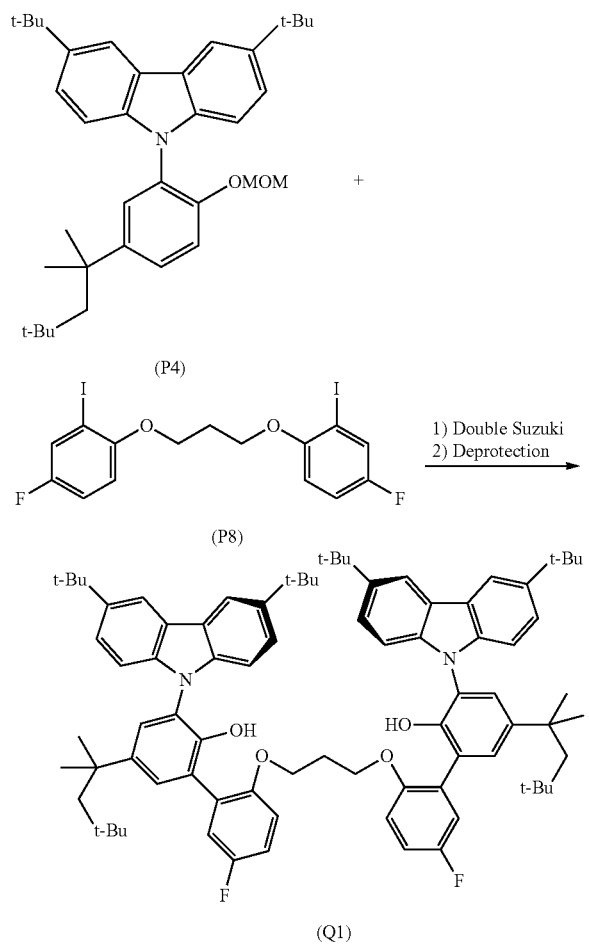

(General Procedure for Double Suzuki Reaction and Deprotection Reaction). To a stirred solution of 3.5 g (6.64 mmol) of 3,6-di-tert-butyl-9-(2-(methoxymethoxy)-5-(2,4,4-trimethylpentan-2-yl)phenyl)-9H-carbazole (P4), Preparation 3 in 40 mL of tetrahydrofuran at 0° C. under nitrogen atmosphere add 3.50 mL (8.75 mmol) of n-butyl lithium (2.5 M solution in hexanes) over a period of 10 minutes. Stir the resulting solution at 0° C. for three more hours. Add triisopropyl borate (2.0 mL, 8.67 mmol) and continue stirring at 0° C. for 1 hour. Slowly warm the mixture to room temperature, and stir for 3 more hours at room temperature. Concentrate the warmed reaction mixture to dryness by rotary evaporation, and add 100 mL of ice cold water. Acidify the resulting mixture using 2 Normal (N) aqueous hydrochloric acid, and extract with methylene chloride. Remove the solvent (methylene chloride) by rotary evaporation, and dissolve the residue in 45 mL of dimethoxyethane. Treat this solution with a solution of 0.80 g of NaOH in 16 mL of water, 16 mL of tetrahydrofuran and 1.70 g (3.29 mmol) of 1,3-bis(4-fluoro-2-iodophenoxy)propane (P8), Preparation 8. Purge the resulting system with nitrogen gas, and add 0.15 g (0.13 mmol) of Pd(PPh$_3$)$_4$ (Ph is phenyl). Heat the resulting mixture to 85° C. for 36 hours under nitrogen gas atmosphere. Cool the reaction mixture, and remove volatiles by rotary evaporation. Treat the resulting residue with 100 mL of water, and extract with methylene chloride. Wash the methylene chloride solution with water and brine, and dry over anhydrous magnesium sulfate. Pass the resulting dried solution through a small bed of silica gel, and concentrate by rotary evaporation. Dissolve the resulting residue in 25 mL of tetrahydrofuran, and treat the THF solution with 150 mL of methanol and 0.40 mL of concentrated hydrochloric acid. Reflux the resulting solution for 10 hours. Cool the solution and pass it through a small bed of silica gel, and wash with methanol. Keep the resulting solution in a fume hood and allow slow evaporation of the solvent to give a precipitated solid. Filter the precipitate and dry it under reduced pressure to yield 2.59 g (64%) of (Q1) as a cream colored solid.

$^1$H NMR (500 MHz, C$_6$D$_6$) δ 8.47 (d, J=1.9 Hz, 4H), 7.50 (dd, J=8.6, 1.9 Hz, 4H), 7.41 (d, J=2.4 Hz, 2H), 7.30 (d, J=2.4 Hz, 2H), 7.28 (d, J=8.6 Hz, 4H), 7.03 (dd, J=8.6, 3.2 Hz, 2H), 6.58 (ddd, J=8.9, 8.0, 3.2 Hz, 2H), 5.93 (dd, J=9.1, 4.4 Hz, 2H), 5.38 (s, 2H), 3.63 (t, J=5.5 Hz, 4H), 1.58 (p, J=5.7 Hz, 2H), 1.50 (s, 4H), 1.44 (s, 36H), 1.16 (s, 12H), 0.76 (s, 18H).

$^{13}$C{$^1$H} NMR (126 MHz, C$_6$D$_6$) δ 157.59 (d, J=239.8 Hz), 151.79 (d, J=1.8 Hz), 148.69 (s, J=3.3 Hz), 143.23 (s), 142.99 (s), 140.75 (s), 129.55 (s), 128.56 (d, J=7.6 Hz), 128.29 (s), 127.71-127.58 (m), 126.74 (d, J=0.8 Hz), 125.00 (s), 124.27 (s), 124.14 (s), 118.51 (d, J=23.2 Hz), 116.87-116.68 (m), 115.63 (d, J=22.8 Hz), 113.45-113.20 (m), 110.11-109.94 (m), 65.00 (s), 57.10 (s), 38.21 (d, J=7.9 Hz), 34.86 (s), 32.44 (s), 32.18 (s), 31.97 (s), 31.55 (s), 28.89 (s).

$^{19}$F NMR (282 MHz, CDCl$_3$) d −122.22 (s).

ES-HRMS: m/e calcd for (M+H, C$_{83}$H$_{101}$N$_2$F$_4$O$_4$) 1227.7729. found 1227.7729.

Example Q2

Preparation of Ligand, 2',2'''-(propane-1,3-diylbis (oxy))bis(3-(3,6-di-tert-butyl-9H-carbazol-9-yl)-5'-chloro-5-(2,4,4-trimethylpentan-2-yl)biphenyl-2-ol, (Q2)

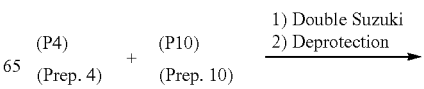

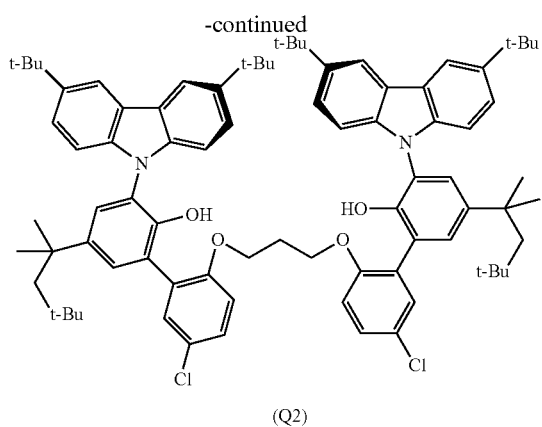

(Q2)

In a manner similar to the preparation of (Q1) (Example Q1) except use (P10) (Preparation 10) instead of (P8), prepare crude (Q2). Purify crude (Q2) by flash chromatography on silica gel using 3% tetrahydrofuran in hexanes to afford (Q2) as a solid.

$^1$H-NMR (CDCl$_3$) δ 8.30 (d, J=1.65 Hz, 4H), 7.43 (dd, J=1.8 and 8.52 Hz, 4H), 7.34 (d, J=2.3 Hz, 2H), 7.19 (d, J=2.3 Hz, 2H), 7.13 (d, J=2.75 Hz, 2H), 7.01 (d, J=8.52 Hz, 4H), 6.60 (dd, J=2.6 and 8.79 Hz, 2H), 5.75 (d, J=8.79 Hz, 2H), 4.95 (s, 2H), 5.22 (t, J=5.22 Hz, 4H), 1.93 (quintet, J=5.22 Hz, 2H), 1.68 (s, 4H), 1.48 (s, 36H), 1.34 (s, 12H) and 0.78 (s, 18H);
$^{13}$C-NMR (CDCl$_3$) δ 155.95, 147.78, 142.93, 142.70, 139.83, 130.99, 129.13, 128.87, 128.08, 127.10, 125.71, 123.78, 123.66, 123.43, 116.36, 112.48, 109.21, 64.26, 57.16, 38.17, 34.78, 32.42, 32.09, 31.88, 31.83, 31.54 and 28.83; MS m/e 1276.7388 (M+NH$_4$), Calculated for C$_{83}$H$_{100}$N$_2$Cl$_2$O$_4$+NH$_4$ 1276.7398.

Example Q3

Preparation of Ligand, 2',2"-(propane-1,3-diylbis(oxy))bis(3-(3,6-di-tert-butyl-9H-carbazol-9-yl)-5'-methyl-5-(2,4,4-trimethylpentan-2-yl)biphenyl-2-ol, (Q3)

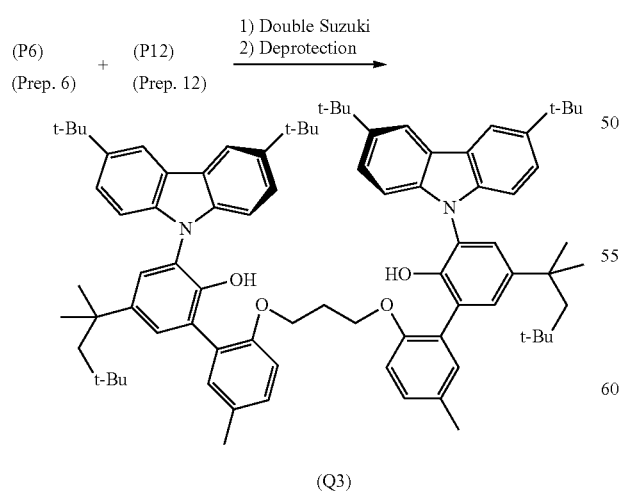

(Q3)

In a manner similar to the preparation of (Q1) (Example Q1) except use 3,6-di-tert-butyl-9-(2-(tetrahydro-2H-pyran-2-yloxy)-5-(2,4,4-trimethylpentan-2-yl)phenyl)-9H-carbazole, (P6) (Preparation 6) instead of (P4) and use 1,3-bis(2-iodo-4-methylphenoxy)propane, (P12) (Preparation 12) instead of (P8) to give crude (Q3). Dissolve the crude (Q3) in 100 mL of THF/MeOH (1:1; "MeOH" is methanol), heat the solution to 50° C., add a catalytic amount of para-toluenesulfonic acid (or concentrated hydrochloric acid), and stir for 5 hours. Remove the solvent and partially purify the remaining residue by flash chromatography on silica gel using 5 vol % ethyl acetate in hexanes to give partially purified material. Purify the partially purified material by crystallization from THF/MeOH to yield (Q3) as a solid.

Example Q4

Preparation of Ligand, 2',2"-(propane-1,3-diylbis(oxy))-1-(3,6-di-tert-butyl-9H-carbazol-9-yl)-5'-fluoro-5-(2,4,4-trimethylpentan-2-yl)biphenyl-2-ol)-3-(3,6-di-tert-butyl-9H-carbazol-9-yl)-5'-chloro-5-(2,4,4-trimethylpentan-2-yl)biphenyl-2-ol), (Q4)

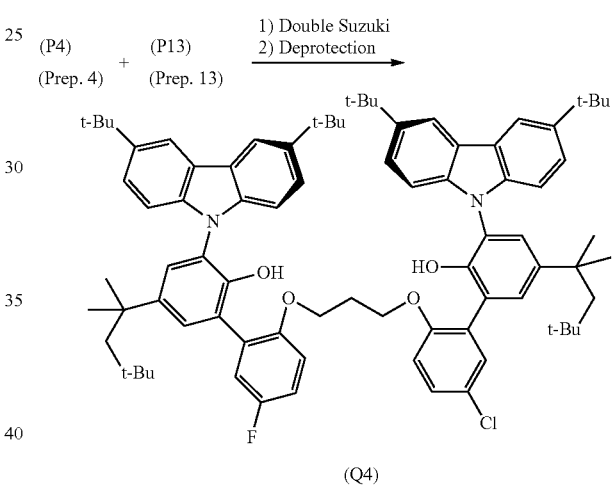

(Q4)

In a manner similar to the preparation of (Q1) (Example Q1) except use (P13) (Preparation 13) instead of (P8), prepare crude (Q4). Purify crude (Q4) by flash chromatography on silica gel using 3% tetrahydrofuran in hexanes to afford (Q4) as a solid.

Examples Q5 to Q20

Preparation of Ligands (Q5) to (Q20)

In a manner similar to the preparation of Examples Q1 to Q4, the metal-ligand complexes (Q5) to (Q20) can be prepared.

(2',2"-(propane-1,3-diylbis(oxy))bis(3-(3,6-di-tert-octyl-9H-carbazol-9-yl)-5'-fluoro-5-(2,4,4-trimethylpentan-2-yl)biphenyl-2-ol) (Q5);

(2',2"-(propane-1,3-diylbis(oxy))bis(3-(3,6-di-tert-butyl-9H-carbazol-9-yl)-5'-ethyl-5-(2,4,4-trimethylpentan-2-yl)biphenyl-2-ol), (Q6);

(2',2"-(propane-1,3-diylbis(oxy))bis(3-(3,6-di-tert-octyl-9H-carbazol-9-yl)-5'-fluoro-5-(tert-butyl)biphenyl-2-ol), (Q7);

(2',2"-(propane-1,3-diylbis(oxy))bis(3-(3,6-diphenyl-9H-carbazol-9-yl)-5',6'-difluoro-5-(2,4,4-trimethylpentan-2-yl)biphenyl-2-ol), (Q8);

(2',2"-(propane-1,3-diylbis(oxy))bis(5'-cyano-3-(3,6-di-tert-butyl-9H-carbazol-9-yl)-5-(2,4,4-trimethylpentan-2-yl)biphenyl-2-ol), (Q9);

(2',2"-(propane-1,3-diylbis(oxy))bis(5'-dimethylamino-3-(3,6-di-tert-butyl-9H-carbazol-9-yl)-5-(2,4,4-trimethylpentan-2-yl)biphenyl-2-ol), (Q10);

(2',2"-(propane-1,3-diylbis(oxy))bis(5'-cyclopropyl-3-(3,6-di-tert-butyl-9H-carbazol-9-yl)-5-(2,4,4-trimethylpentan-2-yl)biphenyl-2-ol), (Q11);

(2',2"-(propane-1,3-diylbis(oxy))bis(5'-fluoro-3-(3,6-di-tert-butyl-9H-carbazol-9-yl)-5-(tert-butyl)biphenyl-2-ol), (Q12);

(2',2"-(propane-1,3-diylbis(oxy))bis(3-(3,6-di-tert-butyl-9H-carbazol-9-yl)-5'-chloro-6-(2,4,4-trimethylpentan-2-yl)biphenyl-2-ol), (Q13);

(2',2"-(propane-1,3-diylbis(oxy))bis(3-(3,6-di-tert-butyl-9H-carbazol-9-yl)-5'-trifluoromethyl-5-(2,4,4-trimethylpentan-2-yl)biphenyl-2-ol), (Q14);

(2',2"-(propane-1,3-diylbis(oxy))bis(3-(3,6-di-tert-butyl-9H-carbazol-9-yl)-5'-(tert-butyl)-5-(2,4,4-trimethylpentan-2-yl)biphenyl-2-ol), (Q15);

(2',2"-(1,3-dimethylpropane-1,3-diylbis(oxy))bis(3-(3,6-di-tert-butyl-9H-carbazol-9-yl)-5'-fluoro-5-(2,4,4-trimethylpentan-2-yl)biphenyl-2-ol), (Q16);

(2',2"-(butane-1,3-diylbis(oxy))bis(3-(3,6-di-tert-butyl-9H-carbazol-9-yl)-5'-fluoro-5-(2,4,4-trimethylpentan-2-yl)biphenyl-2-ol), (Q17);

(2',2"-(cyclopentan-1,3-diylbis(oxy))bis(3-(3,6-di-tert-butyl-9H-carbazol-9-yl)-5'-fluoro-5-(2,4,4-trimethylpentan-2-yl)biphenyl-2-ol), (Q18);

(2',2"-(2,2-dimethyl-2-silapropane-1,3-diylbis(oxy))bis(3-(3,6-di-tert-butyl-9H-carbazol-9-yl)-5'-fluoro-5-(2,4,4-trimethylpentan-2-yl)biphenyl-2-ol), (Q19); and (2',2"-(propane-1,3-diylbis(N-methyl-aza))bis(3-(3,6-di-tert-butyl-9H-carbazol-9-yl)-5'-(tert-butyl)-5-(2,4,4-trimethylpentan-2-yl)biphenyl-2-ol), (Q20).

Figure 5:
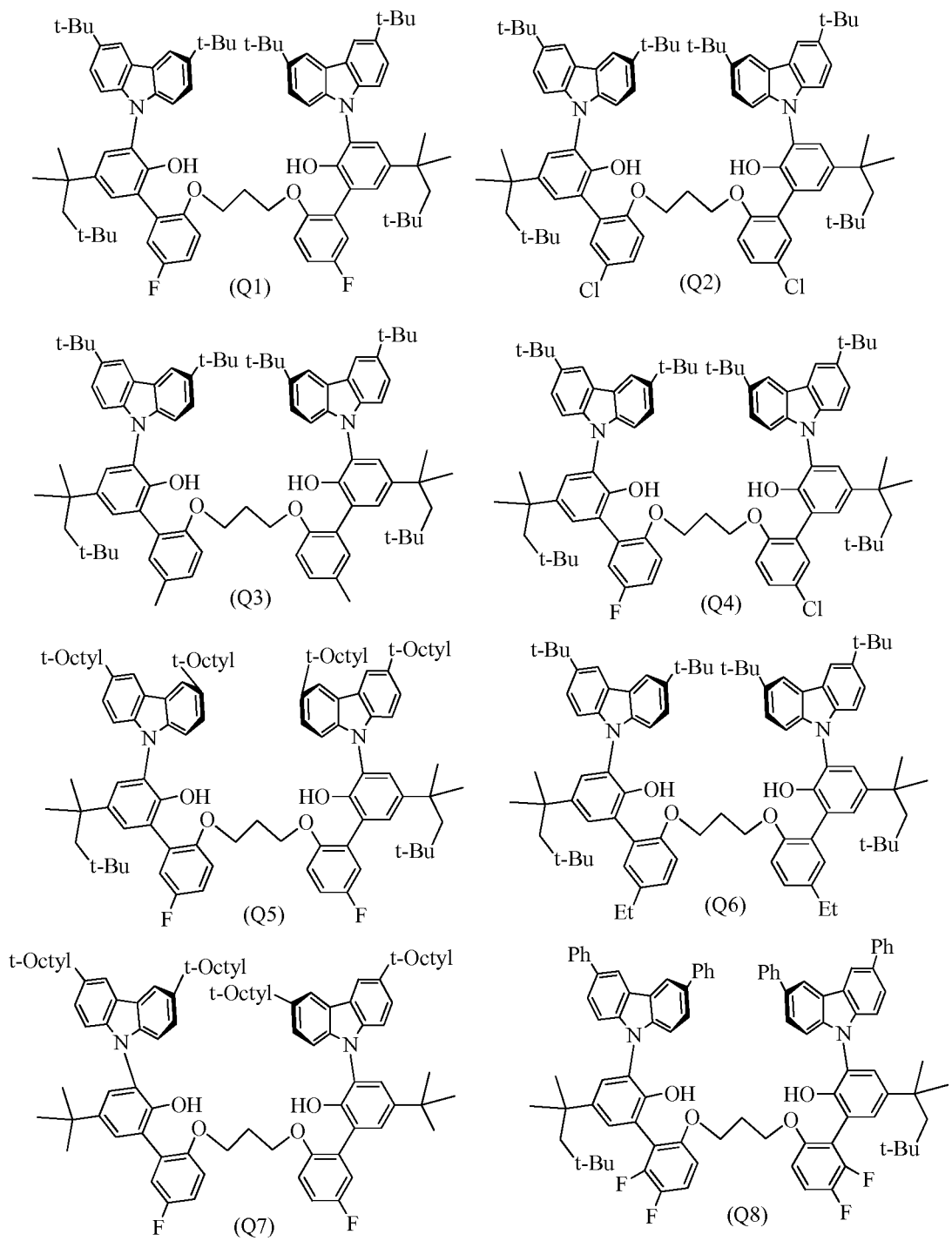
FIG. 5 shows structures of ligands (Q1) to (Q8) of Examples Q1 to Q8.
Figure 6:
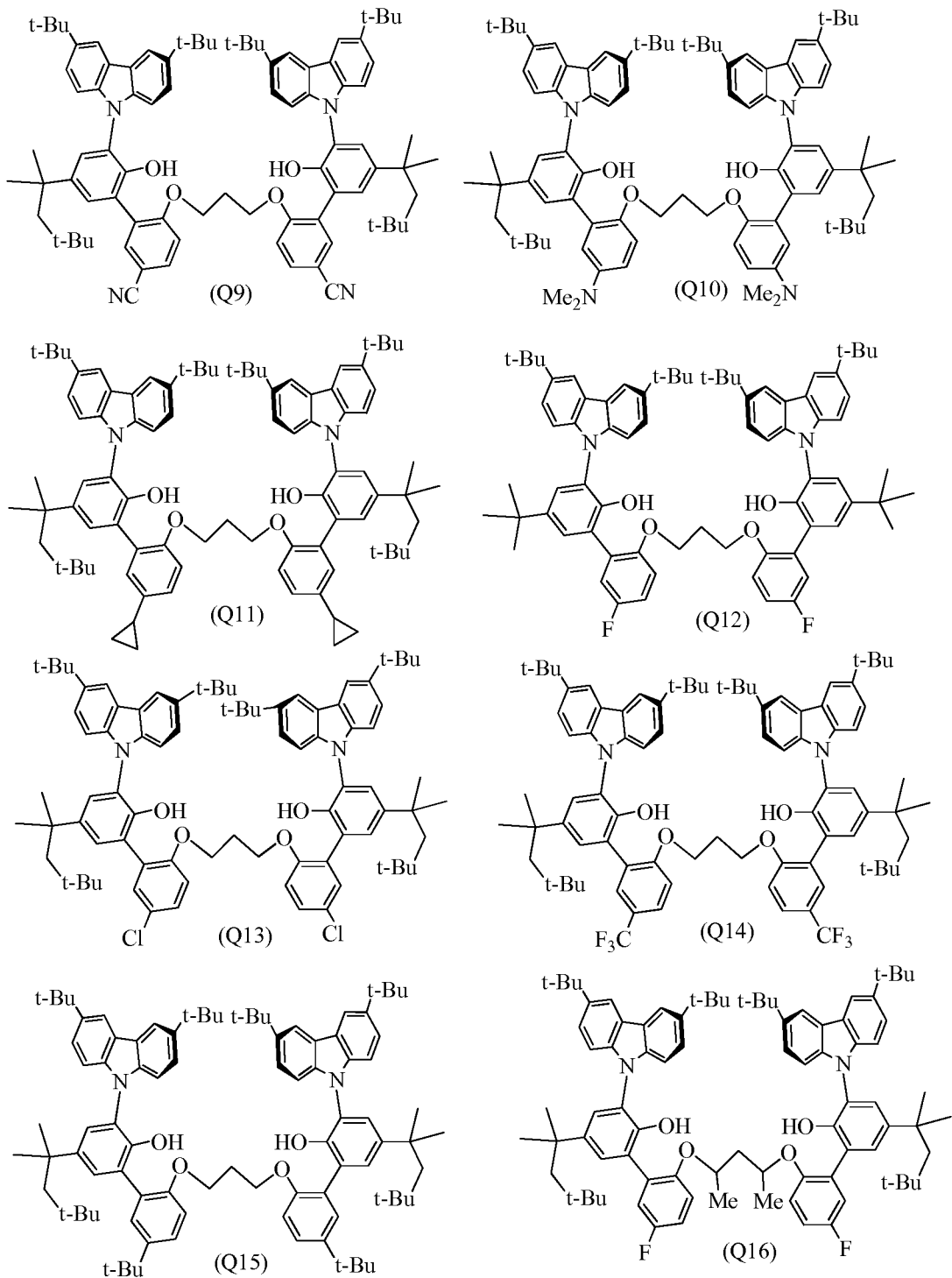
FIG. 6 shows structures of ligands (Q9) to (Q16) of Examples Q9 to Q16.
Figure 7:
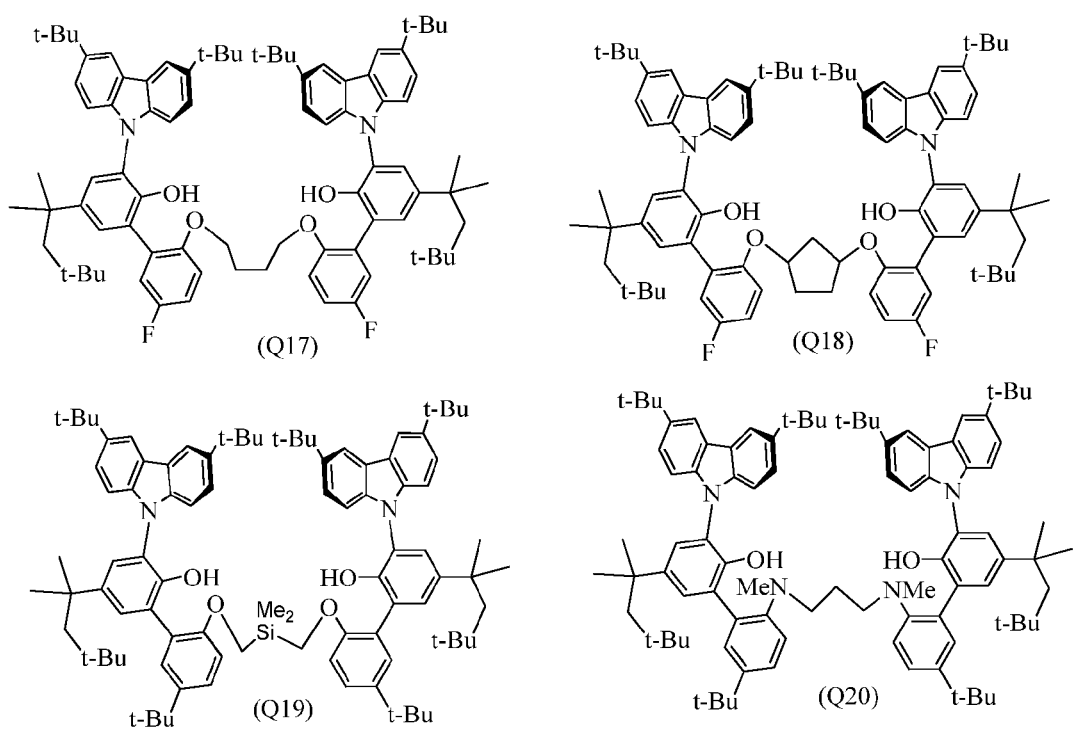
FIG. 7 shows structures of ligands (Q17) to (Q20) of Examples Q17 to Q20.

Structures of ligands (Q1) to (Q8) are shown in FIG. 5. Structures of ligands (Q9) to (Q16) are shown in FIG. 6. Structures of ligands (Q17) to (Q20) are shown in FIG. 7. In FIGS. 5 to 7, "t-butyl" is synonymous with tert-butyl, tertiary-butyl, and 1,1-dimethylethyl. The "Me" means methyl. The "Et" means ethyl. The "t-octyl" is synonymous with tert-octyl, tertiary-octyl, and 1,1,3,3-tetramethylbutyl. The "Ph" means phenyl. The "—CN" is cyano.

Example 1

Preparation of (2',2"-(propane-1,3-diylbis(oxy))bis(3-(3,6-di-tert-butyl-9H-carbazol-9-yl)-5'-fluoro-5-(2,4,4-trimethylpentan-2-yl)biphenyl-2-ol)dimethylhafnium, (1)

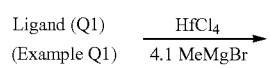

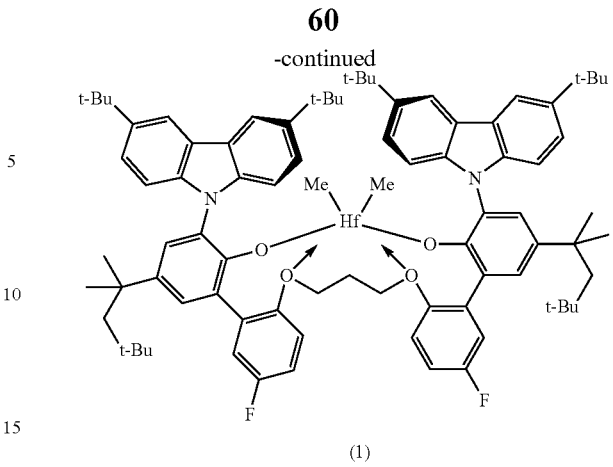

(1)

To a 40 mL toluene solution containing 2',2"-(propane-1,3-diylbis(oxy))bis(3-(3,6-di-tert-butyl-9H-carbazol-9-yl)-5'-fluoro-5-(2,4,4-trimethylpentan-2-yl)biphenyl-2-ol) ligand (Q1), Example Q1, and HfCl$_4$ add 4.1 mole equivalents of methyl magnesium bromide (MeMgBr) at room temperature. After stirring for 1.5 hours, remove solvent under reduced pressure. To the resulting residue add 10 mL of toluene and 30 mL of hexane. Filter the resulting mixture to give a colorless filtrate. Remove solvent to give a white solid. Dissolve the solid in about 30 mL of hexane, and remove the hexane under reduced pressure. To the residue add 25 mL hexane, partly dissolving the residue. Remove solvent under reduced pressure to yield 1.92 g (101%) of (1) (yield greater than 100% because (1) contains a small amount of toluene).

$^1$H NMR (500 MHz, C$_6$D$_6$) δ 8.59 (d, J=1.9 Hz, 2H), 8.39 (d, J=1.9 Hz, 2H), 7.70-7.66 (m, 4H), 7.64 (d, J=8.6 Hz, 2H), 7.57 (d, J=8.8 Hz, 2H), 7.44 (dd, J=8.8, 1.9 Hz, 2H), 7.24 (d, J=2.5 Hz, 2H), 6.96 (dd, J=8.9, 3.2 Hz, 2H), 6.56 (ddd, J=8.9, 7.4, 3.2 Hz, 2H), 4.98 (dd, J=8.9, 5.0 Hz, 2H), 3.77 (dt, J=10.3, 5.2 Hz, 2H), 3.09 (dt, J=10.3, 5.8 Hz, 2H), 1.63 (d, J=14.5 Hz, 2H), 1.58 (d, J=14.5 Hz, 2H), 1.51 (s, 18H), 1.30 (s, 18H), 1.26 (s, 6H), 1.22 (s, 6H), 1.10 (dt, J=10.8, 5.3 Hz, 2H), 0.81 (s, 18H), −1.00 (s, 6H).

$^{13}$C{$^1$H} NMR (126 MHz, C$_6$D$_6$) δ 160.70 (d, J=246.5 Hz), 154.43 (s), 151.25 (d, J=2.5 Hz), 143.11 (s), 142.80 (s), 141.11 (s), 140.28 (s), 140.03 (s), 135.36 (d, J=8.2 Hz), 129.40 (s), 128.14 (s), 127.73 (s), 127.54 (s), 125.67 (d, J=8.8 Hz), 125.33 (s), 125.03 (s), 123.19 (s), 122.76 (s), 118.35 (d, J=23.4 Hz), 117.07 (s), 115.96 (d, J=22.5 Hz), 115.89 (s), 112.71 (s), 108.86 (s), 77.10 (s), 57.11 (s), 49.56 (s), 38.19 (s), 34.94 (s), 34.73 (s), 32.53 (s), 32.34 (s), 32.06 (s), 32.01 (s), 31.55 (s), 29.32 (s).

$^{19}$F NMR (282 MHz, C$_6$D$_6$) δ −113.95 (m).

Figure 8:
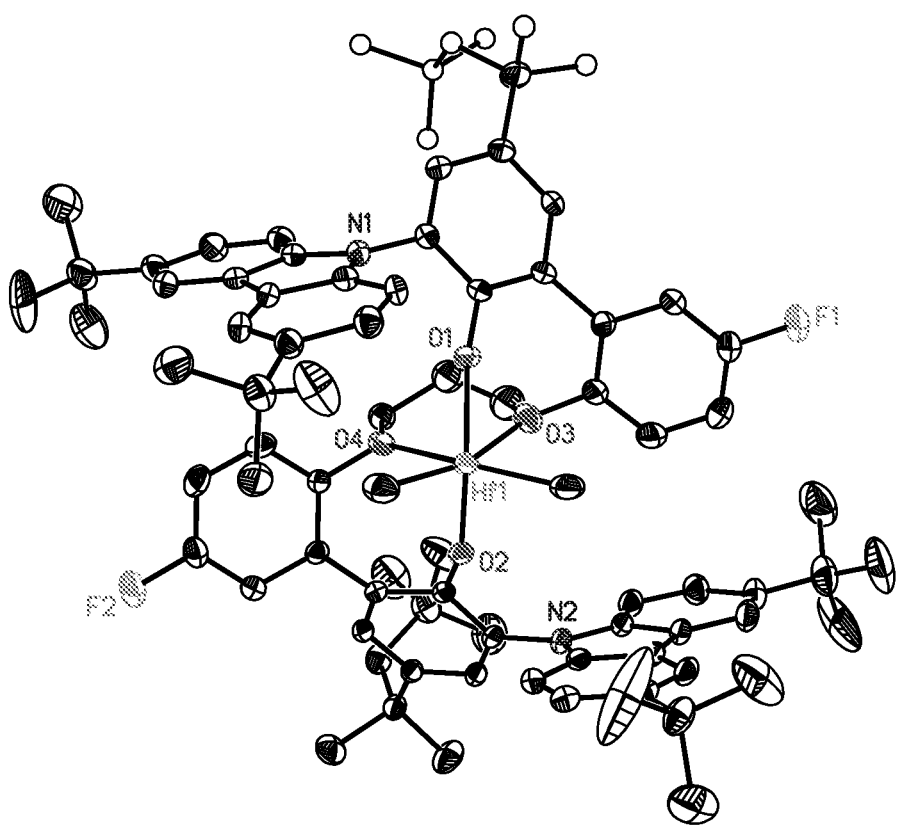
FIG. 8 shows an Oak Ridge Thermal Ellipsoid Plot (ORTEP) depiction of a single crystal structure derived by x-ray analysis of invention metal-ligand complex (1) (Example 1) with hydrogen atoms omitted for clarity.

FIG. 8 shows an ORTEP depiction of a single crystal structure derived by x-ray analysis of invention metal-ligand complex (1) (Example 1). In FIG. 8 hydrogen atoms are omitted for clarity.

Example 2

Preparation of (2',2"-(propane-1,3-diylbis(oxy))bis(3-(3,6-di-tert-butyl-9H-carbazol-9-yl)-5'-chloro-5-(2,4,4-trimethylpentan-2-yl)biphenyl-2-ol)dimethyl-hafnium, (2)

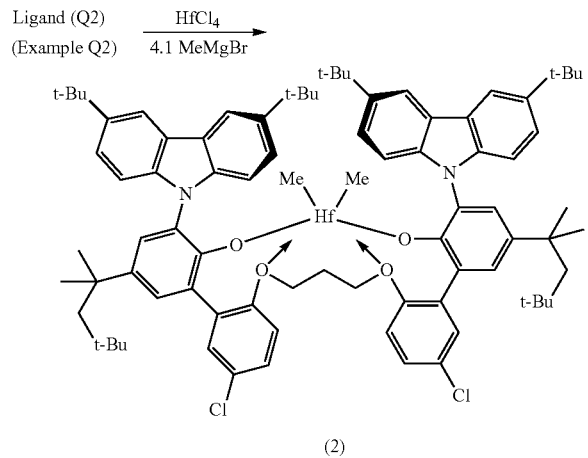

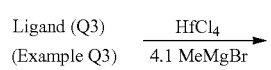

(2)

Repeat the procedure of Example 1 except use Ligand (Q2) instead of ligand (Q1) to yield (2) as a solid.

$^1$H NMR (500 MHz, C$_6$D$_6$) δ 8.54 (d, J=1.8 Hz, 2H), 8.34 (d, J=1.8 Hz, 2H), 7.98 (d, J=8.5 Hz, 2H), 7.94 (d, J=2.4 Hz, 2H), 7.80 (dd, J=8.6, 1.9 Hz, 2H), 7.65 (d, J=8.8 Hz, 2H), 7.43 (dd, J=8.8, 1.9 Hz, 2H), 7.16 (d, J=2.4 Hz, 2H), 7.06 (d, J=2.6 Hz, 2H), 6.66 (d, J=2.6 Hz, 2H), 3.91 (dt, J=10.3, 5.1 Hz, 2H), 3.28 (dt, J=10.6, 5.5 Hz, 2H), 1.65 (d, J=14.5 Hz, 2H), 1.59 (s, 18H), 1.56 (d, J=14.5 Hz, 2H), 1.35 (s, 18H), 1.31 (dt, J=10.6, 5.1 Hz, 2H), 1.24 (s, 6H), 1.21 (s, 6H), 0.83 (s, 18H), −0.73 (s, 6H).

$^{13}$C{$^1$H} NMR (126 MHz, C$_6$D$_6$) δ 153.27 (s), 149.70 (s), 142.90 (s), 142.82 (s), 141.01 (s), 139.97 (s), 139.59 (s), 132.18 (s), 131.96 (s), 130.46 (s), 129.43 (s), 128.90 (s), 128.60 (s), 127.24 (s), 127.10 (s), 125.78 (s), 124.42 (s), 123.64 (s), 123.31 (s), 117.40 (s), 116.09 (s), 113.48 (s), 110.22 (s), 76.49 (s), 57.49 (s), 50.04 (s), 38.23 (s), 35.00 (s), 34.72 (s), 32.53 (s), 32.37 (s), 32.03 (s), 31.97 (s), 31.75 (s), 31.29 (s), 29.67 (s).

Figure 9:
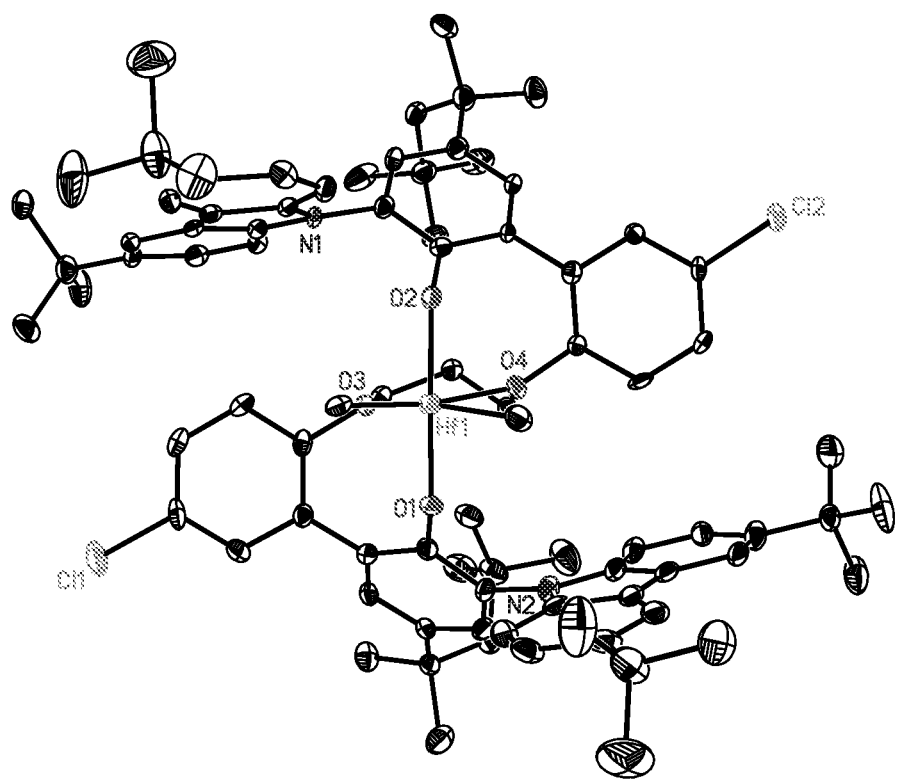
FIG. 9 shows an Oak Ridge Thermal Ellipsoid Plot (ORTEP) depiction of a single crystal structure derived by x-ray analysis of invention metal-ligand complex (2) (Example 2) with hydrogen atoms omitted for clarity.

FIG. 9 shows an ORTEP depiction of a single crystal structure derived by x-ray analysis of invention metal-ligand complex (2) (Example 2). In FIG. 9 hydrogen atoms are omitted for clarity.

Example 3

Preparation of (2',2"-(propane-1,3-diylbis(oxy))bis(3-(3,6-di-tert-butyl-9H-carbazol-9-yl)-5'-methyl-5-(2,4,4-trimethylpentan-2-yl)biphenyl-2-ol)dimethyl-hafnium, (3)

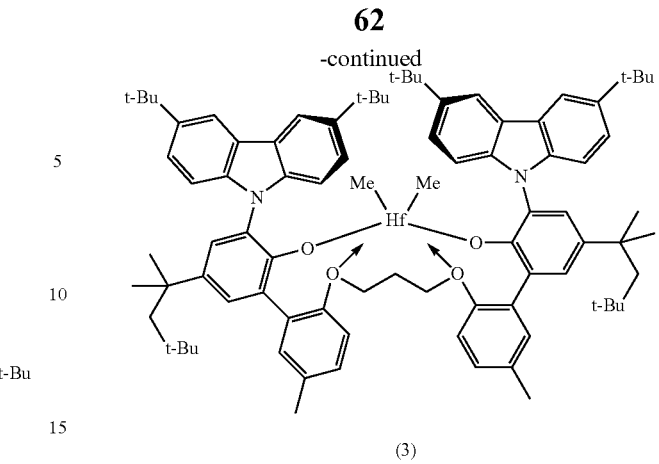

(3)

Repeat the procedure of Example 1 except use Ligand (Q3) instead of ligand (Q1) to yield (3) as a solid.

Example 4

Preparation of 2',2"-(propane-1,3-diylbis(oxy))-1-(3,6-di-tert-butyl-9H-carbazol-9-yl)-5'-fluoro-5-(2,4,4-trimethylpentan-2-yl)biphenyl-2-ol)-3-(3,6-di-tert-butyl-9H-carbazol-9-yl)-5'-chloro-5-(2,4,4-trimethylpentan-2-yl)biphenyl-2-ol)dimethyl-hafnium, (4)

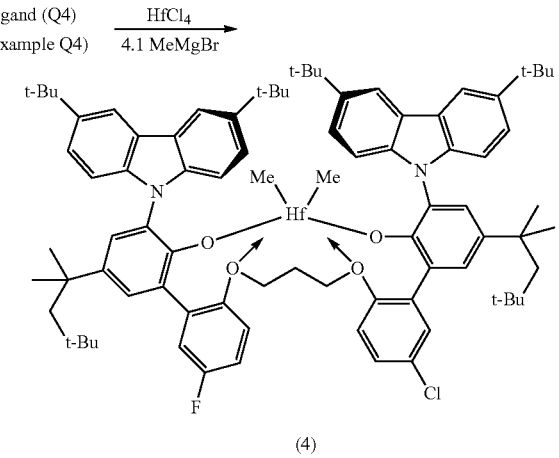

(4)

Repeat the procedure of Example 1 except use Ligand (Q4) instead of ligand (Q1) to yield (4) as a solid.

Examples 5 to 20

Preparation of Metal-Ligand Complexes (5) to (20)

In a manner similar to the preparation of Examples 1 to 4 except where alternative starting materials are used as appropriate, the metal-ligand complexes (5) to (20) can be prepared.

Figure 10:
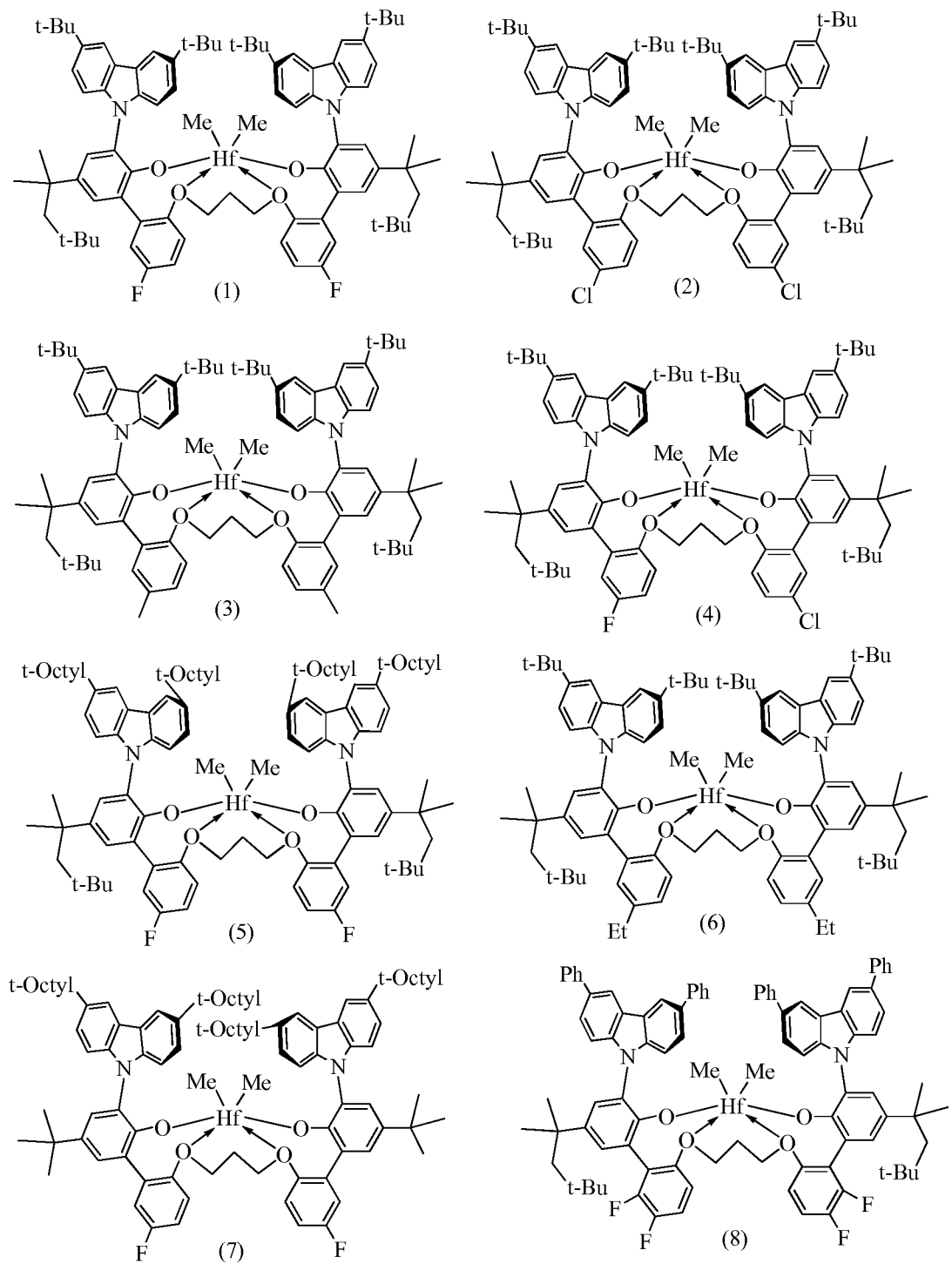
FIG. 10 shows structures of metal-ligand complexes (1) to (8) of Examples 1 to 8.
Figure 11:
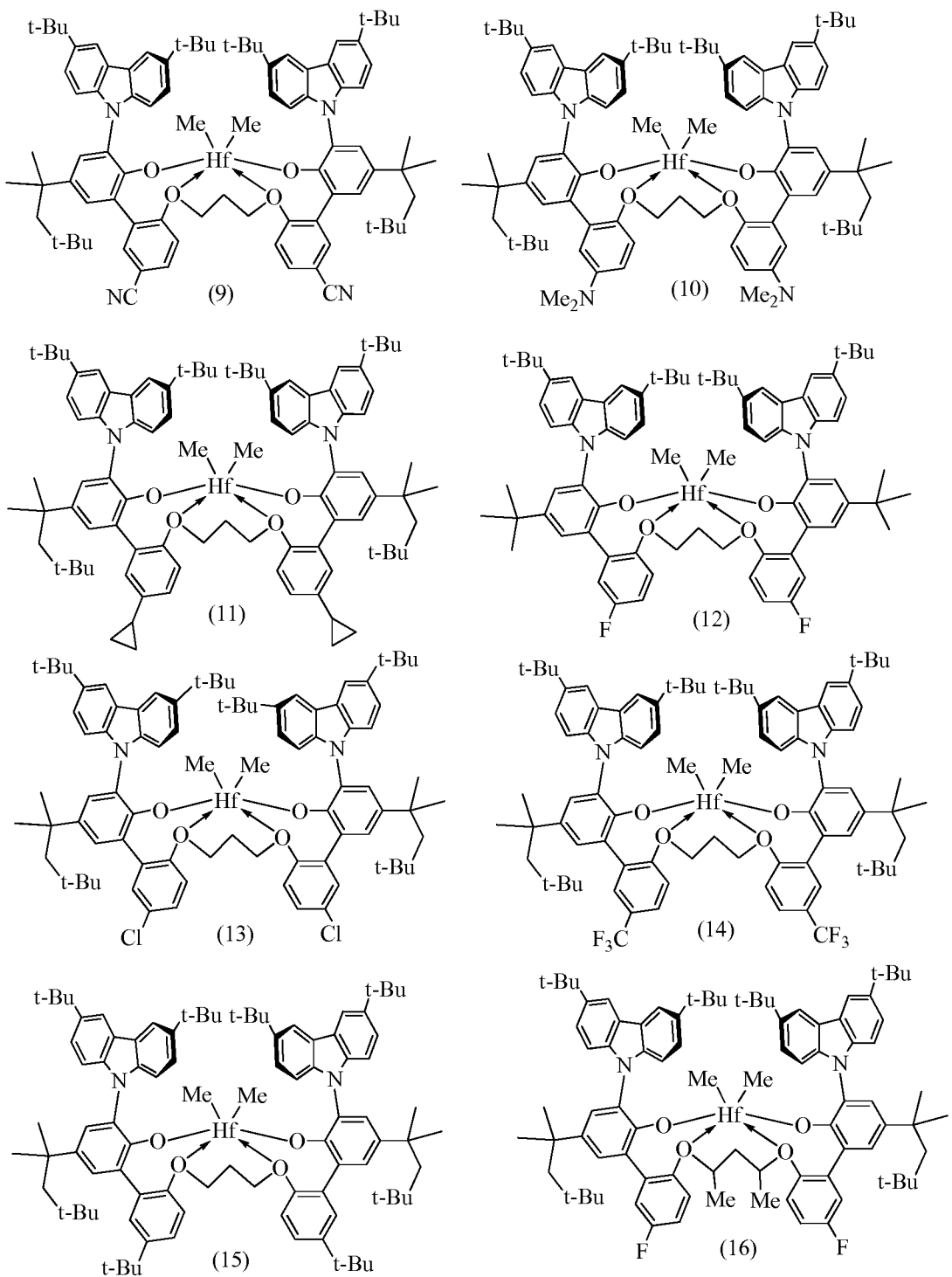
FIG. 11 shows structures of metal-ligand complexes (9) to (16) of Examples 9 to 16.
Figure 12:
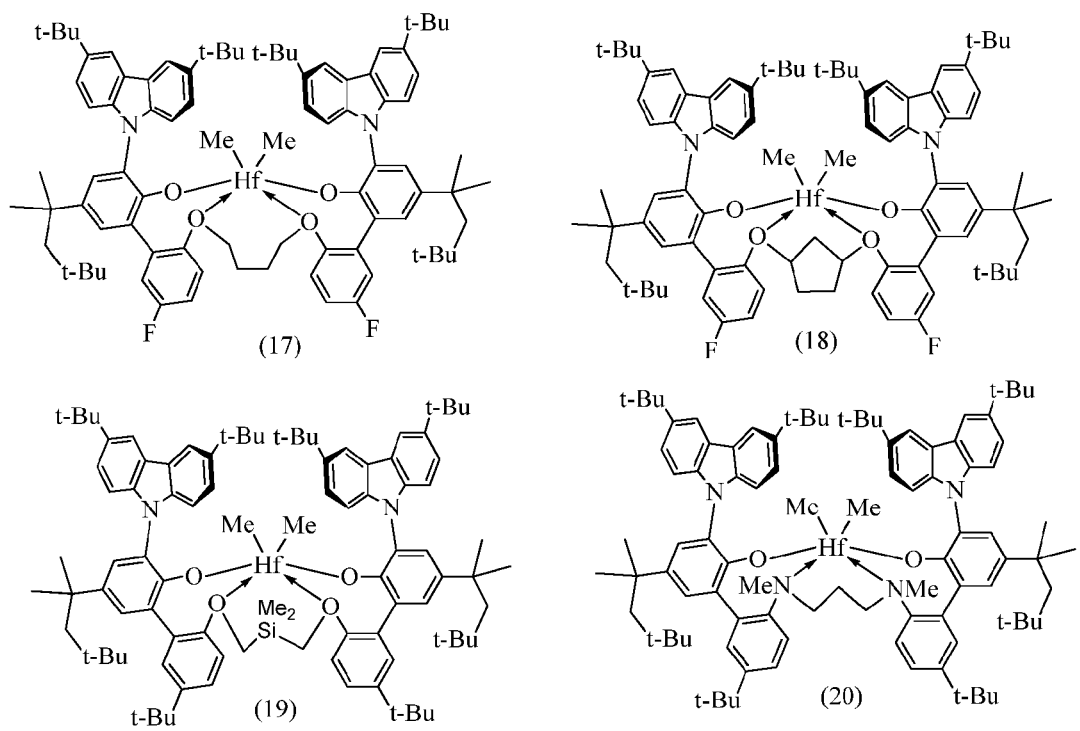
FIG. 12 shows structures of metal-ligand complexes (17) to (20) of Examples 17 to 20.

(2',2"-(propane-1,3-diylbis(oxy))bis(3-(3,6-di-tert-octyl-9H-carbazol-9-yl)-5'-fluoro-5-(2,4,4-trimethylpentan-2-yl)biphenyl-2-ol)dimethyl-hafnium, (5);

(2',2"-(propane-1,3-diylbis(oxy))bis(3-(3,6-di-tert-butyl-9H-carbazol-9-yl)-5'-ethyl-5-(2,4,4-trimethylpentan-2-yl)biphenyl-2-ol)dimethyl-hafnium, (6);

(2',2"-(propane-1,3-diylbis(oxy))bis(3-(3,6-di-tert-octyl-9H-carbazol-9-yl)-5'-fluoro-5-(tert-butyl)biphenyl-2-ol) dimethyl-hafnium, (7);

(2',2"-(propane-1,3-diylbis(oxy))bis(3-(3,6-diphenyl-9H-carbazol-9-yl)-5',6'-difluoro-5-(2,4,4-trimethylpentan-2-yl)biphenyl-2-ol)dimethyl-hafnium, (8);

(2',2"-(propane-1,3-diylbis(oxy))bis(5'-cyano-3-(3,6-di-tert-butyl-9H-carbazol-9-yl)-5-(2,4,4-trimethylpentan-2-yl)biphenyl-2-ol)dimethyl-hafnium, (9);

(2',2"-(propane-1,3-diylbis(oxy))bis(5'-dimethylamino-3-(3,6-di-tert-butyl-9H-carbazol-9-yl)-5-(2,4,4-trimethylpentan-2-yl)biphenyl-2-ol)dimethyl-hafnium, (10);

(2',2"-(propane-1,3-diylbis(oxy))bis(5'-cyclopropyl-3-(3,6-di-tert-butyl-9H-carbazol-9-yl)-5-(2,4,4-trimethylpentan-2-yl)biphenyl-2-ol)dimethyl-hafnium, (11);

(2',2"-(propane-1,3-diylbis(oxy))bis(5'-fluoro-3-(3,6-di-tert-butyl-9H-carbazol-9-yl)-5-(tert-butyl)biphenyl-2-ol) dimethyl-hafnium, (12);

(2',2"-(propane-1,3-diylbis(oxy))bis(3-(3,6-di-tert-butyl-9H-carbazol-9-yl)-5'-chloro-6-(2,4,4-trimethylpentan-2-yl)biphenyl-2-ol)dimethyl-hafnium, (13);

(2',2"-(propane-1,3-diylbis(oxy))bis(3-(3,6-di-tert-butyl-9H-carbazol-9-yl)-5'-trifluoromethyl-5-(2,4,4-trimethylpentan-2-yl)biphenyl-2-ol)dimethyl-hafnium, (14);

(2',2"-(propane-1,3-diylbis(oxy))bis(3-(3,6-di-tert-butyl-9H-carbazol-9-yl)-5'-(tert-butyl)-5-(2,4,4-trimethylpentan-2-yl)biphenyl-2-ol)dimethyl-hafnium, (15);

(2',2"-(1,3-dimethylpropane-1,3-diylbis(oxy))bis(3-(3,6-di-tert-butyl-9H-carbazol-9-yl)-5'-fluoro-5-(2,4,4-trimethylpentan-2-yl)biphenyl-2-ol)dimethyl-hafnium, (16);

(2',2"-(butane-1,3-diylbis(oxy))bis(3-(3,6-di-tert-butyl-9H-carbazol-9-yl)-5'-fluoro-5-(2,4,4-trimethylpentan-2-yl)biphenyl-2-ol)dimethyl-hafnium, (17);

(2',2"-(cyclopentan-1,3-diylbis(oxy))bis(3-(3,6-di-tert-butyl-9H-carbazol-9-yl)-5'-fluoro-5-(2,4,4-trimethylpentan-2-yl)biphenyl-2-ol)dimethyl-hafnium, (18);

(2',2"-(2,2-dimethyl-2-silapropane-1,3-diylbis(oxy))bis(3-(3,6-di-tert-butyl-9H-carbazol-9-yl)-5'-fluoro-5-(2,4,4-trimethylpentan-2-yl)biphenyl-2-ol)dimethyl-hafnium, (19);

(2',2"-(propane-1,3-diylbis(N-methyl-aza))bis(3-(3,6-di-tert-butyl-9H-carbazol-9-yl)-5'-(tert-butyl)-5-(2,4,4-trimethylpentan-2-yl)biphenyl-2-ol)dimethyl-hafnium, (20);

Structures of metal-ligand complexes (1) to (8) are shown in FIG. 10. Structures of metal-ligand complexes (9) to (16) are shown in FIG. 11. Structures of metal-ligand complexes (17) to (20) are shown in FIG. 12. In FIGS. 10 to 12, "t-butyl" is synonymous with tert-butyl, tertiary-butyl, and 1,1-dimethylethyl. The "Me" means methyl. The "Et" means ethyl. The "Ph" means phenyl. The "t-octyl" is synonymous with tert-octyl, tertiary-octyl, and 1,1,3,3-tetramethylbutyl. The "—CN" is cyano.

In some embodiments at least one of the at least one metal-ligand complex of formula (I) is metal-ligand complex (1). In some embodiments at least one of the at least one metal-ligand complex of formula (I) is metal-ligand complex (2). In some embodiments at least one of the at least one metal-ligand complex of formula (I) is metal-ligand complex (3). In some embodiments at least one of the at least one metal-ligand complex of formula (I) is metal-ligand complex (4). In some embodiments at least one of the at least one metal-ligand complex of formula (I) is any one of metal-ligand complexes (5) to (20).

Examples 21 to 40

Preparation of Metal-Ligand Complexes (21) to (40)

In a manner similar to the preparation of Examples 1 to 20 except using zirconium tetrachloride instead of hafnium tetrachloride, the metal-ligand complexes (21) to (40) can be prepared.

(2',2"-(propane-1,3-diylbis(oxy))bis(3-(3,6-di-tert-butyl-9H-carbazol-9-yl)-5'-fluoro-5-(2,4,4-trimethylpentan-2-yl)biphenyl-2-ol)dimethyl-zirconium, (21)

(2',2"-(propane-1,3-diylbis(oxy))bis(3-(3,6-di-tert-butyl-9H-carbazol-9-yl)-5'-chloro-5-(2,4,4-trimethylpentan-2-yl)biphenyl-2-ol)dimethyl-zirconium, (22);

(2',2"-(propane-1,3-diylbis(oxy))bis(3-(3,6-di-tert-butyl-9H-carbazol-9-yl)-5'-methyl-5-(2,4,4-trimethylpentan-2-yl)biphenyl-2-ol)dimethyl-zirconium, (23);

2',2"-(propane-1,3-diylbis(oxy))-1-(3,6-di-tert-butyl-9H-carbazol-9-yl)-5'-fluoro-5-(2,4,4-trimethylpentan-2-yl)biphenyl-2-ol)-3-(3,6-di-tert-butyl-9H-carbazol-9-yl)-5'-chloro-5-(2,4,4-trimethylpentan-2-yl)biphenyl-2-ol) dimethyl-zirconium, (24);

(2',2"-(propane-1,3-diylbis(oxy))bis(3-(3,6-di-tert-octyl-9H-carbazol-9-yl)-5'-fluoro-5-(2,4,4-trimethylpentan-2-yl)biphenyl-2-ol)dimethyl-zirconium, (25);

(2',2"-(propane-1,3-diylbis(oxy))bis(3-(3,6-di-tert-butyl-9H-carbazol-9-yl)-5'-ethyl-5-(2,4,4-trimethylpentan-2-yl)biphenyl-2-ol)dimethyl-zirconium, (26);

(2',2"-(propane-1,3-diylbis(oxy))bis(3-(3,6-di-tert-butyl-9H-carbazol-9-yl)-5'-fluoro-5-(2,4,4-trimethylpentan-2-yl)biphenyl-2-ol)dimethyl-zirconium, (27);

(2',2"-(propane-1,3-diylbis(oxy))bis(3-(3,6-diphenyl-9H-carbazol-9-yl)-5',6'-difluoro-5-(2,4,4-trimethylpentan-2-yl)biphenyl-2-ol)dimethyl-zirconium, (28);

(2',2"-(propane-1,3-diylbis(oxy))bis(5'-cyano-3-(3,6-di-tert-butyl-9H-carbazol-9-yl)-5-(2,4,4-trimethylpentan-2-yl)biphenyl-2-ol)dimethyl-zirconium, (29);

(2',2"-(propane-1,3-diylbis(oxy))bis(5'-dimethylamino-3-(3,6-di-tert-butyl-9H-carbazol-9-yl)-5-(2,4,4-trimethylpentan-2-yl)biphenyl-2-ol)dimethyl-zirconium, (30);

(2',2"-(propane-1,3-diylbis(oxy))bis(5'-cyclopropyl-3-(3,6-di-tert-butyl-9H-carbazol-9-yl)-5-(2,4,4-trimethylpentan-2-yl)biphenyl-2-ol)dimethyl-zirconium, (31);

(2',2"-(propane-1,3-diylbis(oxy))bis(5'-fluoro-3-(3,6-di-tert-butyl-9H-carbazol-9-yl)-5-(tert-butyl)biphenyl-2-ol) dimethyl-zirconium, (32);

(2',2"-(propane-1,3-diylbis(oxy))bis(5'-methoxy-3-(3,6-di-tert-octyl-9H-carbazol-9-yl)-5-(tert-butyl)biphenyl-2-ol) dimethyl-zirconium, (33);

(2',2"-(propane-1,3-diylbis(oxy))bis(3-(3,6-di-tert-butyl-9H-carbazol-9-yl)-5'-trifluoromethyl-5-(2,4,4-trimethylpentan-2-yl)biphenyl-2-ol)dimethyl-zirconium, (34);

(2',2"-(propane-1,3-diylbis(oxy))bis(3-(3,6-di-tert-butyl-9H-carbazol-9-yl)-5'-(tert-butyl)-5-(2,4,4-trimethylpentan-2-yl)biphenyl-2-ol)dimethyl-zirconium, (35);

(2',2"-(1,3-dimethylpropane-1,3-diylbis(oxy))bis(3-(3,6-di-tert-butyl-9H-carbazol-9-yl)-5'-fluoro-5-(2,4,4-trimethylpentan-2-yl)biphenyl-2-ol)dimethyl-zirconium, (36);

(2',2"-(butane-1,3-diylbis(oxy))bis(3-(3,6-di-tert-butyl-9H-carbazol-9-yl)-5'-fluoro-5-(2,4,4-trimethylpentan-2-yl)biphenyl-2-ol)dimethyl-zirconium, (37);

(2',2"-(cyclopentan-1,3-diylbis(oxy))bis(3-(3,6-di-tert-butyl-9H-carbazol-9-yl)-5'-fluoro-5-(2,4,4-trimethylpentan-2-yl)biphenyl-2-ol)dimethyl-zirconium, (38);

(2',2"-(2,2-dimethyl-2-silapropane-1,3-diylbis(oxy))bis(3-(3,6-di-tert-butyl-9H-carbazol-9-yl)-5'-fluoro-5-(2,4,4-trimethylpentan-2-yl)biphenyl-2-ol)dimethyl-zirconium, (39); and (2',2"-(propane-1,3-diylbis(N-methyl-aza))bis(3-(3,6-di-tert-butyl-9H-carbazol-9-yl)-5'-(tert-butyl)-5-(2,4,4-trimethylpentan-2-yl)biphenyl-2-ol)dimethyl-zirconium, (40).

Example 41

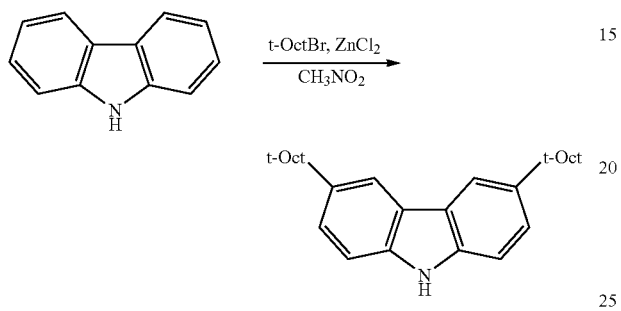

Preparation of 3,6-bis-(2,2,4,4-tetramethylbutyl)-carbazole

ZnCl$_2$ (36.8 g, 276 mmol) and carbazole (21.0 g, 126 mmol) are suspended in 600 mL nitromethane in a 1 qt jar in a glove-box. The t-octyl bromide (53.4 g, 276 mmol) is added dropwise to the gray-green suspension via addition funnel. The mixture turns into a black solution during the addition. The solution is allowed to stir at room temperature for two hours and then poured into 500 mL ice water. The product is extracted out of the mixture with 500 mL and 250 mL CH$_2$Cl$_2$. The combined organic portions are dried with MgSO$_4$, filtered and rotovapped to yield a dark residue. This residue is taken up in 200 mL toluene, passed through a plug of silica, and washed through with 150 mL toluene. The yellow solution is reduced to a solid on the rotovap. This material is recrystallized from 100 mL hexane at −13° C. 27 g (55%) of white crystals are collected. The crystallization only moderately improved the purity of the product. $^1$H NMR (CDCl$_3$): δ 8.02 (d, J$_{H-H}$=1.6 Hz, 2H), 7.80 (br s, 1H, NH), 7.42 (dd, J$_{H-H}$=8.6, 1.8 Hz, 2H), 7.29 (d, J$_{H-H}$=8.5 Hz, 2H), 1.83 (s, 4H, CH$_2$), 1.49 (s, 12H, CMe$_2$), 0.72 (s, 18H, CMe$_3$).

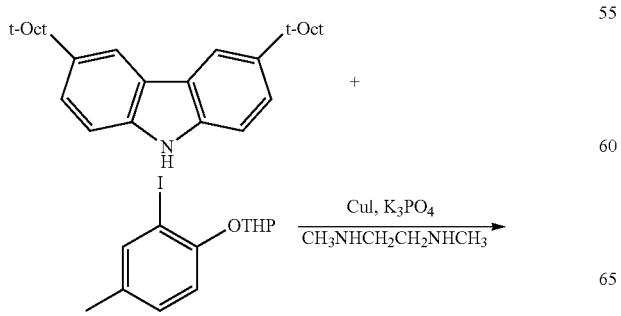

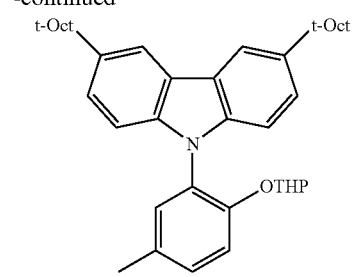

Preparation of 9-(5-methyl-2-((tetrahydro-2H-pyran-2-yl)oxy)phenyl)-3,6-bis(2,4,4-trimethylpentan-2-yl)-9H-carbazole The 2-(2-iodo-4-methylphenoxy)tetrahydro-2H-pyran (12.0 g, 44.3 mmol) is dissolved in 250 mL dioxane in a 500 mL round-bottom flask.

The 3,6-bis-(2,2,4,4-tetramethylbutyl)-carbazole (19.1 g, 48.7 mmol), K$_3$PO$_4$ (18.8 g, 88.5 mmol), N,N'-dimethylethylenediamine (1.98 g, 23.0 mmol), and CuI (2.11 g, 11.1 mmol) are added and the mixture is refluxed for four days with a Stevens condensor in the glovebox. The mixture is brought outside of the glovebox and filtered to remove the salts. The solution is then passed through a plug of alumina and rotovapped down to yield a gold oil. GC/Mass Spec and $^1$H NMR reveal that the mixture is 70% desired product. The material is recrystallized from cold hexanes (11.5 g, 44.7% yield).

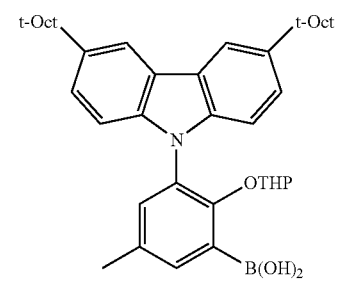

Preparation of (3-(3,6-bis(2,4-trimethylpentan-2-yl)-9H-carbazol-9-yl)-5-methyl-2-((tetrahydro-2H-pyran-2-yl)oxy)phenyl)boronic acid The 9-(5-methyl-2-((tetrahydro-2H-pyran-2-yl)oxy)phenyl)-3,6-bis(2,4-trimethylpentan-2-yl)-9H-carbazole (5.00 g, 8.6 mmol) is dissolved in 50 mL THF in a 250 mL round bottom flask in an ice water bath. n-BuLi (7.0 ml of a 1.6 M solution in hexane, 11.2 mmol) is added dropwise via syringe (soln turns yellow in color) and the brown solution stirred for 3 hours. Triisopropylborate (2.37 mL, 11.2 mmol) is added dropwise via syringe and the solution stirred for one hour, during which time the mixture became turbid and darkened in color. The mixture is quenched with 100 mL ice water. The solution is extracted with 2×100 mL Et$_2$O. The combined organic portions are dried with MgSO4, filtered and rotovapped down to a white solid (5.1 g). This solid is added to 200 mL water and stirred for 1.5 hrs. The mixture is extracted with 150 and 100 mL Et$_2$O. The combined organic extract is dried with MgSO$_4$, filtered and rotovapped down to yield 4.2 g (78% yield) of a white powder. $^1$H NMR (CDCl$_3$): δ 8.07 (d, J$_{H—H}$=1.4 Hz, 1H, CBZ), 8.04 (d, J$_{H—H}$=1.4 Hz, 1H, CBZ), 7.69 (d, J$_{H—H}$=2.3 Hz, 1H, aryl), 7.42 (dd, J$_{H—H}$=8.6, 1.8 Hz, 2H, CBZ), 7.40 (dd, J$_{H—H}$=8.6, 1.7 Hz, 1H, CBZ), 7.37 (d, J$_{H—H}$=2.3 Hz, 1H, aryl), 7.18 (d, J$_{H—H}$=8.6 Hz, 1H, CBZ), 6.99 (d, J$_{H—H}$=8.6 Hz, 1H, CBZ), 6.34 (s, 2H, OH), 3.80 (m, 2H, THP), 2.91 (m, 1H, THP), 2.39 (s, 3H, aryl Me), 1.89 (dd, J$_{H—H}$=12.8, 4.2 Hz, 2H, $^t$OCT CH$_2$), 1.82 (d, J$_{H—H}$=14.5 Hz, 2H, $^t$OCT CH$_2$), 1.55 (s, 3H, $^t$OCT CMe$_2$), 1.52 (s, 3H, $^t$OCT CMe$_2$), 1.48 (s, 3H, $^t$OCT CMe$_2$), 1.45 (s, 3H, $^t$OCT CMe$_2$), 0.71 (s, 9H, $^t$OCT $^t$Bu), 0.70 (s, 9H, $^t$OCT $^t$Bu).

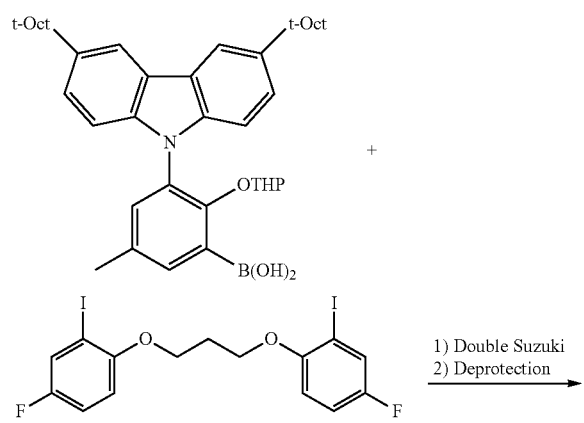

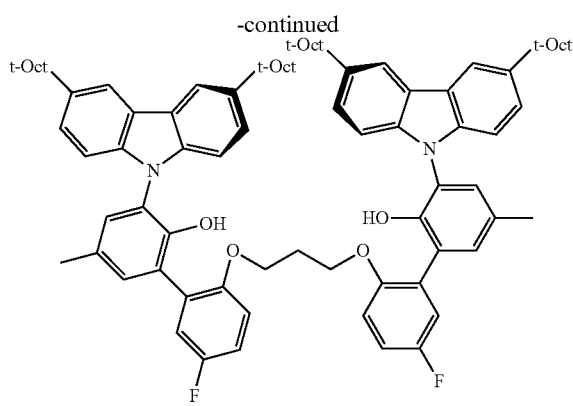

Preparation of 2',2''-(propane-1,3-diylbis(oxy))bis(3-(3,6-bis(2,4-trimethylpentan-2-yl)-9H-carbazol-9-yl)-5'-fluoro-5-methyl-biphenyl-2-ol The (3-(3,6-bis(2,4-trimethylpentan-2-yl)-9H-carbazol-9-yl)-5-methyl-2-((tetrahydro-2H-pyran-2-yl)oxy)phenyl) boronic acid is dissolved in 20 mL of dimethoxyethane. This solution is then treated with a solution of NaOH (0.58 g, 14.5 mmol) in 10 mL of water, 10 mL of tetrahydrofuran and the 1,3-bis(4-fluoro-2-iodophenoxy)propane (1.25 g, 2.42 mmol). The system is purged with nitrogen and Pd(PPh$_3$)$_4$ (98 mg, 0.08 mmol) is added. The mixture is then heated to 85° C. overnight under nitrogen atmosphere. The reaction mixture is cooled and the volatile material is removed by rotary evaporation. The residue is treated with 40 mL of water and extracted with 2×40 mL methylene chloride. The methylene chloride solution is washed with 40 mL each of water and brine, and dried over anhydrous magnesium sulfate. This solution is concentrated by rotary evaporation. The residue was dissolved in 25 mL of tetrahydrofuran and treated with 20 mL of methanol and 0.25 mL of concentrated hydrochloric acid. The solution is then refluxed for 4 hours. The solution is reduced to a yellow solid (3.5 g). This material is taken up in 10 mL Et$_2$O and layered with 30 mL MeOH. The Et$_2$O is allowed to evaporate off and a pale yellow material (1.9 g, 62%) settle on the bottom of the flask. A $^1$H NMR spectrum of this material is clean and consistent with the desired product. An additional 0.34 g (68% total yield) is collected after two recrystallizations of the mother liquor at −13° C. $^1$H NMR (CDCl$_3$): δ 8.15 (d, J$_{H-H}$=1.3 Hz, 4H, CBZ), 7.38 (dd, J$_{H-H}$=8.6, 1.6 Hz, 4H, CBZ), 7.17 (d, J$_{H-H}$=2.0 Hz, 2H, p-Me-aryl H), 7.03 (d, J$_{H-H}$=2.0 Hz, p-Me-aryl H), 7.01 (d, J$_{H-H}$=8.6 Hz, 4H, CBZ), 6.94 (dd, J$_{H-H(F)}$=8.8, 3.1 Hz, 2H, p-F-aryl H), 6.44 (td, J$_{H-H(F)}$=8.9, 3.1 Hz, 2H, p-F-aryl H), 5.95 (dd, J$_{H-H(F)}$=9.0, 4.4 Hz, 2H, p-F-aryl H), 5.28 (s, 2H, OH), 3.79 (t, J$_{H-H}$=5.4 Hz, 4H, OCH$_2$), 2.30 (s, 6H, p-Me), 1.97 (quint, J$_{H-H}$=5.4 Hz, 2H, OCH$_2$CH$_2$), 1.85 (s, 8H, $^t$OCT CH$_2$), 1.50 (s, 24H, $^t$OCT CMe$_2$), 0.74 (s, 36H, $^t$OCT CMe$_3$). $^{13}$C NMR (CDCl$_3$): δ 156.9 (d, J$_{C-F}$=565 Hz, ipso C—F), 151.2, 148.0, 142.0, 139.6, 131.7, 130.3, 129.4, 127.7 (d, J$_{C-F}$=7.8 Hz, meta to C—F), 126.6, 124.7, 124.5, 123.4, 118.0 (d, J$_{C-F}$=23.4 Hz, ortho to C—F), 117.0, 115.1 (d, J$_{C-F}$=22.6 Hz, ortho to C—F), 112.7 (d, J$_{C-F}$=8.5 Hz, meta to C—F), 109.1, 64.8, 57.3, 38.7, 32.5, 32.2, 31.9, 28.8, 20.5.

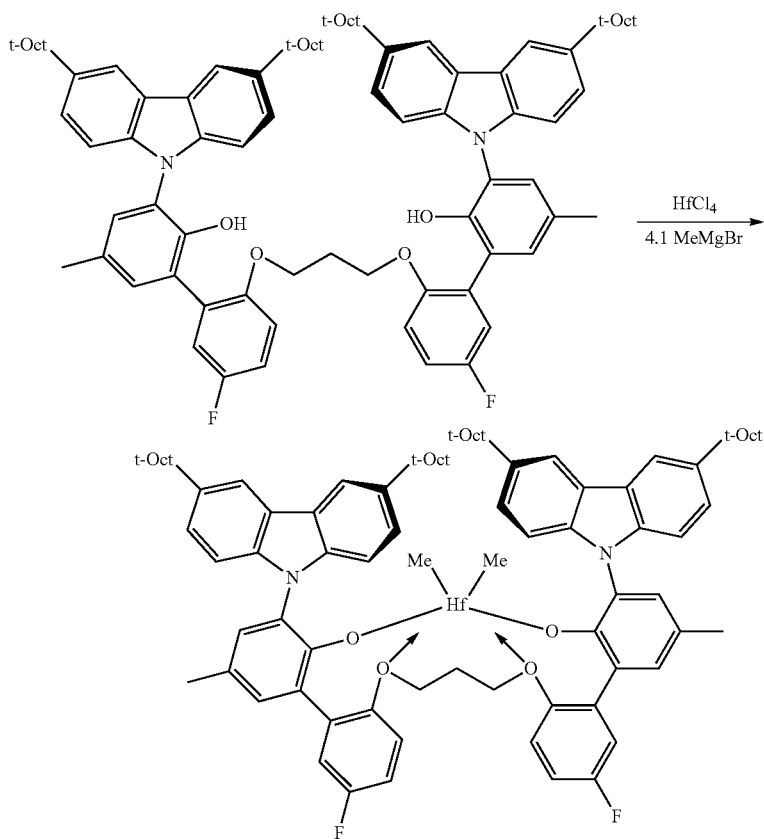

Preparation of (2',2''-(propane-1,3-diylbis(oxy))bis
(3-(3,6-bis(2,4,4-trimethylpentan-2-yl)-9H-carbazol-
9-yl)-5'-fluoro-5-methyl-biphenyl-2-ol)dimethyl-
hafnium The 2',2''-(propane-1,3-diylbis(oxy))bis(3-(3,6-bis(2,4,4-trimethylpentan-2-yl)-9H-carbazol-9-yl)-5'-fluoro-5-methyl-biphenyl-2-ol (1.88 g, 1.50 mmol) and HfCl$_4$ (0.48 g, 1.50 mmol) is suspended in 30 mL toluene in a schlenk round-bottom flask and cooled in an ice-water bath. Methylmagnesium bromide (3.0 M, 2.3 mL, 6.75 mmol) is added dropwise to the yellow-green mixture via syringe. The solution is stirred and warmed slowly to room temp. After the addition of the Grignard reagent, the solution turned slightly dark tan. The solution is stirred for 3.5 hours. The solution is reduced to dryness under vacuum, and the solids are extracted with 50 mL toluene. The mixture is filtered and the dark solids are washed with an additional 25 mL toluene. The colorless filtrate is reduced to dryness under vacuum to yield 1.15 g (52%) of a white-yellow solid. $^1$H NMR (CDCl$_3$): δ 8.24 (d, J$_{H-H}$=1.3 Hz, 2H, CBZ), 8.05 (d, J$_{H-H}$=1.3 Hz, 2H, CBZ), 7.38 (dd, J$_{H-H}$=8.6, 1.6 Hz, 4H, CBZ), 7.36 (d, J$_{H-H}$=1.9 Hz, 2H, p-Me-aryl H), 7.02 (d, J$_{H-H}$=2.1 Hz, 2H, p-Me-aryl H), 6.94 (dd, J$_{H-H(F)}$=8.8, 3.1 Hz, 2H, p-F-aryl H), 6.26 (td, J$_{H-H(F)}$=7.3, 3.2 Hz, 2H, p-F-aryl H), 4.71 (dd, J$_{H-H(F)}$=9.0, 5.0 Hz, 2H, p-F-aryl H), 3.81 (m, 2H, OCH$_2$), 3.41 (m, 2H, OCH$_2$), 2.34 (s, 6H, p-Me), 1.89 (s, 4H, $^t$OCT CH$_2$), 1.86 (d, J$_H$-H=15 Hz, 2H, $^t$OCT CH$_2$), 1.76 (d, J$_{H-H}$=15 Hz, 2H, $^t$OCT CH$_2$), 1.64 (s, 6H, $^t$OCT CMe$_2$), 1.55 (m, 2H, OCH$_2$CH$_2$), 1.51 (s, 6H, $^t$OCT CMe$_2$), 1.45 (s, 6H, $^t$OCT CMe$_2$), 1.38 (s, 6H, $^t$OCT CMe$_2$), 0.81 (s, 18H, $^t$OCT CMe$_3$), 0.73 (s, 18H, $^t$OCT CMe$_3$), −1.61 (s, 6H, Hf-Me).

In some embodiments at least one of the at least one metal-ligand complex of formula (I) is any one of metal-ligand complexes (21) to (40).

In some embodiments at least one of the at least one metal-ligand complex of formula (I) is any one of metal-ligand complexes (1) to (20) except where hafnium is replaced by titanium. In some embodiments at least one of the at least one metal-ligand complex of formula (I) is any one of metal-ligand complexes (21) and (2',2''-(propane-1,3-diylbis(oxy)) bis(3-(3,6-di-tert-butyl-9H-carbazol-9-yl)-5'-fluoro-5-(2,4,4-trimethylpentan-2-yl)biphenyl-2-ol)dimethyl-titanium, (41).

In some embodiments at least one of the at least one metal-ligand complex of formula (I) is any one of metal-ligand complexes (1) to (20) except where hafnium is replaced by the metal of Group 3 of the Periodic Table of the Elements. In some embodiments at least one of the at least one metal-ligand complex of formula (I) is any one of metal-ligand complexes (1) to (20) except where hafnium is replaced by the metal of Group 5 of the Periodic Table of the Elements. In some embodiments at least one of the at least one metal-ligand complex of formula (I) is any one of metal-ligand complexes (1) to (20) except where hafnium is replaced by the metal of Group 6 of the Periodic Table of the Elements.

General Procedure for Copolymerization of Ethylene with 1-Octene

Summary: conduct ethylene/1-octene polymerization reactions at a reaction temperature of 190° C. in a 2 liter (L) batch reactor with feeds of 125 grams (g) of 1-octene; 633 g of mixed alkanes solvent (e.g., ISOPAR-E); 460 pounds per square inch gauge (psig; 3.17 megapascals (MPa)) of ethylene gas pressure; and optionally 45 psig (0.31 MPa) hydrogen gas as a molecular weight control agent. Prepare catalyst by activating a metal-ligand complex of formula (I) (e.g., the metal ligand complex of Examples 1, 2, 3, or 4) with 1.2 mole equivalents (relative to the number of moles of the metal ligand complex of formula (I)) of an activating co-catalyst that is either trityl borate or bis(octadecyl)methylammonium tetrakis(pentafluorophenyl)borate ([HNMe($C_{18}H_{37}$)$_2$][B($C_6F5$)$_4$], abbreviated as BOMATPB) and another activating co-catalyst that is a triisobutylaluminum-modified methylalumoxane-3A (MMAO-3A). Carry out all polymerization reactions for 10 minutes and then stop them by venting the ethylene to atmospheric pressure (i.e., about 101 kilopascals (kPa)).

Pass all feeds through columns of alumina and Q-5™ catalyst (available from Engelhard Chemicals Inc.) prior to introduction into the 2 L batch reactor. Handle mixtures and solutions of the metal-ligand complex of formula (I) (e.g., in mixed alkanes solvent) and solutions of the activating co-catalysts (e.g., in mixed alkanes solvent) in a glove box under an inert gas atmosphere (e.g., nitrogen or argon gas). With stirring, charge the 2-liter batch reactor with about 633 g of mixed alkanes solvent (Isopar E) and 125 g of 1-octene. Add 45 psig (10 millimoles (mmol)) hydrogen gas ($H_2$) as a molecular weight control agent by differential pressure expansion from a 75 mL volume addition tank at 300 psi (2070 kPa). Heat contents of the batch reactor to a temperature of 190° C., and saturate the contents with ethylene at 460 psig (3.4 MPa). Premix dilute toluene (or mixed alkanes) solutions of the metal-ligand complex of formula (I) and dilute toluene (or mixed alkanes) solutions of the activating co-catalysts. Then transfer the resulting premixture to a catalyst addition tank, and inject the premixture therefrom into the batch reactor. Maintain the polymerization conditions (e.g., reaction temperature) for 15 minutes, adding ethylene on demand to maintain a pressure at or above 5 pounds per square inch (psi) (34.5 kilopascals (kPa)); record weight of ethylene added. Continuously remove heat from the resulting reaction mixture via heat transfer to an internal cooling coil. After the 15 minutes, remove the resulting solution from the batch reactor, quench the reaction with 2-propanol, and stabilize the resulting quenched mixture against further polymerization by adding 10 mL of a mixed alkanes solution containing approximately 67 milligrams (mg) of a hindered phenol antioxidant (IRGANOX™1010 from Ciba Geigy Corporation) and 133 mg of a phosphorus stabilizer (IRGAFOS™168 from Ciba Geigy Corporation). Recover the resulting poly(ethylene-co-1-octene) copolymer (PEO) products by drying them for about 12 hours in a temperature-ramped vacuum oven with a starting temperature of 25° C. and a final temperature of 140° C.

Determine melting and crystallization temperatures of poly(ethylene-co-1-octene) copolymer (PEO) products by DSC using DSC 2910 instrument from TA Instruments, Inc. DSC samples are first heated from room temperature to 180° C. at a heating rate of 10° C. per minute. Hold at 180° C. for from 2 minutes to 4 minutes, then cool the sample to −40° C. at a cooling rate of 10° C. per minute. Hold at −40° C. for from 2 minutes to 4 minutes, and then heat the sample to 160° C. at a heating rate of 10° C. per minute.

Determine $M_w$ and ratio of $M_w/M_n$ (polydispersity index or PDI) using a Polymer Labs™ 210 high temperature gel permeation calorimeter.

Determine mole percent (mol %) 1-octene incorporation and density, Prepare samples using 13 milligrams (mg) of polyolefin sample. Dilute the polyolefin sample with 16 mL of 1,2,4-trichlorobenzene (TCB; stabilized with BHT), and heat and shake the resulting diluted mixture at 160° C. for 2 hours to give a solution, which is cooled to room temperature. Deposit 140 microliters of cooled polymer solution onto a silica wafer, heat to 140° C. until the sample is dried, and analyze the dried sample using a Nicolet Nexus 670 FT-IR instrument with version 7.1 software and equipped with an AutoPro auto sampler.

Between polymerization runs, wash the batch reactor out by adding thereto 850 g of mixed alkanes and heating to 150° C. Then empty the batch reactor of the resulting heated mixed alkanes immediately before beginning a new polymerization run.

Examples A1 and A2

Copolymerizations of Ethylene with 1-octene to Give a poly(ethylene-Co-1-octene)copolymer (PEO) Using the Metal-Ligand Complex (1) of Example 1

Follow the general ethylene/1-octene polymerization procedure described above using the metal-ligand complex (1) of Example 1 as the metal-ligand complex of formula (I), repeating the procedure two separate times:

Each of Examples A1 and A2: using 0.1 micromole (μmol) of the metal-ligand complex (1) of Example 1; activating co-catalysts that are BOMATPB (0.12 μmol) and MMAO-3A (1.2 μmol); and a polymerization reaction temperature of 190° C.

Results of Examples A1 and A2 are shown below in Tables 1 and 2.

TABLE 1 certain characterizations of process of Examples A1 and A2 employing metal-ligand complex (1).

| Ex. No. | Metal-ligand complex Number | Metal-ligand complex amount (μmol) | Activating co-catalysts (amount in μmol) | Weight of Ethylene added (g) | Yield of PEO (g) | Catalyst Efficiency (gPEO/gMLC) |
|---|---|---|---|---|---|---|
| A1 | (1) | 0.1 | BOMATPB (0.12)/ MMAO-3A(1.2) | 38.4 | 70.9 | 3,972,200 |
| A2 | (1) | 0.1 | BOMATPB (0.12)/ MMAO-3A(1.2) | 38.5 | 63.5 | 3,558,000 |

TABLE 2 certain characterizations of poly(ethylene-co-1-octene) of Examples A1 and A2.

| Ex. No. | Tm (° C.) | $M_w$ (g/mol) | $M_w/M_n$ | Mol % octene (IR) | Mol % octene (1H-NMR) |
|---|---|---|---|---|---|
| A1 | 68.5 | 191,000 | 2.3 | 11.0 | N/a |
| A2 | 69.7 | 201,000 | 2.6 | 10.5 | N/a |

In Tables 1 and 2, and Tables 3 to 8 appearing later, Ex. No.=Example Number; PEO=poly(ethylene-co-1-octene); Catalyst Efficiency (gPEO/gMLC)=catalyst efficiency calculated by dividing weight in grams of PEO product by weight in grams of metal M of metal-ligand complex used; $T_m$=melting temperature; $M_w$ (g/mol) [or $M_w$ (g/mol)]=weight average molecular weight in grams per mole determined by GPC; $M_w/M_n$=polydispersity index (PDI)=$M_w$ divided by number average molecular weight ($M_n$) (g/mol); Mol % octene ($^1$H-NMR)=mole percent of 1-octene residues incorporated into PEO as determined by $^1$H-NMR spectroscopy; and N/a means not available.

The reactivity ratio for metal-ligand complex (1) of Example 1 is $r_1$ is expected to be about $r_1$ 11 to 12.

Example A3

Copolymerizations of Ethylene with 1-octene to Give a poly(ethylene-co-1-octene) Using the Metal-Ligand Complex (1) of Example 1

Follow the general ethylene/1-octene polymerization procedure described above for Example A1 except employ 0.14 μmol of the metal-ligand complex (1); 0.156 mol BOMATPB; 10 μmol MMAO-3A; 250 g 1-octene; and a polymerization temperature of 170° C. Determine mol % octene-derived content by NMR and calculate $r_1$ the comonomer mol % in copolymer and comonomer mole fraction in the reactor as described previously. Results of Example A3 are shown later in Tables 3 and 4.

Example B1

Copolymerizations of Ethylene with 1-octene to Give a poly(ethylene-co-1-octene) Copolymer Using the Metal-Ligand Complex (2) of Example 2

Follow the general ethylene/1-octene polymerization procedure described above for Example A3 except employ the metal-ligand complex (2) instead of metal-ligand complex (1). Determine mol % octene-derived content by NMR and calculate $r_1$ from the comonomer mol % in copolymer and comonomer mole fraction in the reactor as described previously. Results of Example B1 are shown below in Tables 3 and 4.

TABLE 3 certain characterizations of process of Examples A3 and B1 employing metal-ligand complex (1) or (2), respectively.

| Ex. No. | Metal-ligand complex Number | Metal-ligand complex amount (μmol) | Activating co-catalysts (amount in μmol) | Yield of PEO (g) | Catalyst Efficiency (gPEO/gMLC) |
|---|---|---|---|---|---|
| A3 | (1) | 0.14 | BOMATPB (0.156)/ MMAO-3A (10) | 45.9 | 1,837,000 |
| B1 | (2) | 0.14 | BOMATPB (0.156)/ MMAO-3A (10) | 43.4 | 1,737,000 |

TABLE 4 certain characterizations of poly(ethylene-co-1-octene)s of Examples A3 and B1.

| Ex. No. | Tm (° C.) | $M_w$ (g/mol) | $M_w/M_n$ | $r_1$ | Mol % octene (1H-NMR) |
|---|---|---|---|---|---|
| A3 | 48 | 309,000 | 2.7 | 11.3 | 14.1 |
| B1 | 42 | 249,000 | 2.3 | 9.5 | 16.4 |

General Procedure for Copolymerization of Ethylene with 1-butene

Conduct ethylene/1-butene copolymerizations in a 2 L Parr batch reactor. Heat the reactor with an electrical heating mantle, and cool it with an internal serpentine cooling coil containing cooling water. Control and monitor both the reactor and the heating/cooling system with a Camile TG process computer. Fit the bottom of the reactor with a dump valve, which is used to empty the reactor contents into a SS dump pot that is prefilled with a catalyst kill solution (typically 5 mL of an Irgafos/Irganox/toluene mixture). Vent the dump pot to a 30 gallon (110 L) blowndown tank, with both the pot and the tank being purged with nitrogen gas. All chemicals used for polymerization or catalyst makeup are run through purification columns to remove any impurities that may effect polymerization. Pass 1-butene and mixed alkanes solvent through two columns, the first containing A2 alumna, and the second containing Q5 reactant. Pass ethylene through two columns, the first containing A204 alumna and 4 A° mole sieves, the second containing Q5 reactant. Pass hydrogen gas through a single column containing A204 alumna, 3 A° mole sieves and Q5 reactant. Pass nitrogen gas (used for transfers) through a single column containing A204 alumna, 4 A° mole sieves and Q5 reactant.

Load the reactor first from a shot tank that contains mixed alkanes solvent (ISOPAR E). Fill the shot tank to load setpoints by use of a lab scale which the tank is mounted on. After solvent addition (533 mL), add hydrogen gas (500 psig; 3.7 MPa; 10 mmol) through a shot tank using pressure drop to measure the amount added to the reactor. The pressure is measured by a Validyne sensor read by the Camile TG process computer to control hydrogen gas addition valves. Then add 1-butene (100 g) to the reactor through a MICRO MOTION™ flow meter (Micro Motion, Inc., Boulder, Colo., USA). Heat contents of the reactor up to the polymerization temperature setpoint (160° C. unless otherwise indicated) during the addition of hydrogen gas and 1-butene. Add the ethylene (500 psi; 3.7 MPa) to the reactor when at reaction temperature to maintain reaction pressure setpoint. Monitor ethylene addition amounts by the MICRO MOTION™ flow meter.

Mix the metal-ligand complex of formula (I) (precatalyst) and BOMATPB (1.1 mole equivalents based on precatalyst)/MMAO-3A (10 μmol) activating co-catalyst(s) (activator(s)) with an appropriate amount of toluene (or mixed alkanes) to achieve a desired molarity solution. Handle the precatalyst and activator(s) in an inert glovebox, drawn into a syringe and pressure transferred into a catalyst shot tank. Rinse three times with toluene (or mixed alkanes), 5 mL each. Immediately after catalyst addition the run timer begins. Usually within the first 2 minutes of successful catalyst runs, an exotherm and decreasing reactor pressure are observed. Add ethylene to maintain the reaction pressure setpoint in the reactor. Run these polymerizations 10 minutes with agitation, then stop the agitator, and open the bottom dump valve empty reactor contents into the SS dump pot. Pour resulting contents of the SS dump pot into trays placed in a lab hood where the solvent is evaporated off overnight. Transfer the trays containing the residual ethylene/1-butene copolymer (PEB) to a vacuum oven, and heat up to 140° C. under vacuum to remove any remaining solvent. Cool the trays and their contents to ambient temperature, and weight the resulting dried ethylene/1-butene copolymer. Calculate yield/efficiencies and characterize the poly(ethylene-co-1-butene) copolymer in a manner similar to the aforementioned characterization of the poly (ethylene-co-1-octene)copolymer.

Examples C1 and D1

Copolymerizations of Ethylene with 1-butene to Give a (poly(ethylene 1-butene)copolymer (PEB) Using the Metal-Ligand Complex (1) of Example 1 or Metal-Ligand Complex (2) of Example 2

Follow the general ethylene/1-butene polymerization procedure described above using the metal-ligand complex (1) of Example 1 or the metal-ligand complex (2) of Example 2 as the precatalyst. Determine mol % butene-derived content by NMR and calculate $r_1$ the comonomer mol % in copolymer and comonomer mole fraction in the reactor as described previously. Results of Examples C1 and D1 are shown below in Tables 5 and 6.

TABLE 5 certain characterizations of process of Examples C1 and D1 employing metal-ligand complex (1) or (2), respectively.

| Ex. No. | Metal-ligand complex Number | Metal-ligand complex amount (µmol) | Activating co-catalysts (amount in (µmol) | Yield of PEB (g) | Catalyst Efficiency (gPEB/ gMLC) |
|---|---|---|---|---|---|
| C1 | (1) | 0.05 | BOMATPB (0.055)/ MMAO-3A (10) | 9.5 | 1,065,000 |
| D1 | (2) | 0.08 | BOMATPB (0.088)/ MMAO-3A (10) | 27.8 | 1,947,000 |

TABLE 6 certain characterizations of poly(ethylene-co-1-butene)s of Examples C1 and D1.

| Ex. No. | Tm (° C.) | $M_w$ (g/mol) | $M_w/M_n$ | $r_1$ | Mol % butene (1H-NMR) |
|---|---|---|---|---|---|
| C1 | 61 | 377,000 | 2.4 | <20 | 12.3 |
| D1 | 56 | 340,000 | 2.4 | <20 | 14.3 |

Mol % butene (1H-NMR) = mole percent of 1-butene residues incorporated into PEB as determined by $^1$H-NMR spectroscopy.

General Procedure for Copolymerization of Ethylene with Propene and Ethylidene Norbornene Reactor set up is same as described previously for the ethylene/1-butene polymerization. Pass the alkanes solvent through 2 columns, the first containing A2 alumina, and the second containing Q5 reactant. Pass ethylene through 2 columns, the first containing A204 alumina and 4 A° mole sieves, the second containing Q5 reactant. Pass propylene through 2 columns, the first containing A204 and A2, the second containing Q5 reactant. Pass the nitrogen gas, which is used for transfers, through a single column containing A204 alumina, 4 A° mole sieves and Q5 reactant. Pass hydrogen gas through a single column containing A204 alumina, 3 A° mole sieves and Q5 reactant. Pass ethylidene norbornene (ENB) through a column of A2 in the inert glovebox.

Load a liquid weighing shot tank first for mixed alkanes solvent (ISOPAR E) as before. Add ethylidene norbornene to the liquid weighing shot tank from the glovebox. Add the mixed alkanes (700 mL) and ethylidene norbornene (g) to the reactor. Then add hydrogen gas through a shot tank using pressure drop to measure the amount added to the reactor. Measure the hydrogen gas pressure with a Validyne sensor read by the Camile TG process computer to control the addition valves. Then add propylene (100 g) to the reactor through a MICRO MOTION™ flow meter. Heat contents of the reactor up to the polymerization temperature setpoint (120° C. or 160° C., as the case may be) during the addition of hydrogen gas and propylene. Add ethylene to the reactor when at reaction temperature to maintain reaction pressure setpoint. Monitor ethylene addition amounts with the MICRO MOTION™ flow meter.

Mix the metal-ligand complex of formula (I) (precatalyst) and BOMATPB (1.1 mole equivalents based on precatalyst)/ MMAO-3A (10 µmol) activating co-catalyst(s) (activator(s)) with an appropriate amount of toluene (or mixed alkanes) to achieve a desired molarity solution. Handle the precatalyst and activator(s) in an inert glovebox, drawn into a syringe and pressure transferred into a catalyst shot tank. Rinse three times with toluene (or mixed alkanes), 5 mL each. Immediately after catalyst addition the run timer begins. Usually within the first 2 minutes of successful catalyst runs, an exotherm and decreasing reactor pressure are observed. Add ethylene to maintain the reaction pressure setpoint in the reactor. Run these polymerizations 10 minutes with agitation, then stop the agitator, and open the bottom dump valve empty reactor contents into the SS dump pot. Pour resulting contents of the SS dump pot into trays placed in a lab hood where the solvent is evaporated off overnight. Transfer the trays containing the residual ethylene/propene/ethylidene norbornene terpolymer (EPDM) to a vacuum oven, and heat up to 140° C. under vacuum to remove any remaining solvent. Cool the trays and their contents to ambient temperature, and weight the resulting dried EPDM. Calculate yield/efficiencies and characterize the EPDM in a manner similar to the aforementioned characterization of the poly(ethylene-co-1-octene)copolymer.

Examples E1 and E2; F1 and F2

Copolymerizations of Ethylene/Propene/Ethylidene Norbornene to Give an Ethylene/Propene/Ethylidene Norbornene Terpolymer (EPDM) Using the Metal-Ligand Complex (1) of Example 1 (Two Times) or Metal-Ligand Complex (2) of Example 2 (Two Times)

Follow the general procedure described above using the metal-ligand complex (1) of Example 1 or the metal-ligand complex (2) of Example 2 as the precatalyst to give the EPDM of Examples E1, E2, F1, and F2, respectively. Determine mol % propene- and ethylidene norbornene-derived contents by 13C-NMR. Results of Examples E1, E2, F1, and F2 are shown below in Tables 7 and 8.

TABLE 7 certain characterizations of process of Examples E1, E2, F1, and F2 employing metal-ligand complex (1) or (2), respectively.

| Ex. No. | Metal-ligand complex Number | Metal-ligand complex amount (μmol) | Polymerization Temperature (° C.) | Activating co-catalysts (amount in μmol) | Yield of EPDM (g) | Catalyst Efficiency (gEPDM/gMLC) |
|---|---|---|---|---|---|---|
| E1 | (1) | 0.07 | 120 | BOMATPB (0.077)/ MMAO-3A (10) | 10.7 | 856,000 |
| E2 | (1) | 0.14 | 160 | BOMATPB (0.154)/ MMAO-3A (10) | 9.9 | 396,000 |
| F1 | (2) | 0.07 | 120 | BOMATPB (0.077)/ MMAO-3A (10) | 8.2 | 656,000 |
| F2 | (2) | 0.2 | 160 | BOMATPB (0.22)/ MMAO-3A (10) | 15.9 | 445,000 |

TABLE 8 certain characterizations of EPDM of Examples E1, E2, F1, and F2.

| Ex. No. | Tm (° C.) | $M_w$ (g/mol) | $M_w/M_n$ | Mol % propene (13C-NMR) | Mol % ethylidene norbornene (13C-NMR) |
|---|---|---|---|---|---|
| E1 | N/a | 241,000 | 2.6 | 22 | 2.0 |
| E2 | N/a | 166,000 | 2.2 | 25.7 | 4.6 |
| F1 | N/a | 234,000 | 2.5 | 25.3 | 2.3 |
| F2 | N/a | 136,000 | 2.2 | 27.6 | 4.7 |

Mol % propene (13C-NMR) = mole percent of propene residues, and Mol % ethylidene norbornene (13C-NMR) = mole percent of ethylidene norbornene residues, incorporated into EPDM as determined by $^{13}$C-NMR spectroscopy.

Comparative Example(s) (non-invention) are provided below as a contrast to certain embodiments of the present invention and are not meant to be construed as being either prior art or representative of non-invention examples.

In a similar manner to the procedures described previously for Examples 1 and 2 except using 2,4-difluoro-2-iodophenol instead of 4-fluoro-2-iodophenol, (P7) and either 2,4-dichloro-2-iodophenol or 4-chloro-6-methyl-2-iodophenol instead of 4-chloro-2-iodophenol, (P9), prepare Comparative Examples (CE1), (CE2), and (CE3), respectively:

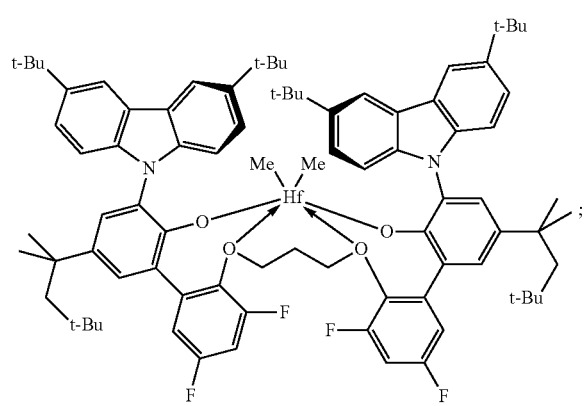
(CE1)

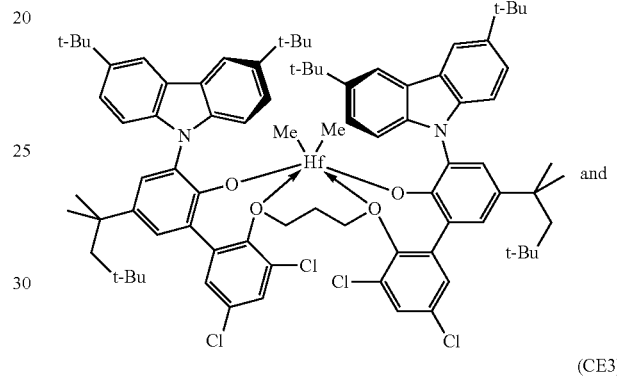
(CE2)

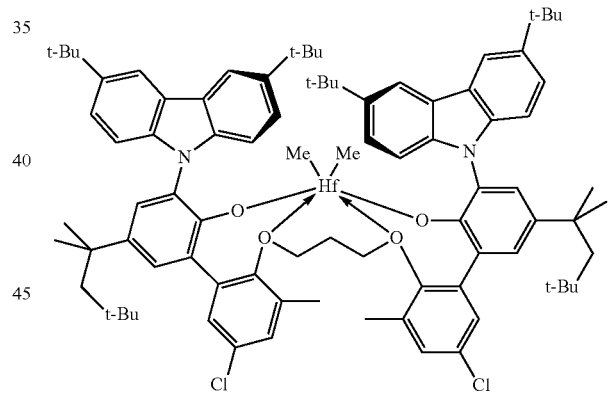
(CE3)

Record $^1$H NMR (500 MHz, $C_6D_6$):

CE1: δ 8.54 (d, J=1.7 Hz, 2H), 8.35 (d, J=1.9 Hz, 2H), 7.84 (d, J=2.4 Hz, 2H), 7.83 (dd, J=8.1, 2.0 Hz, 2H), 7.73 (dd, J=8.6, 1.9 Hz, 2H), 7.56 (dd, J=8.7, 0.4 Hz, 2H), 7.40 (dd, J=8.8, 1.9 Hz, 2H), 7.19 (d, J=2.5 Hz, 2H), 6.65 (ddd, J=8.9, 2.9, 1.7 Hz, 2H), 6.02 (ddd, J=8.8, 8.1, 3.1 Hz, 2H), 3.84 (dt, J=10.7, 5.6 Hz, 2H), 3.16 (dt, J=10.6, 5.3 Hz, 2H), 1.64 (d, J=14.5 Hz, 2H), 1.58 (s, 18H), 1.57 (d, J=14.5 Hz, 2H), 1.31 (s, 18H), 1.25 (s, 6H), 1.21 (s, 6H), 1.19 (p, J=5.7 Hz, 2H), 0.83 (s, 18H), −0.88 (s, 6H).

CE2: δ 8.54 (d, J=1.8 Hz, 2H), 8.34 (d, J=1.8 Hz, 2H), 7.98 (d, J=8.5 Hz, 2H), 7.94 (d, J=2.4 Hz, 2H), 7.80 (dd, J=8.6, 1.9 Hz, 2H), 7.65 (d, J=8.8 Hz, 2H), 7.43 (dd, J=8.8, 1.9 Hz, 2H), 7.16 (d, J=2.4 Hz, 2H), 7.06 (d, J=2.6 Hz, 2H), 6.66 (d, J=2.6 Hz, 2H), 3.91 (dt, J=10.3, 5.1 Hz, 2H), 3.28 (dt, J=10.6, 5.5 Hz, 2H), 1.65 (d, J=14.5 Hz, 2H), 1.59 (s, 18H), 1.56 (d, J=14.5 Hz, 2H), 1.35 (s, 18H), 1.31 (dt, J=10.6, 5.1 Hz, 2H), 1.24 (s, 6H), 1.21 (s, 6H), 0.83 (s, 18H), −0.73 (s, 6H).

CE3: δ 8.53 (d, J=1.9 Hz, 2H), 8.35 (d, J=1.9 Hz, 1H), 7.92 (d, J=8.6 Hz, 2H), 7.91 (d, J=2.5 Hz, 2H), 7.74 (dd, J=8.6, 2.0 Hz, 2H), 7.68 (d, J=8.8 Hz, 2H), 7.43 (dd, J=8.8, 1.9 Hz, 2H), 7.28 (d, J=2.5 Hz, 2H), 7.16 (d, J=2.6 Hz, 2H), 6.50 (dd, J=2.6, 0.6 Hz, 2H), 3.59 (dt, J=9.9, 4.9 Hz, 2H), 3.24 (dt, J=10.7, 5.5 Hz, 2H), 1.65 (d, J=14.5 Hz, 2H), 1.56 (s, 18H), 1.56 (d, J=14.5 Hz, 2H), 1.33 (s, 18H), 1.32 (p, J=5.0 Hz, 2H), 1.24 (s, 6H), 1.21 (s, 6H), 1.20 (s, 6H), 0.83 (s, 18H), −0.74 (s, 6H).

For comparison purposes, repeat the ethylene/1-octene polymerization procedure once with metal-ligand complex (CE1), once with metal-ligand complex (CE2), once with metal-ligand complex (CE3), and 16 times with metal-ligand complex (CE3). The reactivity ratio for metal-ligand complex (CE1) is $r_1$ about 40 (measured with one polymer sample). The reactivity ratio for metal-ligand complex (CE2) is $r_1$ about 75 (measured with one polymer sample). The reactivity ratio for metal-ligand complex (CE3) is $r_1$ about 65 (measured with the 16 polymer samples) or $r_1$ about 58 (measured with the one polymer sample).

As shown by the above description, including the Examples, the invention catalysts (co)polymerize olefins, including copolymerizing ethylene and an olefin comonomer in the invention process. This polymerization of the invention process desirably can be conducted at high reaction temperatures and yields the invention polyolefin copolymer in high yield and with a high degree of olefin comonomer incorporation therein, as shown by the reactivity ratios $r_1$<20. The invention catalyst shows high catalytic activity at the high reaction temperatures. The invention precatalyst and catalyst also would show solubility or improved solubility in the ($C_2$-$C_{40}$)alkane or $C_3$-$C_{40}$)cycloalkane solvent, even at room temperature.

While the invention has been described above according to its preferred embodiments, it can be modified within the spirit and scope of this disclosure. This application is therefore intended to cover any variations, uses, or adaptations of the instant invention using the general principles disclosed herein. Further, the instant application is intended to cover such departures from the present disclosure as come within the known or customary practice in the art to which this invention pertains and which fall within the limits of the following claims.

What is claimed is:

1. A process for copolymerizing polymerizable olefins, the process comprising contacting together ethylene, a ($C_3$-$C_{40}$) olefin comonomer, a first aprotic solvent, and a catalytic amount of a catalyst, wherein the catalyst is prepared before the contacting step as a solution in a second aprotic solvent and wherein the catalyst comprises a mixture or reaction product of a metal-ligand complex and at least one activating co-catalyst; wherein the metal-ligand complex is at least one metal-ligand complex (1) or (2):

(2',2"-(propane-1,3-diylbis(oxy))bis(3-(3,6-di-tert-butyl-9H-carbazol-9-yl)-5'-fluoro-5-(2,4,4-trimethylpentan-2-yl)biphenyl-2-ol)dimethyl-hafnium, (1); or (2',2"-(propane-1,3-diylbis(oxy))bis(3-(3,6-di-tert-butyl-9H-carbazol-9-yl)-5'-chloro-5-(2,4,4-trimethylpentan-2-yl)biphenyl-2-ol)dimethyl-hafnium, (2);

wherein the ratio of total number of moles of the at least one metal-ligand complex to total number of moles of the at least one activating co-catalyst is from 1:10,000 to 100:1;

wherein the contacting is performed under olefin polymerizing conditions that include a reaction temperature of from 30 degrees Celsius to 300 degrees Celsius and prepares a polyolefin copolymer comprising repeat units comprising residuals of ethylene and the ($C_3$-$C_{40}$)olefin comonomer;

wherein the process forms reactive chains (in situ) and is characterized by a reaction rate constant $k_{11}$ for adding the ethylene to a first reactive chain end comprising an ethylene residual; a reaction rate constant $k_{12}$ for adding the ($C_3$-$C_{40}$)olefin comonomer to a second reactive chain end comprising an ethylene residual; and a reactivity ratio $r_1$ equal to $k_{11}$ divided by $k_{12}$ of less than 20 ($r_1$=$k_{11}/k_{12}$<20); and wherein the first and second aprotic solvents comprise ($C_2$-$C_{40}$)alkane solvents, ($C_3$-$C_{40}$)cycloalkane solvents or mixtures thereof.

2. A ligand, wherein the ligand is the ligand (Q1) or (Q2): 2',2"-(propane-1,3-diylbis(oxy))bis(3-(3,6-di-tert-butyl-9H-carbazol-9-yl)-5'-fluoro-5-(2,4,4-trimethylpentan-2-yl)biphenyl-2-ol, (Q1); or 2',2"-(propane-1,3-diylbis(oxy))bis(3-(3,6-di-tert-butyl-9H-carbazol-9-yl)-5'-chloro-5-(2,4,4-trimethylpentan-2-yl)biphenyl-2-ol, (Q2).

* * * * *